US012708664B2

(12) United States Patent
Blanchetot et al.

(10) Patent No.: US 12,708,664 B2
(45) Date of Patent: Aug. 18, 2026

(54) METHODS OF TREATING PARAPROTEINEMIC NEUROPATHY WITH ANTI-C2 ANTIBODIES

(71) Applicant: argenx BV, Ghent (BE)

(72) Inventors: Christophe Blanchetot, Ghent (BE); Kevin Budding, Vleuten (NL); Erik Hack, Diemen (NL); Karen Silence, Ghent (BE); Inge Van De Walle, Ghent (BE); Ludo Van Der Pol, Amersfoort (NL); Peter Boross, Utrecht (NL)

(73) Assignee: argenx BV, Ghent (BE)

( * ) Notice: Subject to any disclaimer, the term of this patent is extended or adjusted under 35 U.S.C. 154(b) by 1305 days.

(21) Appl. No.: 17/608,637

(22) PCT Filed: May 21, 2020

(86) PCT No.: PCT/EP2020/064234
§ 371 (c)(1),
(2) Date: Nov. 3, 2021

(87) PCT Pub. No.: WO2020/234432
PCT Pub. Date: Nov. 26, 2020

(65) Prior Publication Data

US 2025/0066460 A1 Feb. 27, 2025

(30) Foreign Application Priority Data

May 21, 2019 (GB) .................................... 1907153

(51) Int. Cl.

| | |
|---|---|
| ***A61P 25/02*** | (2006.01) |
| ***A61K 39/395*** | (2006.01) |
| *C07K 16/18* | (2006.01) |
| *C07K 16/40* | (2006.01) |
| *C12N 9/64* | (2006.01) |

(52) U.S. Cl.
CPC .......... *A61K 39/3955* (2013.01); *A61P 25/02* (2018.01); *C07K 16/18* (2013.01); *C07K 16/40* (2013.01); *C07K 2317/24* (2013.01); *C07K 2317/56* (2013.01); *C07K 2317/565* (2013.01); *C12N 9/6408* (2013.01); *C12Y 304/21043* (2013.01)

(58) Field of Classification Search
CPC ..... A61K 39/3955; A61P 25/02; C07K 16/18; C07K 16/40; C12N 9/648; C12Y 304/21043
See application file for complete search history.

(56) References Cited

U.S. PATENT DOCUMENTS

| | | | |
|---|---|---|---|
| 6,998,468 | B2 | 2/2006 | Fung et al. |
| 7,927,592 | B2 | 4/2011 | Fung et al. |
| 8,163,881 | B2 | 4/2012 | Ober |
| 8,221,756 | B2 | 7/2012 | Fung et al. |
| 8,834,871 | B2 | 9/2014 | Ober |
| 8,911,735 | B2 | 12/2014 | Fung et al. |
| 9,944,717 | B2 | 4/2018 | Hack et al. |
| 10,717,785 | B2 | 7/2020 | Hack et al. |
| 11,161,900 | B2 | 11/2021 | Blanchetot et al. |
| 11,591,386 | B2 | 2/2023 | Blanchetot et al. |
| 11,708,403 | B2 | 7/2023 | Blanchetot et al. |
| 2011/0104156 | A1 | 5/2011 | Christadoss et al. |
| 2015/0064195 | A1 | 3/2015 | Kupper et al. |
| 2015/0064395 | A1 | 3/2015 | Kupper et al. |
| 2016/0108134 | A1 | 4/2016 | Hack et al. |
| 2018/0319895 | A1 | 11/2018 | Hack et al. |
| 2020/0239554 | A1 | 7/2020 | Blanchetot et al. |
| 2022/0119509 | A1 | 4/2022 | Blanchetot et al. |
| 2022/0267424 | A1 | 8/2022 | Blanchetot et al. |
| 2024/0002484 | A1 | 1/2024 | Blanchetot et al. |

FOREIGN PATENT DOCUMENTS

| | | | |
|---|---|---|---|
| CA | 3055781 | A1 | 9/2018 |
| EP | 1265929 | A1 | 12/2002 |
| JP | 2018534246 | A | 11/2018 |
| WO | WO 2001/070818 | A1 | 9/2001 |
| WO | WO 2008/044928 | A1 | 4/2008 |
| WO | WO 2010/056399 | A1 | 5/2010 |
| WO | WO 2013/036778 | A2 | 3/2013 |
| WO | WO 2014/096958 | A1 | 6/2014 |

(Continued)

OTHER PUBLICATIONS

Benjamini et al, 1991. Immunology: A Short Course, 2nd edition, p. 40 only.*
Bentley et al, 1986. Biochem J. 239:339-345.*
Ferrara et al (2015. mAbs. 7(1): 32-41).*
Jinka et al, 2014. Curr Treat Options Neurol. 16:269.*
U.S. Appl. No. 14/892,850 2016/0108134 U.S. Pat. No. 9,944,717, filed May 22, 2014 Apr. 21, 2016 Apr. 17, 2018, Cornelis Erik Hack.
U.S. Appl. No. 15/903,810 2018/0319895 U.S. Pat. No. 10,717,785, filed Feb. 23, 2018 Nov. 8, 2018 Jul. 21, 2020, Cornelis Erik Hack.
U.S. Appl. No. 17/608,637, filed Nov. 3, 2021, Christophe Blanchetot.
U.S. Appl. No. 16/714,264 2020/0239554 U.S. Pat. No. 11,161,900, filed Dec. 13, 2019 Jul. 30, 2020 Nov. 2, 2021, Christophe Blanchetot.

(Continued)

*Primary Examiner* — Zachary C Howard
(74) *Attorney, Agent, or Firm* — COOLEY LLP; Andrew T. Wilkins; Kayla L. Metzger

(57) ABSTRACT

The present invention relates to a method of treating a paraproteinemic neuropathy in a subject by administering to the subject an antagonist of the complement system. The antagonist inhibits the complement system upstream of complement factor C5. More specifically, the antagonist may be an antibody or an antigen-binding fragment thereof that blocks or inhibits the complement system by inhibiting the C2b domain of complement factor C2. The paraproteinemic neuropathies that may be treated include, in particular, multifocal motor neuropathy (MMN), chronic inflammatory demyelinating polyneuropathy (CIDP), and Guillain-Barre syndrome (GBS).

11 Claims, 21 Drawing Sheets

Specification includes a Sequence Listing.

(56) References Cited

FOREIGN PATENT DOCUMENTS

| | | | |
|---|---|---|---|
| WO | WO 2014/186599 | A2 | 11/2014 |
| WO | WO 2014/189378 | A1 | 11/2014 |
| WO | WO 2015/089368 | A2 | 6/2015 |
| WO | WO 2016/073685 | A1 | 5/2016 |
| WO | WO-2017046172 | A1 | 3/2017 |
| WO | WO 2017/091719 | A1 | 6/2017 |
| WO | WO 2017/129737 | A1 | 8/2017 |
| WO | WO 2017/196960 | A1 | 11/2017 |
| WO | WO 2019/089922 | A1 | 5/2019 |
| WO | WO 2020/121282 | A1 | 6/2020 |
| WO | 2020234432 | A1 | 11/2020 |

OTHER PUBLICATIONS

U.S. Appl. No. 17/491,656, filed Oct. 1, 2021, Christophe Blanchetot.
U.S. Appl. No. 17/572,518, filed Jan. 10, 2022, Christophe Blanchetot.
Lin et al., "Improved affinity of a chicken single-chain antibody to avian infectious bronchitis virus by site-directed mutagenesis of complementarity-determining region H3", African Journal of Biotechnology, Dec. 12, 2011, 10(79):18294-18302.
McCarthy et al., "Altering the fine specificity of an anti-Legionella single chain antibody by a single amino acid insertion", Journal of Immunological Methods, 2001, 251(1-2):137-149.
Paul, "Fundamental Immunology", under the heading "Fv Structure and Diversity in Three Dimensions", 1993, 3rd Edition, pp. 292-295.
International Preliminary Report on Patentability received for PCT Application No. PCT/NL2014/050327, mailed on Dec. 3, 2015, 8 pages.
"Argenx announces expansion of its pipeline with addition of complement-targeted ARGX-117 for treatment of severe autoimmune diseases", argenx SE, Mar. 22, 2018, Retrieved from url: ,https://www.globenewswire.com/news-release/2018/03/22/1444011/0/en/argenx-announces-expansion-of-its-pipeline-with-addition-of-complement-targeted-ARGX-117-for-treatment-of-severe-autoimmune-diseases.html>.
"Argenx Annual Report 2018", Mar. 26, 2019, Retrieved from url: <https://argenx.com/sites/default/files/media-documents/argenx-annual-report-2018-final.pdf>.
Anderson, C.M., et al., "A Monoclonal Antibody Against Human Complement Component C2," Biochemical Society Transactions, Portland Press Ltd, BG, vol. 15, No. 4, pp. 660-661, Jan. 1, 1987.
Arlaud et al., "The atypical serine proteases of the complement system", Advanced Immunology, 1998, vol. 69, pp. 249-307.
Cats et al., "Correlates of outcome and response to IVIg in 88 patients with multifocal motor neuropathy", Neurology, 2010, pp. 818-825.
Colman, "Effects of amino acid sequence changes on antibody-antigen interactions", Research Immunology, vol. 145; pp. 33-36, 1994.
Combined Search and Examination Report for GB Patent Application No. 1907153.9, mailed Nov. 29, 2019.
Edimara et al., "Applying complement therapeutics to Rare Diseases", Clinical Immunology, 2015, 161: 225-240.
Hahn et al. "A controlled trial of intravenous immunoglobulin in multifocal motor neuropathy", J Peripher Nerv Syst, Dec. 2013, 18(4): 321-330.
Heinz, H.P., et al., "Monoclonal Antibodies Against Components of the Classical Pathway of Complement," Complement and Inflammation, Karger Basel, CH, vol. 6, No. 3, pp. 166-174, Jan. 1, 1989.
Horiuchi et al., "Site-directed mutagenesis of the region around Cys-241 of complement component C2. Evidence for a C4b binding site", Journal of Immunology, 1991, vol. 147, No. 2, pp. 584-589.
Huda, R., et al., "Complement C2 siRNA Mediated Therapy of Myasthenia Gravis in Mice," Journal of Autoimmunity, vol. 42, pp. 94-104, May 1, 2013.
Igawa et al., "Reduced elimination of IgG antibodies by engineering variable region", Protein Engineering, Design and Selection, May 2010, vol. 23, Issue 5, pp. 385-392.
International Search Report and Written Opinion for PCT International Patent Application No. PCT/NL2014/050327, dated Oct. 1, 2014.
International Search Report and Written Opinion for PCT International Patent Application No. PCT/EP2020/064234, dated Oct. 26, 2020.
International Search Report and Written Opinion in related PCT Application No. PCT/IB2019/060802, dated Mar. 31, 2020.
Jackson, et al., "In Vitro Antibody Maturation," Journal of Immunology, 1995, 154: 3310-3319.
Krishnan et al., "The crystal structure of C2a, the catalytic fragment of classical pathway C3 and C5 convertase of human complement", Journal of Molecular Biology, 2007, vol. 367, No. 1, pp. 224-233.
Krishnan, et al., "The Structure of C2b, a Fragment of Complement Component C2 Produced during C3 Convertase Formation," Acta Crystallography, D65: 266-274, 2009.
Lansita et al., "Nonclinical Development of ANX005: A Humanized Anti-Clq Antibody for Treatment of Autoimmune and Neurodegenerative diseases" Int'l Journal of Toxicology, 2017, 36(6): 449-462.
Mauriello et al. "A novel peptide inhibitor of classical and lectin complement activation including ABO incompatibility", Mol Immunol, Jan. 2013, 53(0): 132-139.
McGonigal et al., "Clq-targeted inhibition of the classical complement pathway prevents injury in a novel mouse model of acute motor axonal neuropathy", Acta Neuropathologica Communications, 2016, 4(23): 1-16.
Milder et al., "Structure of complement component C2A: implications for convertase formation and substrate binding", Structure, 2006, vol. 14, No. 10, pp. 1587-1597.
Norman et al., "Three-dimensional structure of a complement control protein module in solution", Journal of Molecular Biology, Jun. 20, 1991, vol. 219, No. 4, pp. 717-725.
Oglesby, et al., "Evidence for a C4b Binding Site on the C2b Domain of C2-1," The Journal of Immunology, 141: 926-931, No. 1, Aug. 1, 1988.
Oglesby, et al., "Probing a C4b-Binding Site(s) on C2b with Murine Monoclonal Antibodies," University of Alabama at Birmingham, Birmingham, AL, no date available.
Oglesby, et al., "Radioassays for Quantitation of Intact Complement Proteins C2 and B in Human Serum," Journal of Immunological Methods, 110: 55-62, 1988.
Phongsisay et al., "Complement inhibitor prevents disruption of sodium channel clusters in a rabbit model of Guillain-Barre syndrome", Journal of Neuroimmunology, 2008, 205: 101-104.
Piepers et al., "IVIg inhibits classical pathway activity and anti-GM1 IgM-mediated complement deposition in MMN", Journal of Neuroimmunology, 2016, 229: 256-262.
Rabia et al., "Understanding and overcoming trade-offs between antibody affinity, specificity, stability and solubility", Biochemical Engineering Journal, vol. 137, pp. 365-374, Jun. 5, 2018.
Ricklin, et al., "Complement-targeted Therapeutics," Nature Biotechnology, vol. 25, No. 11, Nov. 2007.
Ruddy et al., "Hereditary deficiency of the second component of complement (C2) in man: correlation of C2 haemolytic activity with immunochemical measurements of C2 protein", Immunology, Jun. 1970, 18(6): 943-954.
Rudikoff, S. et al., "Single Amino Acid Substitution Altering Antigen-Binding Specificity," Proc. Natl. Acad. Sci. USA, vol. 79, pp. 1979-1983, Mar. 1982.
Spirig et al. "rIgG1 Fc Hexamer Inhibits Antibody-Mediated Autoimmune Disease via Effects on Complement and FcγRs", J Immunol, Apr. 15, 2018, 200(8): 2542-2553.
Stenbaek, E.I., et al., "Human Complement Component C2: Production and Characterization of Polyclonal and Monoclonal Antibodies Against C2," Molecular Immunology, Pergamon, GB, vol. 23, No. 8, pp. 879-886, Aug. 1, 1986.
Wong, et al., "Structural Requirements for a Specificity Switch and for Maintenance of Affinity using Mutational Analysis of a Phage-Displayed Anti-Arsonate Antibody of Fab Heavy Chain First Complementarity-Determining Region," Journal of Immunology, 1998, 160: 5990-5997.

(56) References Cited

OTHER PUBLICATIONS

Wu et al., "Structure-based engineering of a monoclonal antibody for improved solubility", Protein Engineering, Design and Selection, vol. 23, No. 8, pp. 643-651, Jun. 11, 2010.
Xu, et al., "Contribution of the Complement Control Protein Modules of C2 in C4b Binding Assessed by Analysis of C2/Factor B Chimeras," The Journal of Immunology, 158: 5958-5965, 1997.

* cited by examiner

A

Serum
Cleared serum
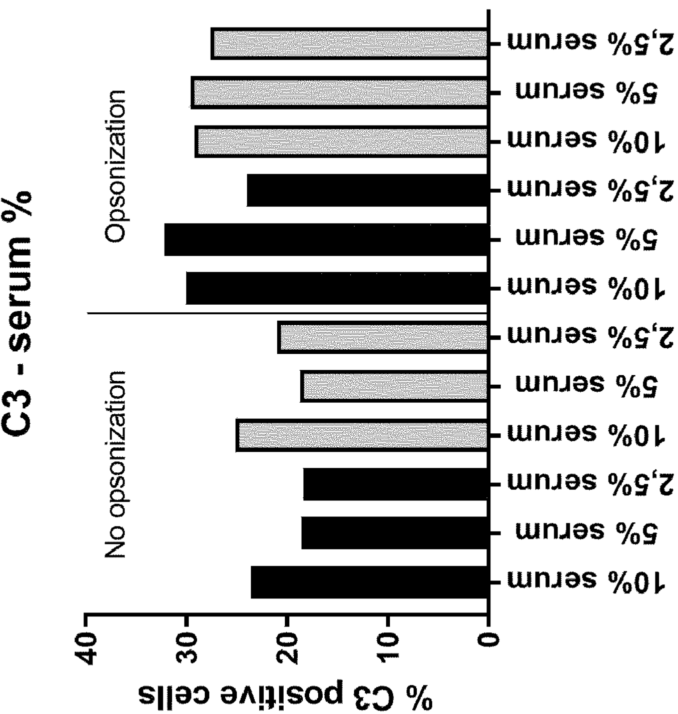
B
C3 - serum %
% C3 positive cells
0
10
20
30
40
No opsonization
Opsonization
10% serum
5% serum
2,5% serum
10% serum
5% serum
2,5% serum
10% serum
5% serum
2,5% serum
10% serum
5% serum
2,5% serum

METHODS OF TREATING PARAPROTEINEMIC NEUROPATHY WITH ANTI-C2 ANTIBODIES

RELATED APPLICATIONS

This application is a 35 U.S.C. § 371 application of International Patent Application No. PCT/EP2020/064234, filed May 21, 2020, which claims priority to Great Britain Patent Application No. 1907153.9, filed May 21, 2019, the entire disclosures of which are hereby incorporated herein by reference.

FIELD OF THE INVENTION

The present invention relates to methods of treating paraproteinemic neuropathies using antagonists of the complement system. The antagonists block or inhibit the complement system upstream of complement factor C5. The paraproteinemic neuropathies that may be treated include, in particular, multifocal motor neuropathy (MMN), chronic inflammatory demyelinating polyneuropathy (CIDP), and Guillain-Barre syndrome (GBS).

SEQUENCE LISTING

The instant application contains a Sequence Listing which has been filed electronically in ASCII format and is hereby incorporated by reference in its entirety. Said ASCII copy, created on May 20, 2022, is named 19952_SL.txt and is 47,652 bytes in size.

BACKGROUND TO THE INVENTION

The complement system is an important facet of the innate immune system that enhances (complements) the ability of antibodies and phagocytic cells to clear microbial intruders and damaged cells from an organism. Complement therefore forms an essential line of defence against infection.

The response to infection has to be rapid and comprehensive enough to prevent risk to the host, but selective enough to avoid damage to healthy cells. Complement typically achieves this delicate balance by employing a tiered and closely regulated cascade system of more than 30 soluble and surface-expressed proteins. Complement factors circulate in the blood as inactive precursor proteins. Activation of the system leads to an activation cascade where one factor activates the subsequent one by specific proteolysis of a complement protein further downstream in the cascade. This cascade can ultimately result in: the production of anaphylatoxins that attract and activate macrophages and leukocytes; formation of the lytic membrane attack complex (MAC); and opsonization of targets for phagocytosis and destruction.

Activation of the complement system can occur via three pathways: the classical pathway; the lectin pathway; and the alternative pathway (see FIG. 1). Each pathway activates a central component, C3, which results in the activation of a common termination pathway leading to the formation of MAC (Muller-Eberhrd, *Annu Rev Biochem* 1988, 57:321). The classical pathway is often referred to as antibody-dependent because it is strongly initiated by IgM or IgG clusters. This pathway is usually activated when the hexameric C1q binds to the Fc regions of IgG or IgM molecules that are present in an antibody/antigen complex. Upon binding, C1s cleaves C4 to produce C4a and C4b. Next, C2 binds to surface-bound C4b (in the presence of $Mg^{2+}$) to form a C4bC2 complex, which is then cleaved by activated C1s into two fragments: a smaller 30 kDa fragment C2b, and a larger 70 kDa fragment C2a, which remains attached to C4b to form the C4bC2a classical pathway C3 convertase. The C3 convertase is capable of cleaving C3 into C3a (an anaphylatoxin; enhances inflammation) and C3b, thereby initiating amplification and downstream effector functions.

Activation of the lectin pathway is mediated by binding of mannose-binding lectins (MBLs), or ficolins, to bacterial carbohydrate motifs expressed on the surface of pathogens or microbes. MBL binding subsequently stimulates the activation of MBL-associated serine proteinase-1 (MASP-1) and MASP-2 leading to cleavage of C4 and C2 leading to generation of the C4bC2a lectin pathway C3 convertase.

The alternative pathway may be considered an amplification loop that is engaged regardless of the initial trigger. C3b directly binds to targets on cell surfaces of microbes, foreign material or damaged tissue. The surface-bound C3b can then bind factor B to form C3bB. This complex in the presence of factor D is cleaved into Ba and Bb. Bb remains associated with C3b to form C3bBb, which is the alternative pathway C3 convertase.

The three pathways therefore converge at the central C3 convertases. The C3 convertases, C4bC2a or C3bBb, form multimeric complexes with additional C3b molecules, yielding the C5 convertases, C4bC2aC3b and C3bBbC3b, respectively. These enzymes preferentially cleave complement factor C5, releasing C5a (an anaphylatoxin; enhances inflammation) and the fragment C5b. C5b recruits and associates with C6 and C7; the complex becomes inserted into cell membranes and interacts with C8; which induces the binding of multiple units of C9 molecules to form the C5b-9 membrane attack complex (MAC) or soluble Terminal Complement Complex (TCC). The MAC forms a pore by inserting itself into cell membranes, resulting mainly in cell lysis of non-nucleated cells (e.g. aged erythrocytes and certain Gram-negative bacteria). However, on nucleated cells, MAC formation is tightly regulated, and its lytic effect can be counteracted by ion pumps. Moreover, sub-lytic levels of MAC can induce damage or activation of host cells and act as a pro-inflammatory mediator. In addition to the MAC-mediated effects of the cascade, the anaphylatoxins, C3a and C5a, act as potent immune modulators, recruiting immune cells to the site of activation. The opsonins, C3b and C4b, can also bind to various complement receptors and mediate immune complex removal, phagocytosis, or stimulation of B-cell responses.

The complement system is further controlled by a number of complement regulatory proteins. These include C1-inhibitor, which inhibits the initiation steps of the classical and lectin pathways; factor H which dissociates C3 convertase; factor I which degrades C4b and C3b; and plasma proteins vitronectin and clusterin and the membrane protein CD59 which inhibit MAC formation (Sahu et al., *Immunol Res* 1998, 17:109; Campbell at al., *Annu Rev Immunol* 1988, 6:161).

Whilst complement forms an essential line of defence against pathogenic organisms, if not properly controlled, these defensive functions can turn against host cells and induce or exacerbate immune, inflammatory, and degenerative conditions. When complement is hyperactivated, as occurs in autoimmune diseases or in subjects with dysfunctional regulatory proteins, it drives a severe inflammatory response in numerous organs (Noris and Remuzzi, *Semin Nephrol* 2013, 33(6): 479-492). Given the ubiquitous expression of complement proteins throughout the body, it is thought that the complement system may play a role in many diseases with an immune component such as inflammatory diseases, degenerative diseases, cancer, and transplant rejection. The complement system is also becoming increasingly implicated in diseases of the central nervous system such as Alzheimer's disease (Carpanini et al., *Front Immunol* 2019, 10:362).

The unique position of complement as both an initial detector of foreign or damaged material and as a downstream orchestrator of immune responses makes complement an attractive therapeutic target. Indeed, clinical development programs are currently reported for inhibitors against more than a dozen distinct complement targets.

Several soluble complement inhibitors have been produced. C1-INH (various manufacturers) is currently approved for the treatment of hereditary angioedema, and is being evaluated in other disorders such as sepsis and ischemia-reperfusion injury. However, C1-INH is a broad serine protease inhibitor that blocks initiating proteases of both the classical and lectin pathways as well as non-complement proteases of the coagulation and contact systems. In contrast, sutimlimab (also known as BIW009, formerly TNT009) is a humanised, monoclonal antibody that is designed to selectively inhibit the classical complement pathway by targeting C1s, and has shown promise in the treatment of haemolytic anemia and cold agglutinin disease. Other antibodies that inhibit key proteins in the cascade have also been developed. Annexon has developed a monoclonal antibody (ANX005) acting at the level of C1q for neurodegenerative and autoimmune disorders, whilst Omeros has developed a monoclonal antibody against MASP-2 (OMS721) as a clinical candidate for the treatment of atypical haemolytic uremic syndrome (aHUS).

Acting at the opposite end of the complement cascade is eculizumab (Soliris®), an anti-C5 antibody that is presently approved for use in the treatment of paroxysmal nocturnal hemoglobinuria (PNH) and aHUS. This antibody binds a site on C5 that prevents its activation by C5 convertases thereby impairing the release of C5a and the formation of MAC. An anti-C5a antibody has also been evaluated (IFX-1), as well as a number of small molecule C5aR1 antagonists (PMX53; PMX205; CCX186) which have shown promise as potential treatments for various disorders.

Antibodies have also been developed to target the C2 protein of the complement cascade. International patent application no. WO2014/189378 describes binding molecules, for example antibodies, with specific C2 activity inhibiting properties. Such binding molecules are described as being useful in the treatment of symptoms of various human diseases, such as inflammatory disease, or ischemia-reperfusion injury.

Despite significant efforts to develop therapeutic agents that target the complement cascade, the clinical success of complement inhibitors has remained limited. This is likely due to the complex nature of the complement cascade. There remains a need to better understand the role of over-active complement activity in various disorders in order to develop effective therapies based on complement inhibition.

SUMMARY OF THE INVENTION

The present inventors have found that targeting the complement cascade upstream of complement factor C5 is likely to be an effective strategy in the treatment of paraproteinemic neuropathies, particularly neuropathies such as multifocal motor neuropathy (MMN), chronic inflammatory demyelinating polyneuropathy (CIDP) and Guillain-Barre syndrome (GBS). Paraproteinemic neuropathies are peripheral neuropathies characterised by the presence of "paraproteins" in the serum. Paraproteins are monoclonal antibodies or immunoglobulins of a specific type that are produced in relative excess by an abnormal clonal proliferation of B-lymphocytes or plasma cells. Unlike normal immunoglobulin antibodies, paraproteins typically cannot fight infection.

As reported and exemplified herein, the complement system plays an important role in the pathology of paraproteinemic neuropathies. In particular, sera from patients having MMN, CIDP and GBS were found to activate complement via opsonization of both Schwann cells and motor neurons in vitro. Importantly, the results presented herein further demonstrate that Schwann cells and motor neurons express high levels of the complement regulatory protein CD59, a factor that prevents terminal polymerization of the membrane attack complex (MAC). The results also show that Schwann cells are resistant to complement-mediated lysis. Taken together, this indicates that in paraproteinemic neuropathies, there is protection against complement-mediated lysis, and that the observed pathology is likely to be MAC-independent i.e. caused by complement proteins upstream of the MAC. Accordingly, the present invention is directed to the treatment of paraproteinemic neuropathies by targeting the complement system upstream of complement factor C5.

In a first aspect, the present invention provides a method of treating a paraproteinemic neuropathy in a subject, the method comprising administering to the subject an antagonist of the complement system, wherein the antagonist inhibits the complement system upstream of complement factor C5. The present invention also provides an antagonist of the complement system for use in treating a paraproteinemic neuropathy in a subject, wherein the antagonist inhibits the complement system upstream of complement factor C5.

In certain embodiments, the antagonist inhibits the classical complement pathway and/or the lectin complement pathway.

In certain embodiments, the paraproteinemic neuropathy is a demyelinating neuropathy.

In certain embodiments, the paraproteinemic neuropathy is characterised by the presence of IgM, IgA or IgG immunoglobulins.

In certain embodiments, the paraproteinemic neuropathy is characterised by the presence of autoantibodies. The autoantibodies may be immunoglobulins of the IgM, IgA or IgG class.

In certain embodiments, the paraproteinemic neuropathy is characterised by the presence of autoantibodies against a neural antigen. The neural antigen may be a ganglioside or the neural antigen may be myelin-associated glycoprotein (MAG). For embodiments wherein the neural antigen is a ganglioside, the ganglioside may be selected from GM1, GM1b, GM2, GM3, GD1a, GD1b, GD2, GD3, GT1a, GT1b, GT3, and GQ1b. In certain preferred embodiments, the ganglioside is GM1.

In certain embodiments, the paraproteinemic neuropathy is selected from: multifocal motor neuropathy (MMN), chronic inflammatory demyelinating polyneuropathy (CIDP), Guillain-Barre syndrome (GBS), Miller Fisher syndrome, acute motor axonal neuropathy (AMAN), acute motor and sensory axonal neuropathy (AMSAN), chronic ataxic neuropathy-ophthalmoplegia-IgM paraprotein-cold agglutinins-disialosyl antibodies (CANOMAD) syndrome, distal acquired demyelinating symmetric (DADS) neuropathy, monoclonal gammopathy associated peripheral neuropathy, anti-MAG peripheral neuropathy, and POEMS syndrome. In certain preferred embodiments, the paraproteinemic neuropathy is multifocal motor neuropathy (MMN), chronic inflammatory demyelinating polyneuropathy (CIDP), or Guillain-Barre syndrome (GBS). The paraproteinemic neuropathy is preferably multifocal motor neuropathy (MMN).

In certain embodiments, the antagonist inhibits the complement system upstream of complement factor C3. In certain embodiments, the antagonist inhibits C1, C1q, C1r or C1s. In certain embodiments, the antagonist inhibits complement factor C2, C2a or C2b. In certain embodiments, the antagonist inhibits complement factor C3, C3a or C3b. In certain embodiments, the antagonist inhibits complement factor C4, C4a or C4b.

In certain embodiments, the antagonist is selected from: an inhibitory RNA species, for example an siRNA or shRNA; a small molecule inhibitor; a biological antagonist, for example an inhibitory peptide or an antibody mimetic such as an affibody, affilin, affitin, adnectin, atrimer, evasin, DARPin, anticalin, avimer, fynomer, versabody or duocalin; or an antibody or antigen-binding fragment thereof.

In certain embodiments, the antagonist is selected from: compstatin Cp40 (Amyndas); PEG-Cp40 (Amyndas); AMY-101 (Amyndas); AMY-201 (Amyndas); APL-1 and APL-2 (Apellis); Cinryze (Shire); CDX-1135 (Celldex); APTO70 Mirococept (MRC); HC3-1496 (InCode); nafamostat (Torii Pharmaceutical), and vaccinia virus complement control protein (VCP).

In preferred embodiments, the antagonist is an antibody or antigen-binding fragment thereof, preferably an IgG antibody or antigen-binding fragment thereof.

In certain embodiments, the antigen-binding fragment is selected from: an antibody light chain variable domain (VL), an antibody heavy chain variable domain (VH), a single chain antibody (scFv), a $F(ab')_2$ fragment, a Fab fragment, an Fd fragment, an Fv fragment, a one-armed (monovalent) antibody, diabodies, triabodies, tetrabodies, unibodies, domain antibodies and nanobodies.

In certain embodiments, the antibody or antigen-binding fragment thereof binds to complement factor C1, C1q, C1s, C2, C2a, C2b, C3, C3a, C3b, C4, C4a or C4b.

In certain embodiments, the antibody or antigen-binding fragment is selected from: sutimlimab (Bioverativ); ANX005 (Annexon); mAb H17 (Elusys Therapeutics); and TNT003 (True North).

In certain embodiments, the antibody or antigen-binding fragment binds to complement factor C2. In certain embodiments, the antibody or antigen-binding fragment binds to the C2b domain of complement factor C2.

In certain embodiments, the antibody or antigen-binding fragment comprises a variable heavy chain domain (VH) and a variable light chain domain (VL) wherein the VH and VL domains comprise the CDR sequences:

```
HCDR3 comprising or consisting of
                                        SEQ ID NO: 2
[EDDHDAFAY];

HCDR2 comprising or consisting of
                                        SEQ ID NO: 3
[DINPNYESTGYNQKFKG];

HCDR1 comprising or consisting of
                                        SEQ ID NO: 4
[DYNMD];

LCDR3 comprising or consisting of
```

-continued

```
                                        SEQ ID NO: 5
[QHSRELPYT];

LCDR2 comprising or consisting of
                                        SEQ ID NO: 6
[LASNLKS];
and

LCDR1 comprising or consisting of
                                        SEQ ID NO: 7
[RASKSVRTSGYNYMH].
```

In certain embodiments, the antibody or antigen-binding fragment comprises a VH domain comprising or consisting of the amino acid sequence of SEQ ID NO: 8 or an amino acid sequence having at least 70% identity thereto and a VL domain comprising or consisting of the amino acid sequence of SEQ ID NO: 9 or an amino acid sequence having at least 70% identity thereto. In certain embodiments, the antibody or antigen-binding fragment comprises a VH domain comprising or consisting of the amino acid sequence of SEQ ID NO: 8 and a VL domain comprising or consisting of the amino acid sequence of SEQ ID NO: 9.

In certain embodiments, the antibody or antigen-binding fragment thereof comprises a human IgG heavy chain constant domain.

In certain embodiments, the antibody or antigen-binding fragment thereof comprises a heavy chain comprising the amino acid sequence of SEQ ID NO: 16 and a light chain comprising the amino acid sequence of SEQ ID NO: 20.

In certain embodiments, the method further comprises administering IVIg to the subject.

In certain embodiments, the method further comprises administering rituximab to the subject.

(A) PL-C treatment reduced expression of both CD59 and CD55 expression via cleavage of the GPI anchor. Expression of CD46, which is a transmembrane protein, was unaffected (right y-axis). PL-C also had no effect on the expression of GM1 (left y-axis, panel A).

(B) Cells are intrinsically protected against C3 fixation. C3 fixation was observed in the absence of opsonization with MMN patient serum, and C3 fixation was slightly increased upon opsonization with MMN patient serum. PL-C treated cells were more susceptible to C3 fixation, especially after opsonization. ARGX- 117 inhibited C3 fixation, although only partial inhibition was seen after opsonization and PL-C treatment. This is presumably due to the combined opsonization density of anti-GM1 antibodies and serum antibodies directed at other epitopes.

(C) Similar results as seen in panel B were observed when MAC fixation was quantified.

(D) Schwann cells were protected against complement-mediated cell lysis—attributable to the high-level CD59 expression. Cells untreated with PL-C remained viable after opsonization and incubation with complement active serum. After PL-C treatment cell lysis was observed when Schwann cells were opsonized with patient-derived anti-GM1 antibodies. This was inhibited to baseline by ARGX-117.

Figure 5:
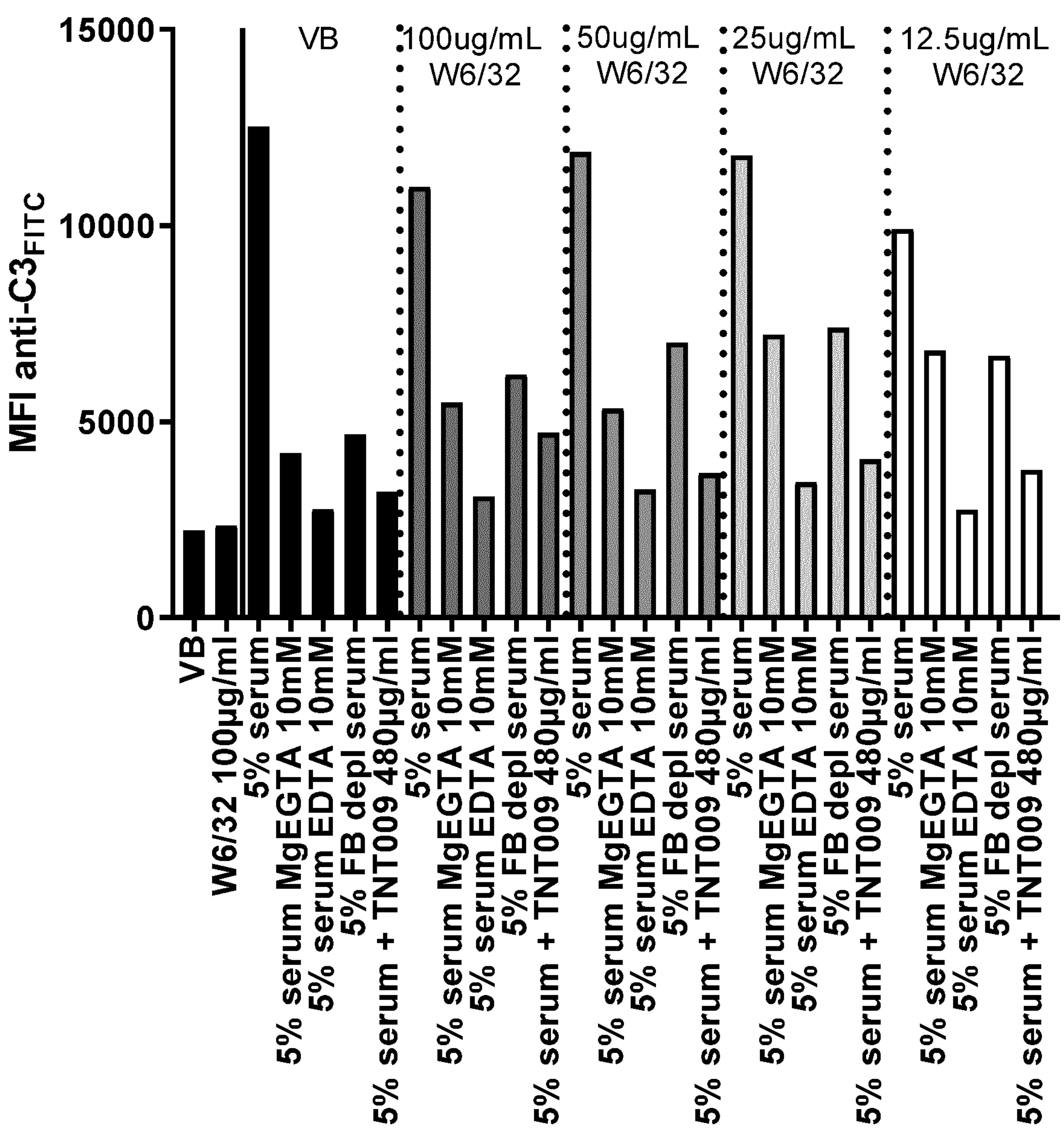

FIG. 5 shows complement C3 fixation on sNF02.2 Schwann cells by anti-HLA mAbs. Cells were opsonized with increasing concentrations of W6/32 (anti-HLA antibody) prior to addition of HPS (human pooled serum) to activate the complement pathway. Both EDTA and TNT009 (480 μg/mL) were added to assess complement specificity.

Figure 6:
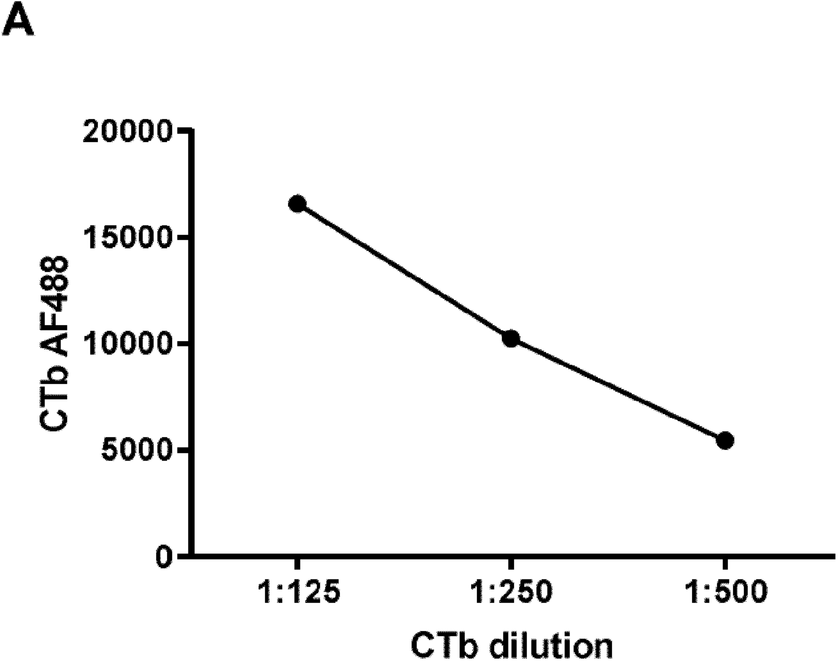
Figure 6:
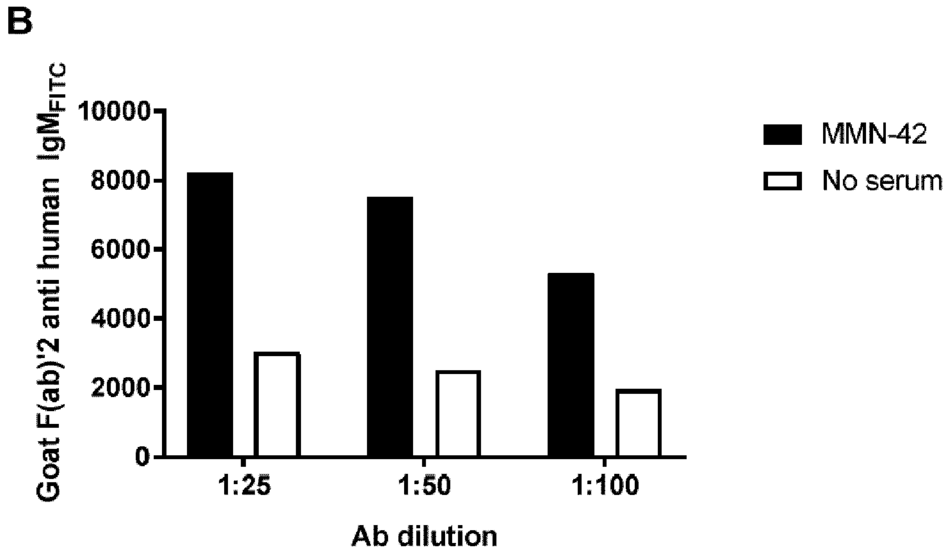

FIG. 6 shows GM1 expression and IgM binding on Schwann cells. (A) sNF02.2 Schwann cells were stained with CTb to detect GM1 expression using flow cytometry. (B) Flow cytometric detection of IgM binding to cultured sNF02.2 Schwann cells after opsonization with MMN-patient serum (shaded bars) or without activation of complement (white bars).

Figure 7:
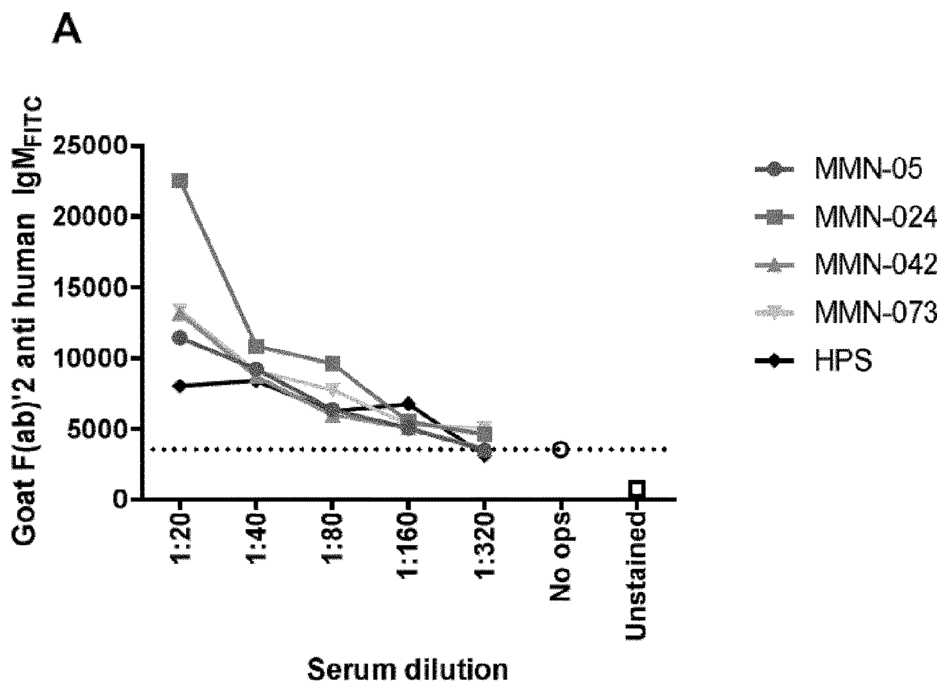
Figure 7:
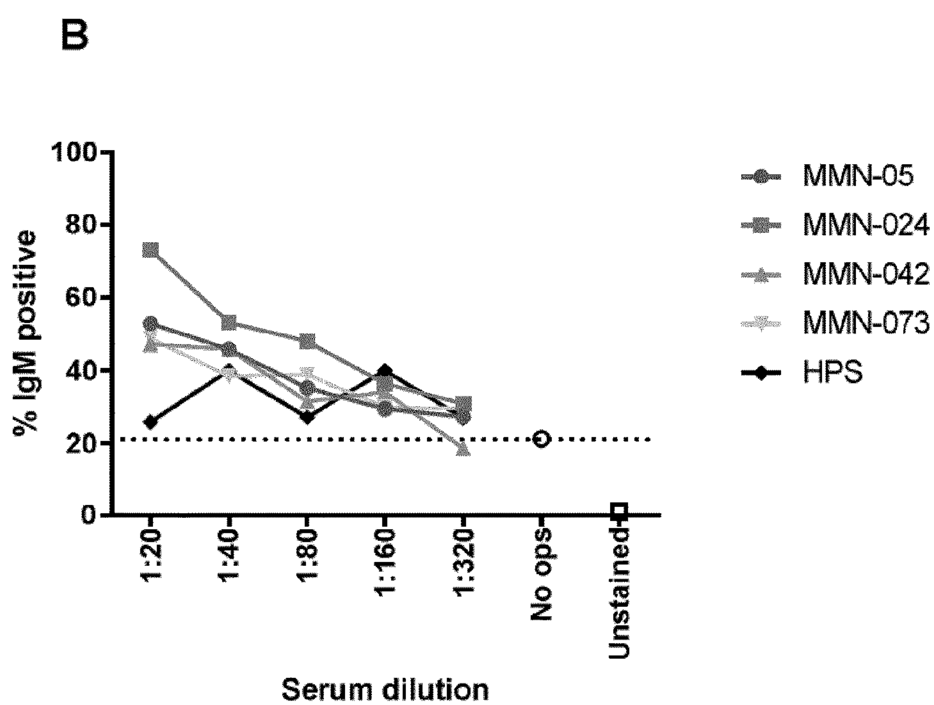

FIG. 7 shows binding of IgM in MMN-patient serum to sNF02.2 Schwann cells. Schwann cells were opsonized with different patient samples, containing various GM1 titres and all showed IgM binding upon incubation with sNF02.2 cells. (A) MFI of IgM staining (B) Percentage of IgM positive Schwann cells.

Figure 8:
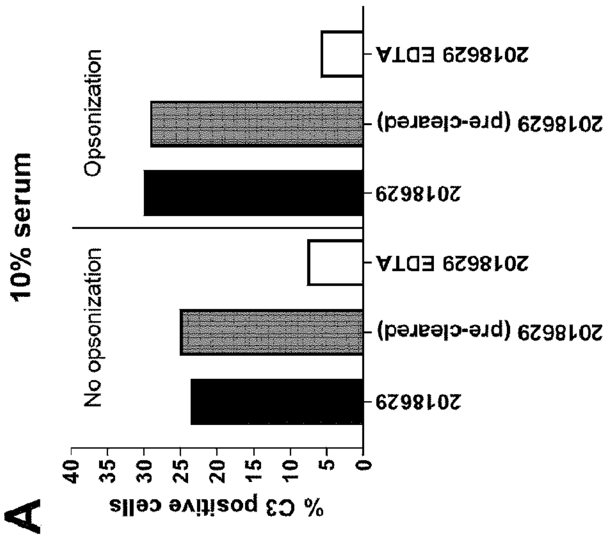
Figure 8:
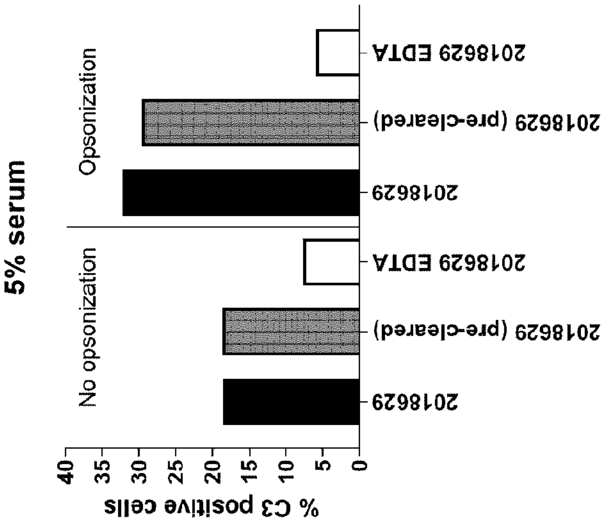
Figure 8:
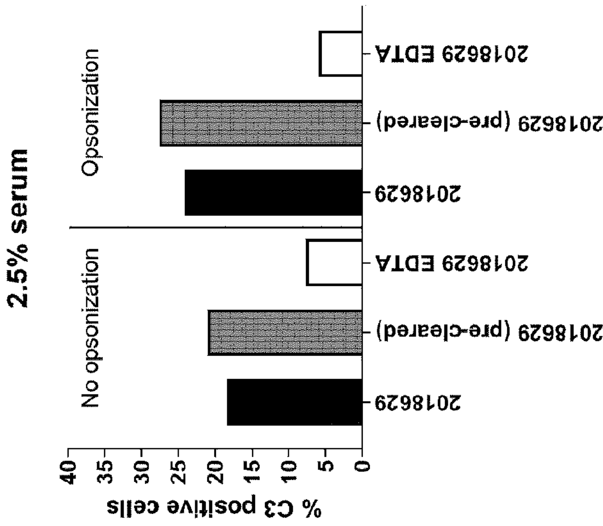
Figure 8:
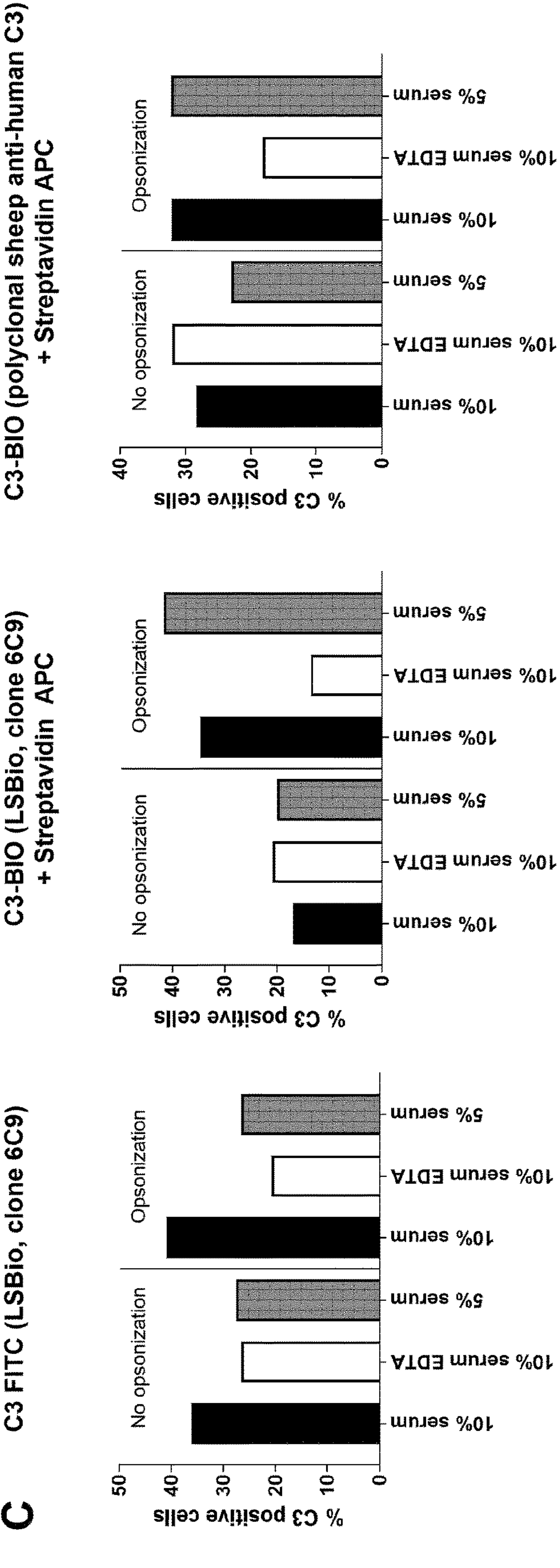

FIG. 8 shows optimization of C3 fixation on sNF02.2 Schwann cells after opsonization with MMN-patient serum. 50,000 Schwann cells were seeded into 96-well plates and opsonized with MMN-patient serum (1 h, RT). Each of the graphs of FIG. 8 shows 'no opsonization' on the left half of the graph and 'opsonization' on the right half of the graph. (A) Complement was activated using different percentages of complement active serum: 10% (left graph), 5% (middle graph) or 2.5% (right graph). Complement active serum (black bars) versus cleared serum (=complement active serum previously incubated with Schwann cells) (gray bars) was investigated. (B) Summary of results depicted in (A) comparing serum (black bars) versus cleared serum (light gray bars). (C) C3 fixation on Schwann cells using different C3 detection antibodies: C3 FITC (LSBio, clone 6C9) (left graph), C3-BIO (LSBio, clone 6C9)+Streptavidin APC (middle graph) or C3-BIO (polyclonal sheep anti-human C3)+Streptavidin APC (right graph). Cells were activated with either 10% (black bars) or 5% (gray bars) serum. White bars represent EDTA controls and were all as expected.

Figure 9:
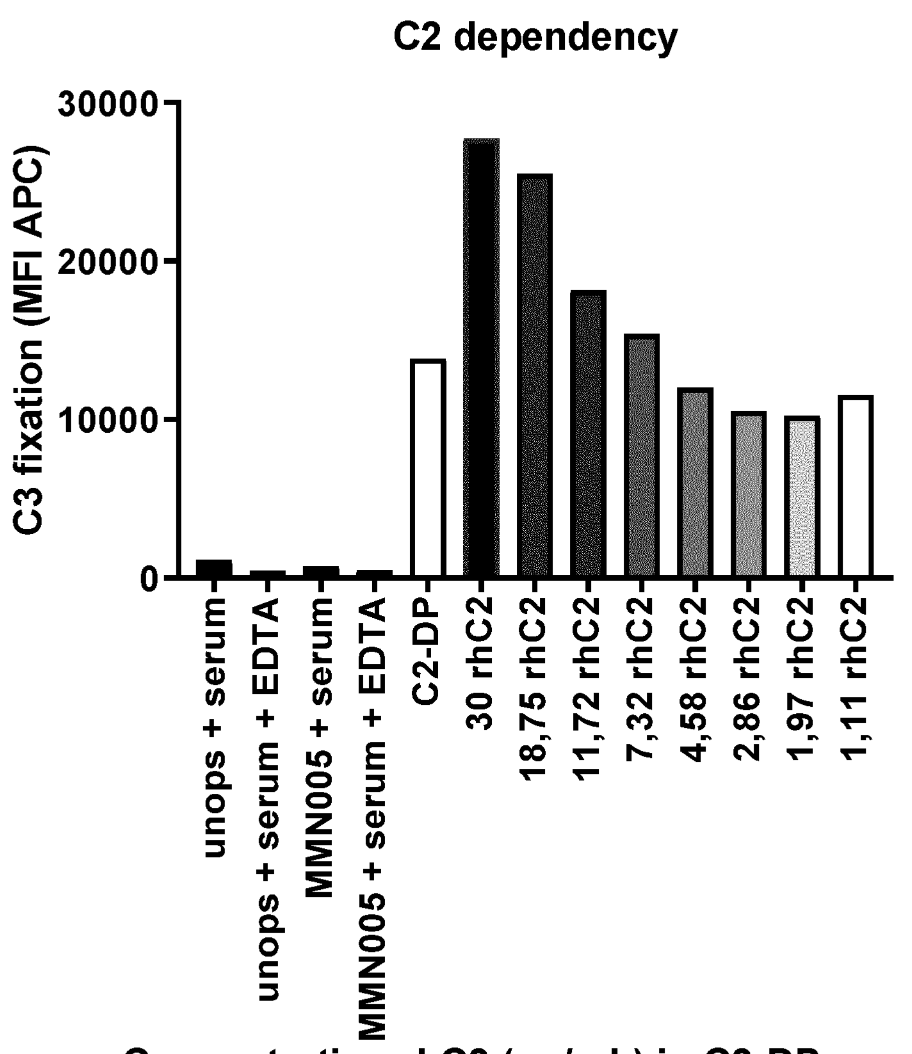

FIG. 9 shows C2 dependency of complement activation in Schwann cells. Schwann cells were seeded into 96-well plates and opsonized with MMN-patient serum (MMN-005) (1 h, RT) followed by incubation with C2-depleted serum supplemented with increasing concentrations of rhC2, starting at 1.11 μg/mL up to 30 μg/mL (physiological concentration). After 1 h (37° C.), C3 fixation was measured using flow cytometry, after staining with C3-BIO (LSBio, clone 6C9).

Figure 10:
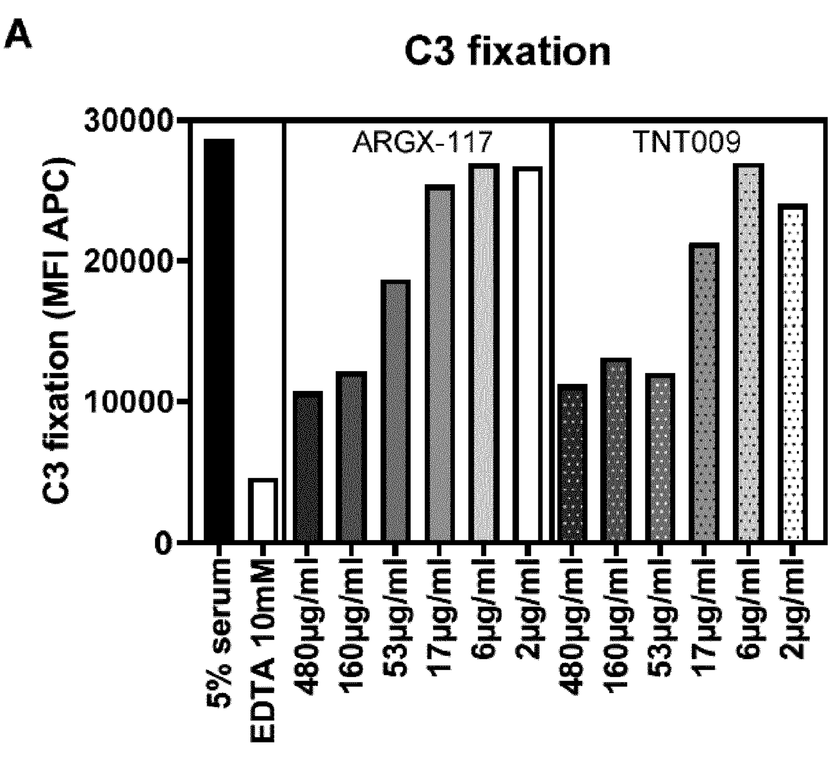
Figure 10:
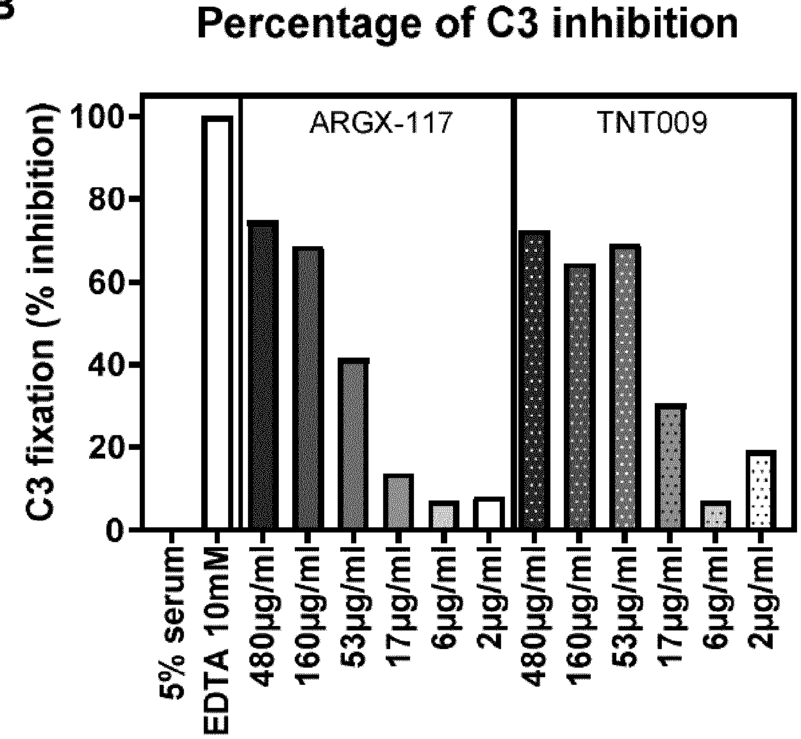

FIG. 10 shows dose-dependent inhibition of C3 fixation on sNF02.2 Schwann cells opsonized with MMN-patient serum by ARGX-117. Schwann cells were transferred to a 96-well plate (50,000 cells/well), opsonized with MMN-patient serum (1 h, RT) and subsequently incubated with 5% complement active serum which was pre-incubated with complement blocking antibodies or EDTA (20 min, RT). Detection of C3-fixation was performed by staining Schwann cells with C3-BIO (LSBio, clone 6C9) and streptavidin-APC. (A) C3 fixation on Schwann cells by MFI values of APC. (B) Percentage inhibition of C3 fixation on Schwann cells calculated with 5% serum set at zero % inhibition and EDTA 10 mM set as 100% inhibition.

Figure 11:
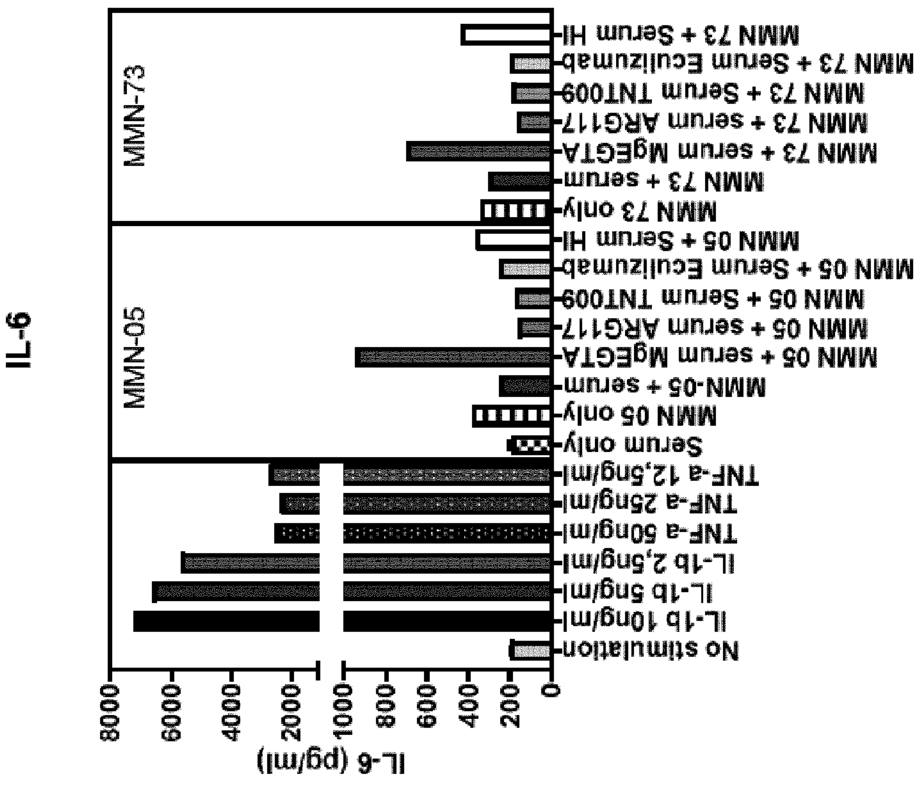
Figure 11:
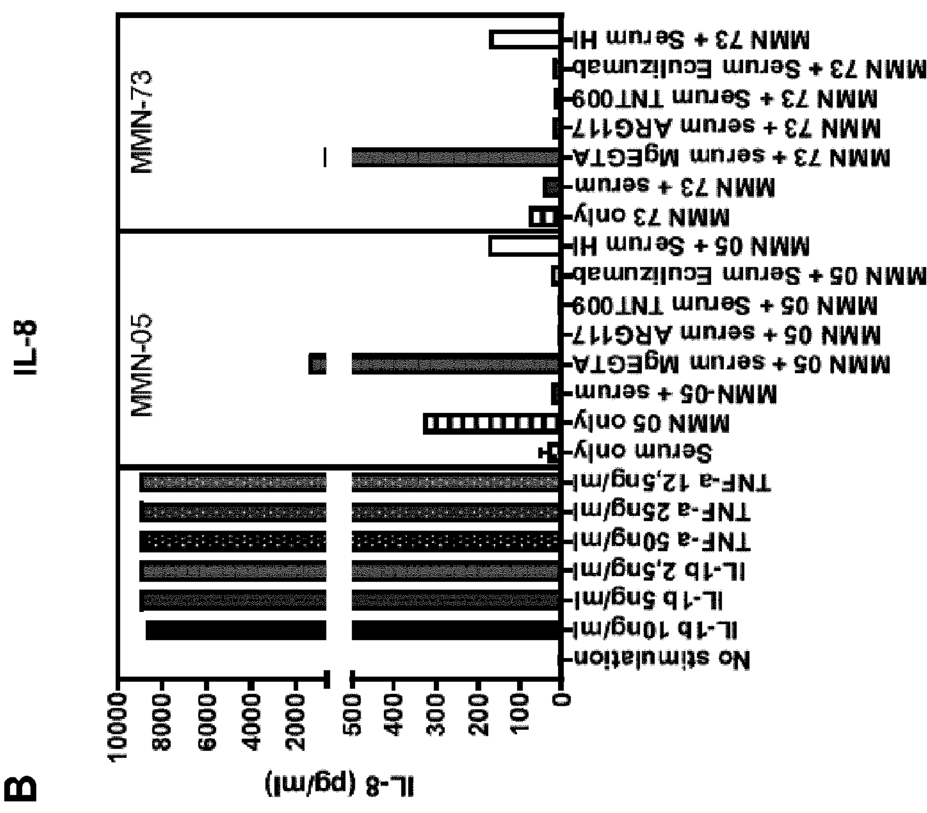
Figure 11:
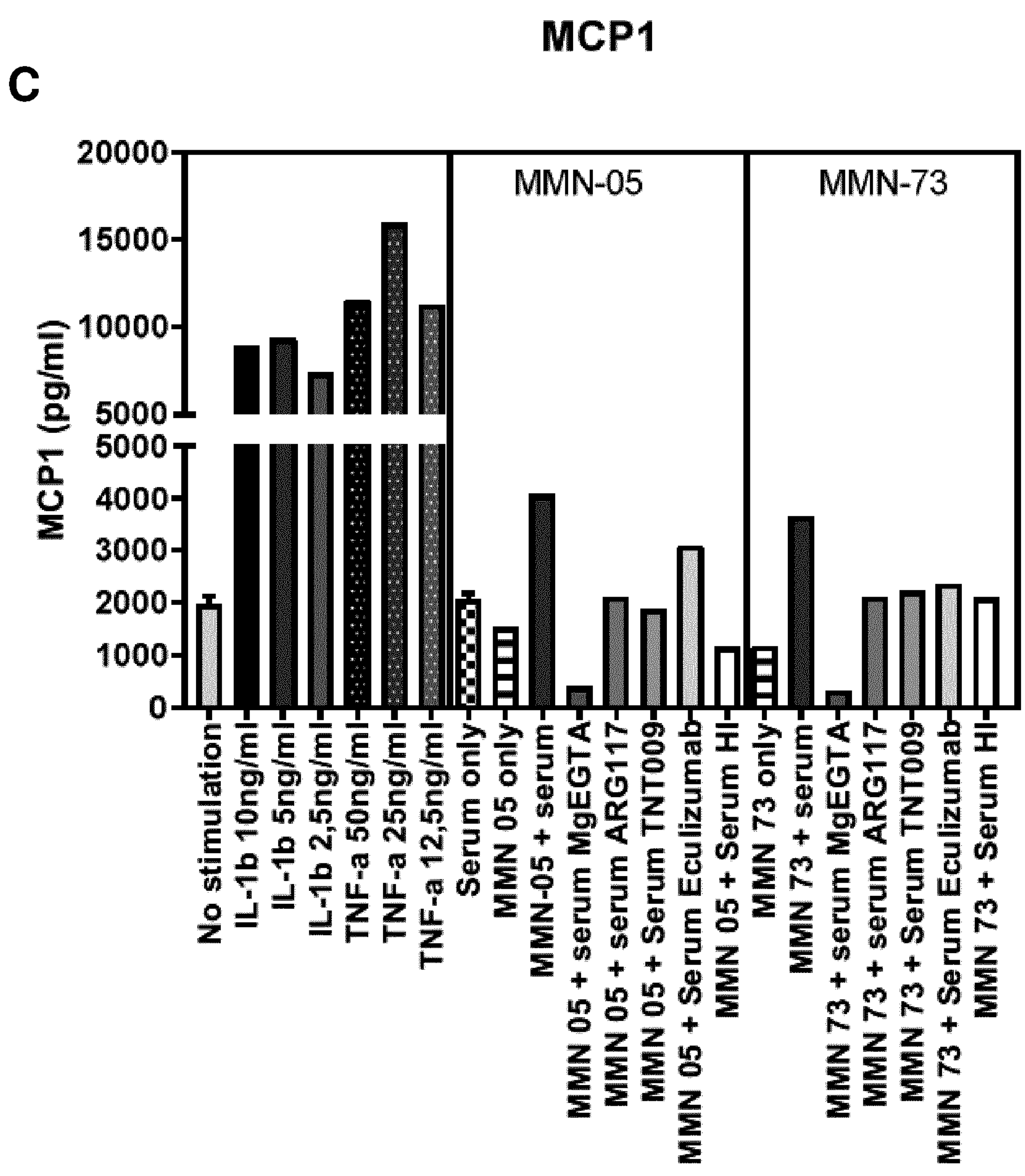

FIG. 11 shows cytokine secretion by sNF02.2 Schwann cells after complement activation induced by MMN sera. Schwann cells were seeded into 24-well plates, opsonized with MMN-patient serum (1 h, RT) and complement active serum was added in the presence or absence of complement blocking antibodies. After 48 h supernatant was collected and cytokine secretion was measured using Luminex platform. The three graphs show the following: (A) IL-6, (B) IL-8, and (C) MCP-1. Each of the graphs of FIG. 11 shows the bars in the following order (from left to right): no stimulation, IL-1b 10 ng/mL, IL-1b 5 ng/mL, IL-1b 2.5 ng/mL, TNF-α 50 ng/mL, TNF-α 25 ng/mL, TNF-α 12.5 ng/mL, serum only, MMN-05 only, MMN-05+serum, MMN-05+serum MgEGTA, MMN-05+serum ARGX-117, MMN-05+serum TNT009, MMN-05+serum Eculizumab, MMN-05+serum HI, MMN-73 only, MMN-73+serum, MMN-73+serum MgEGTA, MMN-73+serum ARGX-117, MMN-73+serum+TNT009, MMN-73+serum Eculizumab, MMN-73+serum HI.

Figure 12:
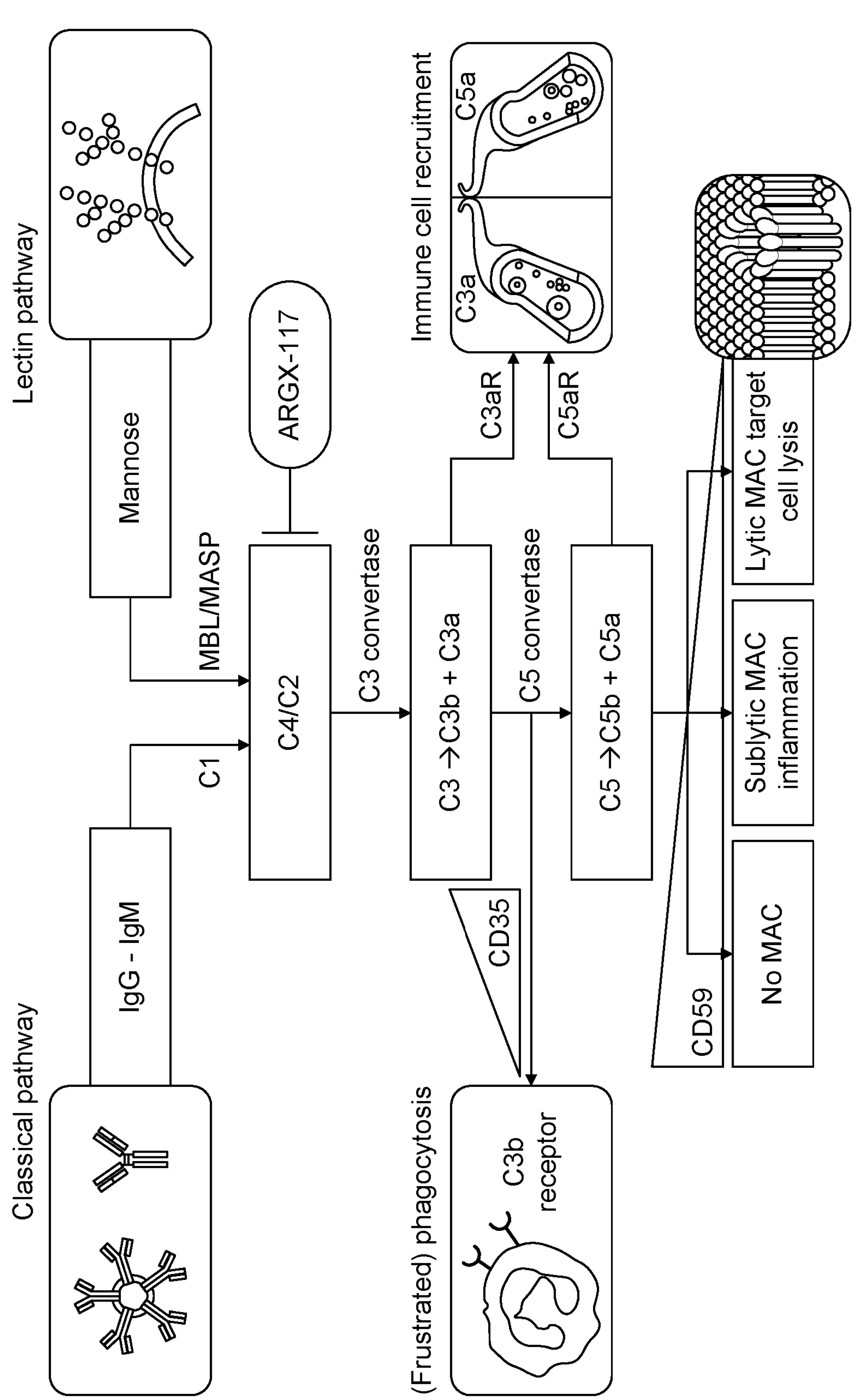

FIG. 12 shows a proposed mechanism of complement events triggered by anti-GM1 autoantibodies present in MMN patients.

Figure 13:
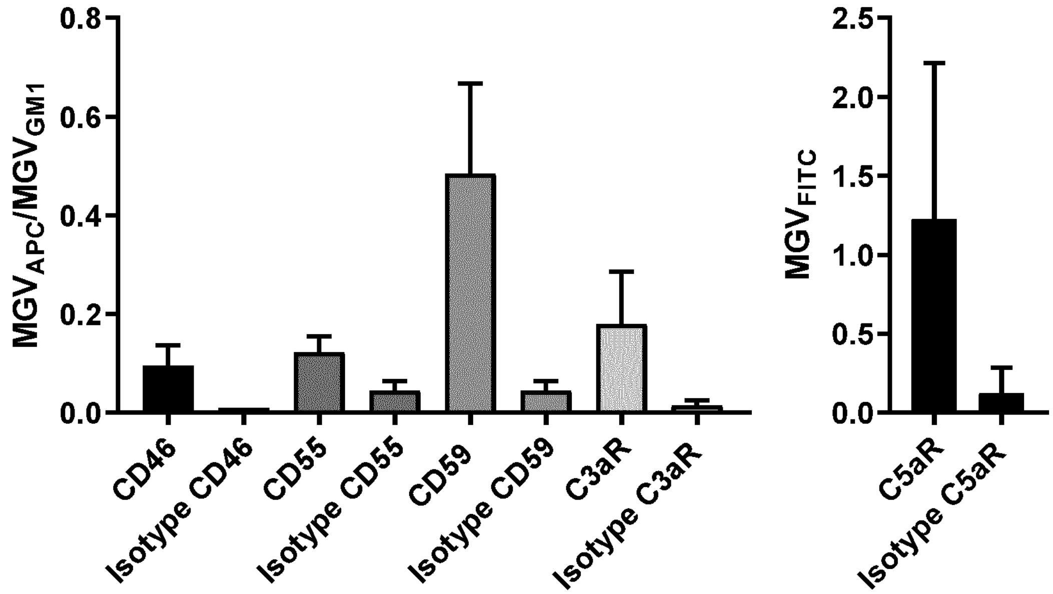

FIG. 13 shows expression of membrane complement proteins including complement regulatory proteins (CRPs) on fixed iPSC-MNs. Induced pluripotent stem cell-derived motor neurons (iPSC-MNs) were cultured and fixed using 4% PFA on coverslips prior to staining for expression markers. MGV=mean gray value.

Figure 14:
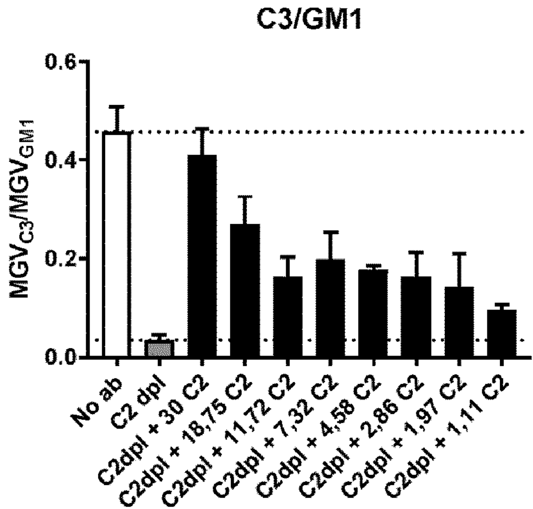
Figure 14:
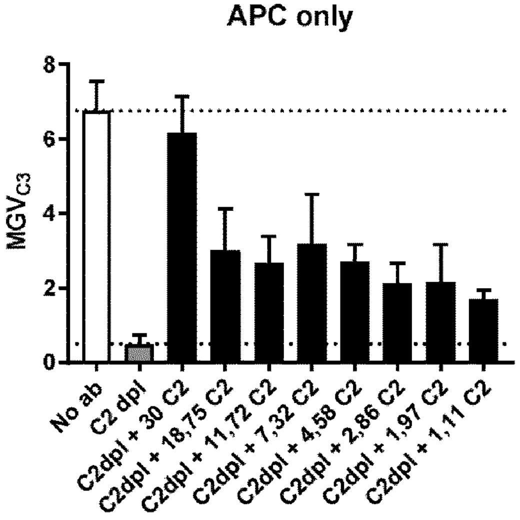
Figure 14:
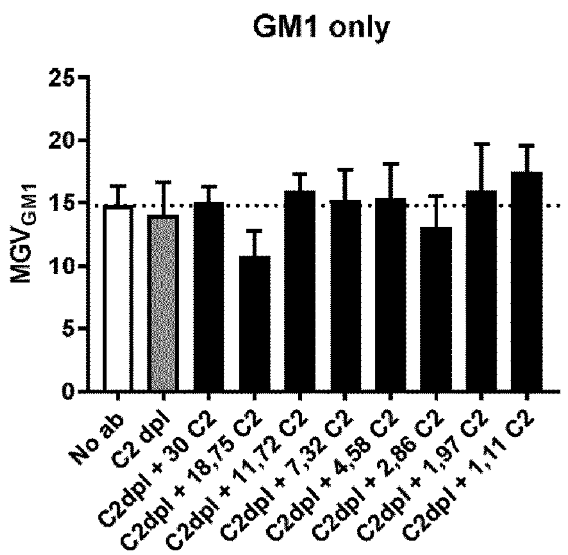

FIG. 14 shows C2 dependency of C3 fixation. iPSC-derived motor neurons were opsonized with C2-depleted serum and reconstituted with increasing concentrations of purified human C2 (hC2) to evaluate complement activation by measuring C3 fixation. iPSC-MNs were cultured for 3 days prior to fixation and subsequently stained to detect GM1 expression and C3 deposition. Images were analyzed at 40× magnification and the mean gray value (MGV) was calculated for GM1 alone, C3 alone or the ratio between the two.

Figure 15:
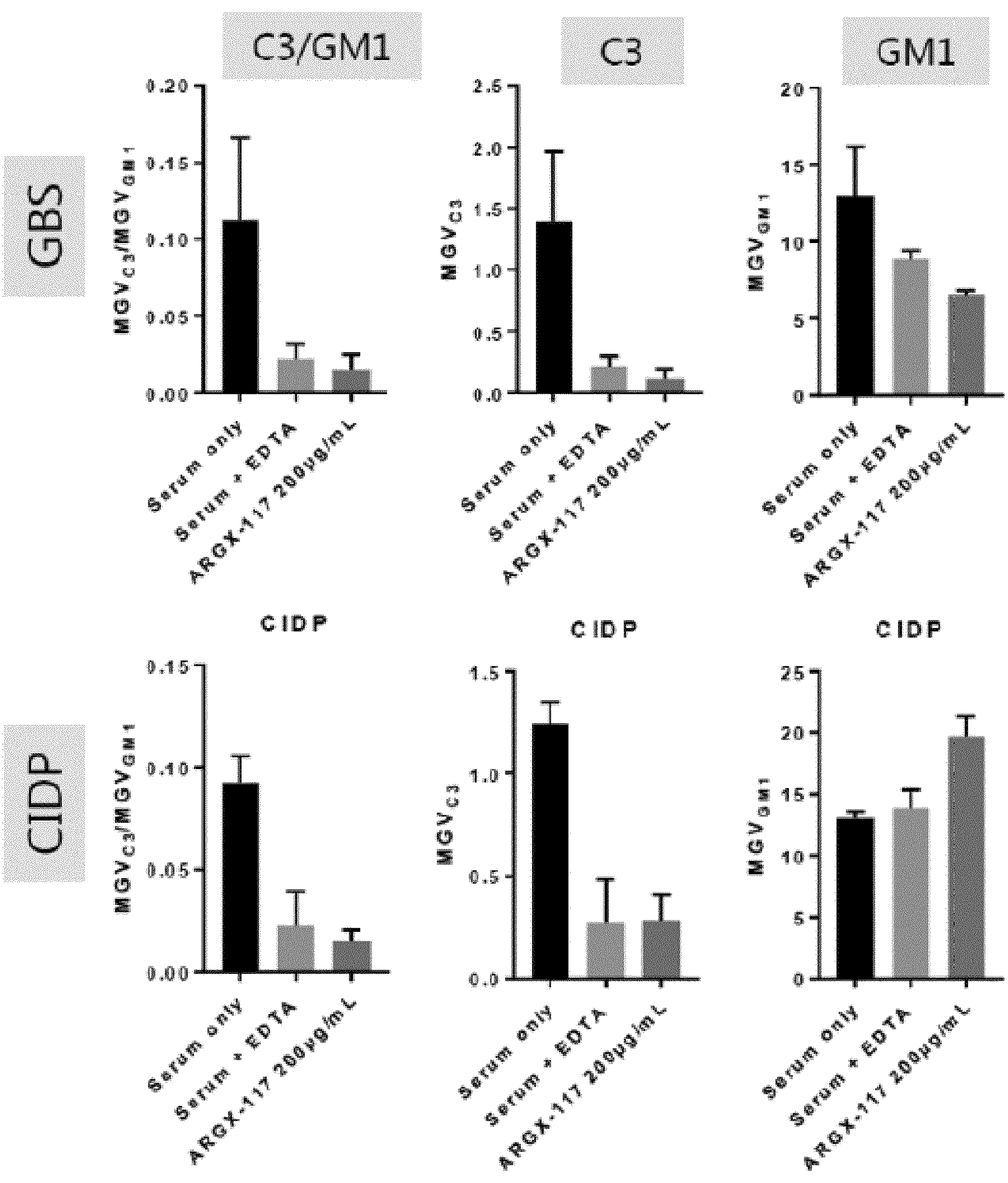

FIG. 15 shows that ARGX-117 blocked complement in other immune-mediated neuropathies. GBS or CIPD patient sera was used to opsonize the motor neurons in the presence or absence of ARGX-117 (200 μg/mL). iPSC derived motor neurons were cultured for 12-14 days prior to fixation and stained to detect GM1 expression and C3 deposition. Images were analyzed at 40× magnification and the mean gray value (MGV) was calculated for GM1 alone, C3 alone or the ratio between the two (C3/GM1). Each of the graphs of FIG. 15 compares 'serum only' (left bar), 'serum+EDTA' (middle bar) and 'ARGX-117 200 μg/mL' (right bar).

Figure 16:
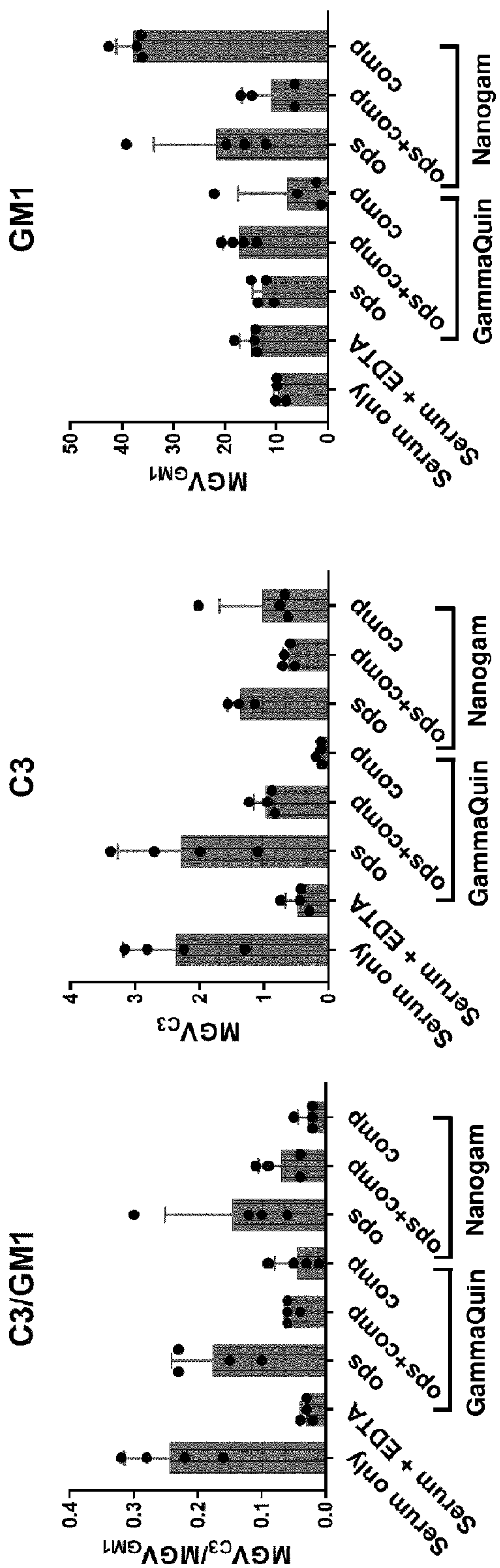

FIG. 16 shows the effects of IVIg on C3 fixation using iPSC-MNs opsonized with MMN patient sample. iPSC-derived motor neurons were cultured for 12-14 days prior to fixation and subsequently stained for GM-1 expression and C3 deposition. Two different IVIg batches were tested: GammaQuin and Nanogam both used at 50 mg/mL. Images were analyzed at 40× magnification and the mean gray value (MGV) was calculated for GM1 alone, C3 alone or the ratio between the two (C3/GM1). Each of the graphs of FIG. 16 shows bars in the following order (from left to right): serum only, serum+EDTA, GammaQuin ops, GammaQuin ops+comp, GammaQuin comp, Nanogram ops, Nanogram ops+comp, Nanogram comp.

Figure 17:
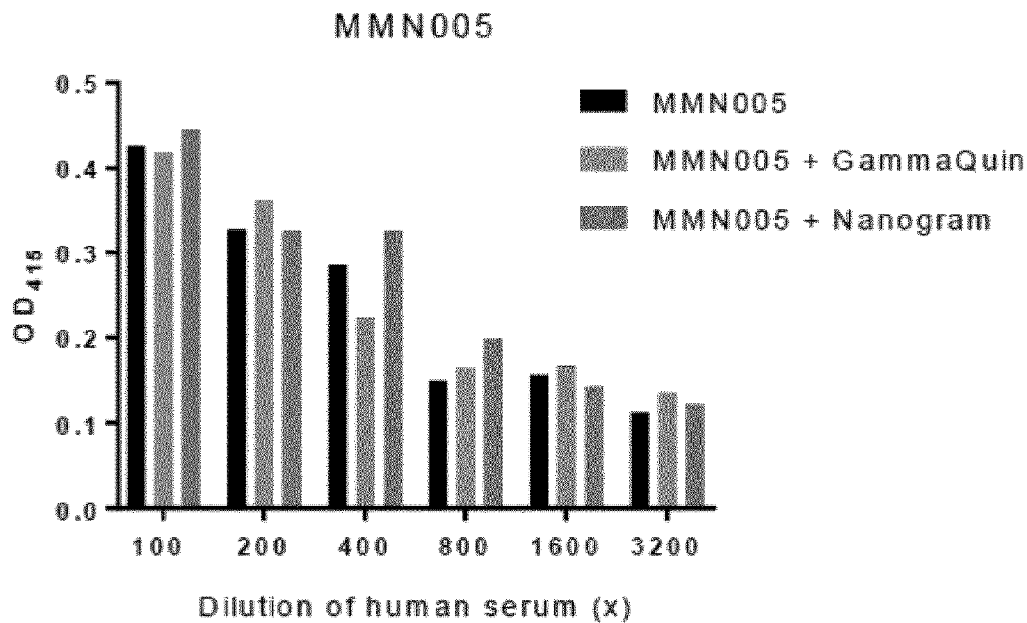
Figure 17:
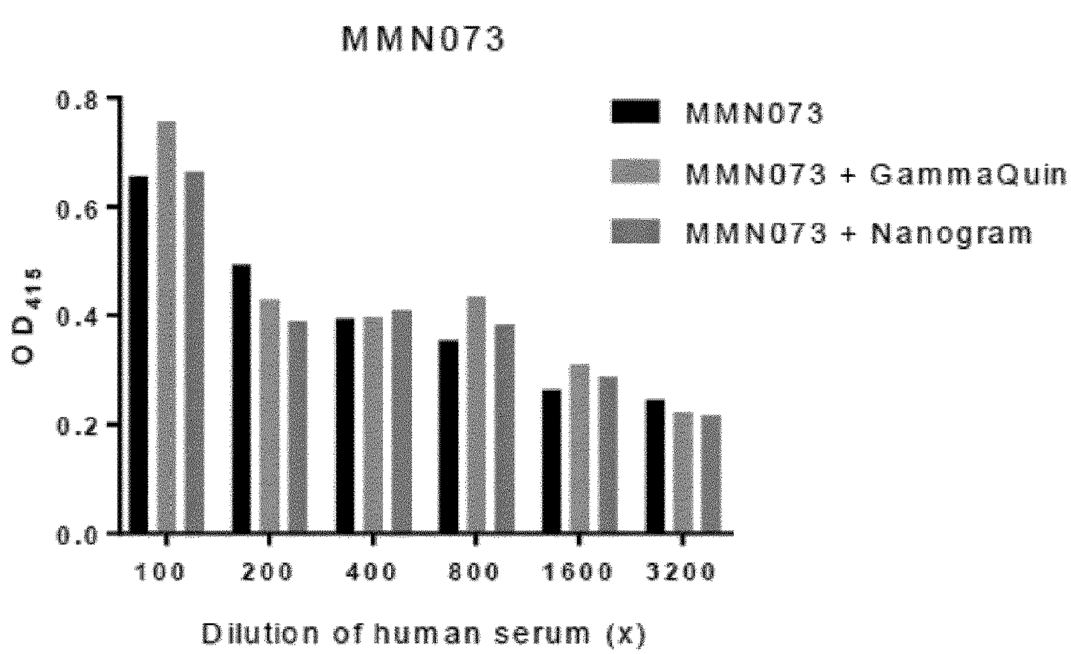

FIG. 17 shows the anti-idiotypic effect of IVIg on GM1 binding by MMN patient sera. ELISA was performed with MMN patient sera, MMN005 and MMN073. GM1 was coated on a 96-well plate, incubated with MMN-patient sera with or without addition of 50 μg/mL IVIg (2 batches: GammaQuin and Nanogam) prior to detection of IgM using an anti-human IgM antibody.

DETAILED DESCRIPTION

A. Definitions

Unless defined otherwise, all technical and scientific terms used herein have the same meaning as commonly understood by the ordinary person skilled in the art to which the invention pertains.

Without limiting any term, further clarifications of some of the terms used herein are provided below.

"Paraproteinemic neuropathy"—as used herein, the term "paraproteinemic neuropathy" or "PPN" describes a set of peripheral neuropathies characterised by the presence of homogeneous immunoglobulin in the serum. The homogeneous immunoglobulin is known as "paraprotein". An abnormal clonal proliferation of B-lymphocytes or plasma cells, which may or may not occur in the context of a hematologic malignancy, produces the immunoglobulins in excess. Several disorders of the peripheral nervous system are closely associated with the presence of excessive amounts of abnormal immunoglobulins in the blood. PPN may be caused by the interaction of antibodies with specific antigenic targets on peripheral nerves or by the deposition of the immunoglobulins. Exemplary paraproteinemic neuropathies that may be treated in accordance with the invention include MMN, CIDP, and GBS.

"Multifocal motor neuropathy"—Multifocal motor neuropathy or MMN is a rare disorder with a prevalence of around 0.6 per 100,000 individuals, with men more frequently affected than women (ratio of 2.7:1) (Harschnitz et al., *J Clin Immunol* 2014, 34:112-119). MMN is a chronic, immune-mediated neuropathy, characterised by asymmetric predominantly distal weakness of limbs. The hallmark of the disease is the presence of multi-focal motor conduction blocks, and patients often show high serum levels of IgM antibodies against the glycosphingolipid GM1, which is abundantly expressed in peri-nodal regions of peripheral nerves. These auto-GM1 IgM antibodies have complement activating properties and are determinants of disease severity (Vlam et al., *Neurol Neuroimmunol Neuroinflamm* 2015, 25; 2(4)). GM1 is abundantly expressed in peripheral motor nerves and localizes to both the axolemma and myelin of peripheral nerves. GM1 has several important functions necessary for action potential propagation and maintenance of conduction velocity. Highest GM1 expression is found at the node of Ranvier and on adjacent paranodes, where it anchors potassium channels and clusters sodium channels to maintain tightjunctions through paranodal stabilization. Moreover, GM1 functions both as a receptor modulator of neurotrophic factors controlling neuritogenesis and apoptosis, and as part of multi-molecular assemblies in lipid rafts in membrane signaling and trafficking. Disruption of these functions results in a failure of conduction across paranodal areas. The anti-GM1 IgM antibodies present in MMN patients are produced by activated B cells (plasma cells); however, the mechanism of this B cell activation is not yet established.

"Guillain-Barré syndrome"—Guillain-Barre syndrome or GBS has an incidence of 0.81-1.89 cases per 100,000 individuals, with men more frequently affected than women (ratio of 3:2) (Kieseier et al., Nature Reviews, 2018, 4:31). In 60-70% of cases, the first symptoms of GBS manifest between 1 and 3 weeks after an acute infection, usually an upper respiratory tract infection or gastrointestinal infection. The initial symptoms of GBS are typically changes in sensation or pain, together with muscle weakness, beginning in the feet and hands. This often spreads to the arms and upper body. Autoantibodies to various gangliosides found in axons are used to aid diagnosis of certain subtypes of GBS. For example, anti-GM1 and anti-GD1a IgG antibodies are found in the serum of patients suffering from acute motor axonal neuropathy (AMAN) and acute motor and sensory axonal neuropathy (AMSAN). These antibodies bind to the nodes of Ranvier, where they disrupt the fine structural arrangements responsible for sodium channel clustering, leading to slowed axonal conduction and loss of function. Alternatively, the antibodies bind to the motor nerve terminals causing degeneration of the presynaptic nerve terminal.

"Chronic inflammatory demyelinating polyneuropathy"—Chronic Inflammatory demyelinating polyneuropathy or CIDP is the most common immune-mediated neuropathy, with a reported prevalence ranging from 0.8-8.9 cases per 100,000 individuals (Kieseier et al., Nature Reviews, 2018, 4:31). Men are more frequently affected than women (ratio of 2:1). CIDP is closely related to GBS and it is considered the chronic counterpart of the acute disease. The most common symptoms of CIDP are weakness, numbness, and tingling in the legs, arms, fingers, and hands. Other symptoms include fatigue, pain, balance issues, and impairment of the ability to walk. Some variants of CIDP present autoimmunity against proteins at the node of Ranvier. These variants comprise a subgroup of inflammatory neuropathies with IgG4 autoantibodies against the paranodal proteins neurofascin-186, neurofascin-155, contactin-1 and caspr-1 (Querol et al., *Nat Rev Neurol.* 2017, 13(9):533-547). These proteins play a pivotal role in the compartmentalisation of the myelinated axon into the node, paranode, and internode. Compartmentalisation is required for saltatory conduction as it maintains segregation of the voltage-gated sodium and potassium channels involved in the transmission of action potentials. Disruption of these regions can result in slowed or blocked nerve conduction.

"Antagonist of the complement system"—as used herein, the phrase "antagonist of the complement system" or "complement antagonist" refers to any agent capable of blocking or inhibiting the function of a complement factor or component of the complement cascade, thereby inhibiting or reducing complement activity. The antagonist of the complement system may block or inhibit the classical complement pathway, the lectin complement pathway, the alternative complement pathway, or any combination thereof. Preferably, the antagonist of the complement system inhibits the classical complement pathway and the lectin complement pathway by targeting a complement factor that is common to both of these pathways. The complement antagonist for use according to the methods described herein inhibits the complement system upstream of complement factor C5. This means that the antagonist inhibits or reduces complement activity by inhibiting any component or factor of the complement pathway preceding C5 in the complement cascade i.e. the antagonist does not inhibit C5 directly or any complement factors downstream of C5. For example, the antagonist may inhibit the function of complement factor C1, C2, C3 or C4, or any combination thereof. Inhibiting the function of a complement factor means that the complement factor is prevented from performing its role in the overall cascade of complement activation even when in the presence of its upstream activation signal.

The antagonists for use in the present invention may take the form of any suitable agent and may block or inhibit the function of a complement factor or component directly or indirectly. The antagonist may inhibit the function of its target by down-regulating the expression of the target such as by siRNA technology. In this regard, suitable antagonists include inhibitory RNA species, for example siRNAs or shRNAs. The antagonist may inhibit the function of its target by binding directly to the target; for example, the antagonist may bind directly to its target and prevent it from activating the next complement factor in the cascade. In preferred embodiments, the antagonist is specific for its target. For example, an antagonist of C2 will preferentially inhibit the function of C2 as compared with other molecular targets. The antagonists will typically achieve the required level of specificity by interacting directly with their target, for example, by selectively binding to a complement protein. Suitable agents that may serve as antagonists for use in the methods described herein include but are not limited to: small molecule inhibitors; and biological antagonists including inhibitory peptides, antibody mimetics such as affibodies, affilins, affitins, adnectins, atrimers, evasins, DARPins, anticalins, avimers, fynomers, versabodies and duocalins. In preferred embodiments, the antagonists for use in the present invention are antibodies or antigen-binding fragments thereof.

"Antibody" or "Immunoglobulin"—As used herein, the term "immunoglobulin" includes a polypeptide having a combination of two heavy and two light chains whether or not it possesses any relevant specific immunoreactivity. "Antibodies" refer to such assemblies which have significant known specific immunoreactive activity to an antigen of interest. Antibodies and immunoglobulins comprise light and heavy chains, with or without an interchain covalent linkage between them. Basic immunoglobulin structures in vertebrate systems are relatively well understood.

The generic term "immunoglobulin" comprises five distinct classes of antibody that can be distinguished biochemically. With regard to IgG, immunoglobulins comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region. The light chains of an antibody are classified as either kappa or lambda (κ,λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA, IgD or IgE, respectively. The immunoglobulin subclasses (isotypes) e.g., IgG1, IgG2, IgG3, IgG4, IgA1, etc. are well characterised and are known to confer functional specialization. Modified versions of each of these classes and isotypes are readily discernible to the skilled artisan in view of the instant disclosure and, accordingly, are within the scope of the instant invention.

As indicated above, the variable region of an antibody allows the antibody to selectively recognize and specifically bind epitopes on antigens. That is, the VL domain and VH domain of an antibody combine to form the variable region that defines a three-dimensional antigen binding site. This quaternary antibody structure forms the antigen binding site present at the end of each arm of the Y. More specifically, the antigen binding site is defined by three complementary determining regions (CDRs) on each of the VH and VL chains.

The term "antibody" as used herein is also intended to encompass "VHH antibodies" or "Heavy-chain only antibodies".

"VHH antibodies"—As used herein the term "VHH antibody" or "heavy-chain only antibody" refers to a type of antibody produced only by species of the Camelidae family, which includes camels, llama, and alpaca. Heavy chain-only antibodies or VHH antibodies are composed of two heavy chains and are devoid of light chains. Each heavy chain has a variable domain at the N-terminus, and these variable domains are referred to as "VHH" domains in order to distinguish them from the variable domains of the heavy chains of the conventional heterotetrameric antibodies i.e. the VH domains, described above.

"Variable region" or "variable domain"—the terms "variable region" and "variable domain" are used herein interchangeably and are intended to have equivalent meaning. The term "variable" refers to the fact that certain portions of the variable domains VH and VL differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the VL domain and the VH domain which form part of the antigen binding site. The first, second and third hypervariable loops of the VLambda light chain domain are referred to herein as L1 (λ), L2(λ) and L3(λ) and may be defined as comprising residues 24-33 (L1 (λ), consisting of 9, 10 or 11 amino acid residues), 49-53 (L2(λ), consisting of 3 residues) and 90-96 (L3(λ), consisting of 5 residues) in the VL domain (Morea et al., Methods 20:267-279 (2000)). The first, second and third hypervariable loops of the VKappa light chain domain are referred to herein as L1(κ), L2(κ) and L3(κ) and may be defined as comprising residues 25-33 (L1 (K), consisting of 6, 7, 8, 11, 12 or 13 residues), 49-53 (L2(κ), consisting of 3 residues) and 90-97 (L3(κ), consisting of 6 residues) in the VL domain (Morea et al., Methods 20:267-279 (2000)). The first, second and third hypervariable loops of the VH domain are referred to herein as H1, H2 and H3 and may be defined as comprising residues 25-33 (H1, consisting of 7, 8 or 9 residues), 52-56 (H2, consisting of 3 or 4 residues) and 91-105 (H3, highly variable in length) in the VH domain (Morea et al., Methods 20:267-279 (2000)).

Unless otherwise indicated, the terms L1, L2 and L3 respectively refer to the first, second and third hypervariable loops of a VL domain, and encompass hypervariable loops obtained from both Vkappa and Vlambda isotypes. The terms H1, H2 and H3 respectively refer to the first, second and third hypervariable loops of the VH domain, and encompass hypervariable loops obtained from any of the known heavy chain isotypes, including γ, ε, δ, α or μ.

The hypervariable loops L1, L2, L3, H1, H2 and H3 may each comprise part of a "complementarity determining region" or "CDR", as defined below. The terms "hypervariable loop" and "complementarity determining region" are not strictly synonymous, since the hypervariable loops (HVs) are defined on the basis of structure, whereas complementarity determining regions (CDRs) are defined based on sequence variability (Kabat et al., Sequences of Proteins of Immunological Interest, 5th Ed. Public Health Service, National Institutes of Health, Bethesda, MD., 1983) and the limits of the HVs and the CDRs may be different in some VH and VL domains.

The CDRs of the VL and VH domains can typically be defined as comprising the following amino acids: residues 24-34 (LCDR1), 50-56 (LCDR2) and 89-97 (LCDR3) in the light chain variable domain, and residues 31-35 or 31-35b (HCDR1), 50-65 (HCDR2) and 95-102 (HCDR3) in the heavy chain variable domain; (Kabat et al., Sequences of Proteins of Immunological Interest, 5th Ed. Public Health Service, National Institutes of Health, Bethesda, MD. (1991)). Thus, the HVs may be comprised within the corresponding CDRs and references herein to the "hypervariable loops" of VH and VL domains should be interpreted as also encompassing the corresponding CDRs, and vice versa, unless otherwise indicated.

The more highly conserved portions of variable domains are called the framework region (FR), as defined below. The variable domains of native heavy and light chains each comprise four FRs (FR1, FR2, FR3 and FR4, respectively), largely adopting a β-sheet configuration, connected by the three hypervariable loops. The hypervariable loops in each chain are held together in close proximity by the FRs and, with the hypervariable loops from the other chain, contribute to the formation of the antigen binding site of antibodies. Structural analysis of antibodies revealed the relationship between the sequence and the shape of the binding site formed by the complementarity determining regions (Chothia et al., J. Mol. Biol. 227: 799-817 (1992)); Tramontano et al., J. Mol. Biol, 215:175-182 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

"CDR"—as used herein, the term "CDR" or "complementarity determining region" means the non-contiguous antigen binding sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat based on sequence comparisons.

TABLE 1

CDR definitions

| | CDR Definitions | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra "Framework region"—The term "framework region" or "FR region" as used herein, includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable domain and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light chain variable region CDRs. Similarly, using the definition of CDRs by Chothia et al. or McCallum et al. the framework region boundaries are separated by the respective CDR termini as described above. In preferred embodiments the CDRs are as defined by Kabat.

In naturally occurring antibodies, the six CDRs present on each monomeric antibody are short, non-contiguous sequences of amino acids that are specifically positioned to form the antigen binding site as the antibody assumes its three-dimensional configuration in an aqueous environment. The remainder of the heavy and light variable domains show less inter-molecular variability in amino acid sequence and are termed the framework regions. The framework regions largely adopt a 3-sheet conformation and the CDRs form loops which connect, and in some cases form part of, the 3-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

"Constant region"—As used herein, the term "constant region" refers to the portion of the antibody outside of the variable domains or variable regions. Immunoglobulin light chains have a single domain "constant region", typically referred to as the "CL or CL1 domain". This domain lies C terminal to the VL domain. Immunoglobulin heavy chains differ in their constant region depending on the class of immunoglobulin (γ, μ, α, δ, ε). Heavy chains γ, α and δ have a constant region consisting of three immunoglobulin domains (referred to as CH1, CH2 and CH3) with a flexible hinge region separating the CH1 and CH2 domains. Heavy chains μ and ε have a constant region consisting of four domains (CH1-CH4). The constant domains of the heavy chain are positioned C terminal to the VH domain.

The numbering of the amino acids in the heavy and light immunoglobulin chains run from the N-terminus at the forked ends of the Y configuration to the C-terminus at the bottom of each chain. Different numbering schemes are used to define the constant domains of the immunoglobulin heavy and light chains. In accordance with the EU numbering scheme, the heavy chain constant domains of an IgG molecule are identified as follows: CH1-amino acid residues 118-215; CH2-amino acid residues 231-340; CH3-amino acid residues 341-446. In accordance with the Kabat numbering scheme, the heavy chain constant domains of an IgG molecule are identified as follows: CH1-amino acid residues 114-223; CH2-amino acid residues 244-360; CH3-amino acid residues 361-477. The "Fc domain" or "Fc region" typically defines the portion of the constant region of a heavy chain including the CH2 and CH3 domains. The Fc region may also include some residues from the hinge region. The "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux K. H. et al. J. Immunol. 161:4083-90 1998). Antibodies of the invention comprising a "fully human" hinge region may contain one of the hinge region sequences shown in Table 2 below.

TABLE 2

Human hinge sequences

| IgG | Upper hinge | Middle hinge | Lower hinge |
|---|---|---|---|
| IgG1 | EPKSCDKTHT (SEQ ID NO: 21) | CPPCP (SEQ ID NO: 22) | APELLGGP (SEQ ID NO: 23) |
| IgG3 | ELKTPLGDTTHT (SEQ ID NO: 24) | CPRCP (EPKSCDTPPPCPRCP)$_3$ (SEQ ID NO: 25) | APELLGGP (SEQ ID NO: 23) |
| IgG4 | ESKYGPP (SEQ ID NO: 26) | CPSCP (SEQ ID NO: 27) | APEFLGGP (SEQ ID NO: 28) |
| IgG2 | ERK (SEQ ID NO: 29) | CCVECPPPCP (SEQ ID NO:30) | APPVAGP (SEQ ID NO: 31) |

"Fragment"—the term "fragment" or "antigen-binding fragment" refers to a part or portion of an antibody or antibody chain comprising fewer amino acid residues than an intact or complete antibody or antibody chain. The term "antigen-binding fragment" refers to a polypeptide fragment of an immunoglobulin or antibody that binds antigen or competes with intact antibody (i.e., with the intact antibody from which they were derived) for antigen binding. As used herein, the term "fragment" of an antibody molecule includes antigen binding fragments of antibodies, for example, an antibody light chain variable domain (VL), an antibody heavy chain variable domain (VH), a single chain antibody (scFv), a F(ab')2 fragment, a Fab fragment, an Fd fragment, an Fv fragment, a one-armed (monovalent) antibody, diabodies, triabodies, tetrabodies or any antigen binding molecule formed by combination, assembly or conjugation of such antigen binding fragments. The term "antigen-binding fragment" as used herein is further intended to encompass antibody fragments selected from the group consisting of unibodies, domain antibodies and nanobodies. Fragments can be obtained, e.g., via chemical or enzymatic treatment of an intact or complete antibody or antibody chain or by recombinant means.

"Specificity" and "Multispecific antibodies"—The antibodies for use in the methods described herein bind to target antigens within the complement system. It is preferred that the antibodies "specifically bind" to their target antigen, wherein the term "specifically bind" refers to the ability of any antibody to preferentially immunoreact with a given target e.g. C1, C2, C3 or C4. The antibodies may be monospecific and contain one or more binding sites which specifically bind a particular target. The antibodies may be incorporated into "multispecific antibody" formats, for example bispecific antibodies, wherein the multispecific antibody binds to two or more target antigens. In order to achieve multiple specificities, "multispecific antibodies" are typically engineered to include different combinations or pairings of heavy and light chain polypeptides with different VH-VL pairs. Multispecific, notably bispecific antibodies, may be engineered so as to adopt the overall conformation of a native antibody, for example a Y-shaped antibody having Fab arms of different specificities conjugated to an Fc region. Alternatively multispecific antibodies, for example bispecific antibodies, may be engineered so as to adopt a non-native conformation, for example wherein the variable domains or variable domain pairs having different specificities are positioned at opposite ends of the Fc region.

"Modified antibody"—As used herein, the term "modified antibody" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. scFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen). In another embodiment, a modified antibody of the invention is a fusion protein comprising at least one heavy chain portion lacking a CH2 domain and comprising a binding domain of a polypeptide comprising the binding portion of one member of a receptor ligand pair.

"Humanising substitutions"—As used herein, the term "humanising substitutions" refers to amino acid substitutions in which the amino acid residue present at a particular position in the VH or VL domain of an antibody is replaced with an amino acid residue which occurs at an equivalent position in a reference human VH or VL domain. The reference human VH or VL domain may be a VH or VL domain encoded by the human germline. Humanising substitutions may be made in the framework regions and/or the CDRs of the antibodies, defined herein.

"Humanised variants"—As used herein the term "humanised variant" or "humanised antibody" refers to a variant antibody which contains one or more "humanising substitutions" compared to a reference antibody, wherein a portion of the reference antibody (e.g. the VH domain and/or the VL domain or parts thereof containing at least one CDR) has an amino acid derived from a non-human species, and the "humanising substitutions" occur within the amino acid sequence derived from a non-human species.

"Germlined variants"—The term "germlined variant" or "germlined antibody" is used herein to refer specifically to "humanised variants" in which the "humanising substitutions" result in replacement of one or more amino acid residues present at (a) particular position(s) in the VH or VL domain of an antibody with an amino acid residue which occurs at an equivalent position in a reference human VH or VL domain encoded by the human germline. It is typical that for any given "germlined variant", the replacement amino acid residues substituted into the germlined variant are taken exclusively, or predominantly, from a single human germline-encoded VH or VL domain. The terms "humanised variant" and "germlined variant" are often used interchangeably. Introduction of one or more "humanising substitutions" into a camelid-derived (e.g. llama derived) VH or VL domain results in production of a "humanised variant" of the camelid (llama)-derived VH or VL domain. If the amino acid residues substituted in are derived predominantly or exclusively from a single human germline-encoded VH or VL domain sequence, then the result may be a "human germlined variant" of the camelid (llama)-derived VH or VL domain.

"Affinity variants"—As used herein, the term "affinity variant" refers to a variant antibody which exhibits one or more changes in amino acid sequence compared to a reference antibody, wherein the affinity variant exhibits an altered affinity for the target antigen in comparison to the reference antibody. For example, affinity variants will exhibit a changed affinity for a target as compared to a reference antibody. Preferably the affinity variant will exhibit improved affinity for the target antigen, as compared to the reference antibody. Affinity variants typically exhibit one or more changes in amino acid sequence in the CDRs, as compared to the reference antibody. Such substitutions may result in replacement of the original amino acid present at a given position in the CDRs with a different amino acid residue, which may be a naturally occurring amino acid residue or a non-naturally occurring amino acid residue. The amino acid substitutions may be conservative or non-conservative.

"Subject"—as used herein, the term "subject" refers to a mammal, preferably a human. The subject may be either a male or a female. The subject may exhibit one or more symptoms consistent with a paraproteinemic neuropathy. In certain embodiments, the subject may be a patient, where a patient is an individual who is under medical care and/or actively seeking medical care for treatment of a paraproteinemic neuropathy.

B. Methods of Treatment

The present invention provides methods of treating paraproteinemic neuropathies. The methods involve the administration to a subject of an antagonist of the complement system wherein the antagonist inhibits the complement system upstream of complement factor C5. The present invention also provides an antagonist of the complement system for use in the treatment of a paraproteinemic neuropathy, wherein the antagonist inhibits the complement system upstream of complement factor C5.

Paraproteinemic neuropathies are defined elsewhere herein and comprise a class of peripheral neuropathies characterised by the presence of a homogeneous immunoglobulin or "paraprotein" in the serum. Peripheral neuropathies are diseases or degenerative states of the peripheral nerves in which motor, sensory, or vasomotor nerve fibres are affected. Of particular interest are the immune-mediated neuropathies, which represent a class of peripheral nerve disorders caused by immune-mediated damage to the peripheral nerves. In general, immune-mediated peripheral neuropathies are characterised by progressive muscle weakness and are often accompanied by sensory deficits such as pain and numbness. These disorders are speculated to be caused by autoreactive antibodies in the serum that bind to components of myelin or to proteins located at the nodes of Ranvier. A common feature of these disorders is that the blood-nerve-barrier (BNB) is compromised allowing autoantibodies, complement components, and inflammatory cells to access the endoneurium of the nerve. This breakdown of the BNB is thought to be triggered by circulating cytokines, such as VEGF, TNFα, and IL1-β and metalloproteases secreted from T cells. Upon entry to the nerve, autoantibodies can bind to neural antigens such as myelin-associated glycoprotein (MAG) or gangliosides which are present on myelin, or at the junction between axons, respectively. As explained elsewhere herein, the formation of antibody/antigen immune complexes can initiate the classical pathway of the complement system by recruitment of C1q.

Paraproteinemic neuropathies are a group of immune-mediated neuropathies characterised by excessive immunoglobulins in the serum. PPNs are frequently associated with the presence of autoantibodies. Existing treatment strategies for this class of neuropathies currently include intravenous immune globulin (IVIg), plasmapheresis (plasma exchange), corticosteroids, azathioprine, rituximab, chlorambucil, fludarabine, melphalan and others (see Rison and Beydoun. *BMC Neurology*. (2016) 16:13).

As reported herein, immunoglobulins present in the sera of patients having different paraproteinemic neuropathies can activate complement and this supports a role for complement-mediated tissue damage in the pathology seen in PPN patients. However, a previous clinical study testing eculizumab (Soliris™—an anti-C5 antibody) in the treatment of multifocal motor neuropathy (MMN) did not demonstrate efficacy (Fitzpatrick et al., *J Peripher Nerv Syst,* 2011, 16(2):84-91).

Importantly, the present inventors have shown that both Schwann cells and motor neurons upregulate complement regulatory protein CD59, a protein that protects cells against MAC-mediated lysis. This observation indicates that elements of the complement cascade upstream of C5 play a more important role in PPN pathology. This may well explain the lack of efficacy seen previously with eculizumab. Without wishing to be bound by theory, it is thought that complement activation in paraproteinemic neuropathies induces the release of cytokines and/or chemokines through activation of the C3aR, which was found to be expressed on Schwann cells and motor neurons. Chemokines, such as MCP-1, may play a role in attracting inflammatory cells thereby promoting neurological damage.

The present invention seeks to improve the treatment of PPN by targeting complement activity upstream of complement factor C5.

The neuropathies to be treated in accordance with the methods described herein include all peripheral neuropathies categorized as "paraproteinemic neuropathies". This includes both acute and chronic disorders. Paraproteinemic neuropathies may be classified as demyelinating or axonal, or a combination thereof, depending on whether the myelin and/or the axon is damaged. In certain embodiments, the neuropathy to be treated is an axonal neuropathy. In certain embodiments, the neuropathy to be treated is a demyelinating neuropathy, for example a chronic demyelinating neuropathy.

Paraproteinemic neuropathies are frequently characterised by the presence of autoantibodies. Therefore, in certain embodiments, the neuropathies to be treated in accordance with the methods described herein are characterised by the presence of autoantibodies. High titres of serum autoantibodies recognising neural antigens occur in several forms of peripheral sensory, motor, and sensorimotor neuropathies. The antibodies frequently react with glycosylated cell surface molecules, including glycolipids, glycoproteins, and glycosaminoglycans, but antibodies to intracellular proteins have also been described. There are several correlations between antibody specificity and clinical symptoms, suggesting that the neuropathies may be caused by the antibodies. Autoantibodies, typically of the IgM or IgG isotype, are capable of activating the classical pathway of the complement system on the peripheral nerves, as described elsewhere herein. Access to the peripheral nerves by autoantibodies and complement is made possible following breakdown of the blood-nerve-barrier (BNB). In certain embodiments, the paraproteinemic neuropathy is characterised by a high-titre of autoantibodies. In certain embodiments, the paraproteinemic neuropathy is characterised by the presence of IgG, IgM or IgA autoantibodies.

In certain embodiments, the paraproteinemic neuropathy is characterised by the presence of autoantibodies against a neural antigen. In certain embodiments, the neural antigen is a protein located at the nodes of Ranvier. In other embodiments, the neural antigen is a protein located on the myelin sheath. Myelin-associated glycoprotein (MAG) is a constituent of peripheral and central nervous system myelin. High-titre IgM antibodies to MAG are associated with sensorimotor demyelinating peripheral neuropathy. MAG antibodies are usually associated with the presence of an IgM monoclonal protein. In certain embodiments, the neural antigen is myelin-associated glycoprotein (MAG).

Gangliosides are a group of glycosphingolipids widely distributed in membrane components of the nervous system. In certain embodiments, the neural antigen is a ganglioside. The gangliosides most commonly recognized by neuropathy-associated autoantibodies are GM1, GD1a, GD1 b, and GQ1 b. In certain embodiments, the ganglioside is selected from GM1, GM1b, GM2, GM3, GD1a, GD1b, GD2, GD3, GT1a, GT1b, GT3, and GQ1b. In a preferred embodiment, the ganglioside is GM1. Individual patients may possess antibodies to a single ganglioside or to multiple gangliosides. Accordingly, in certain embodiments, the paraproteinemic neuropathy is characterised by the presence of autoantibodies against one or more neural antigens. In certain embodiments, the peripheral neuropathy is characterised by the presence of autoantibodies against one or more gangliosides. In certain embodiments, the neural antigen is a paranodal protein. In certain embodiments, the neural antigen may be a paranodal protein selected from contactin 1, NF155, NF186, and NF140. Autoantibodies known to be associated with various peripheral neuropathies are described in Table 3 below. For example, IgG4 autoantibodies directed against paranodal proteins have been identified in patients with CIDP. Detection of GM1 antibody, usually of the IgM isotype, is associated with multifocal motor neuropathy and lower motor neuropathy, characterised by muscle weakness and atrophy. The GM1 IgM may be present as a monoclonal IgM paraprotein or as polyclonal IgM.

TABLE 3

Autoantibodies in peripheral neuropathies

| Disease | Antigens | Antibody isotype |
|---|---|---|
| GBS subtype | | |
| AMAN | GM1, GM1b, GD1a | IgG |
| AMSAN | GM1, GD1a | IgG |
| Miller-Fisher syndrome | GQ1b, GT1a | IgG |
| CIDP (and subtypes) | MAG, Contactin 1, NF155, NF186, NF140 | IgG4 |
| CANOMAD | GD3, GD1b, GT1b, GQ1b | IgM |
| DADS | MAG | IgM |
| MMN | GM1 | IgM |
| Anti-MAG neuropathy | MAG | IgM |
| POEMS | unknown | IgG/IgA |

Particular paraproteinemic neuropathies to be treated in accordance with the methods described herein may be selected from multifocal motor neuropathy (MMN), chronic inflammatory demyelinating polyneuropathy (CIDP), Guillain-Barre syndrome (GBS), Miller Fisher syndrome, acute motor axonal neuropathy (AMAN), acute motor and sensory axonal neuropathy (AMSAN), chronic ataxic neuropathy-ophthalmoplegia-IgM paraprotein-cold agglutinins-disialosyl antibodies (CANOMAD) syndrome, distal acquired demyelinating symmetric (DADS) neuropathy, monoclonal gammopathy associated peripheral neuropathy, anti-MAG peripheral neuropathy, and POEMS syndrome. In certain preferred embodiments, the paraproteinemic neuropathy is selected from multifocal motor neuropathy (MMN), chronic inflammatory demyelinating polyneuropathy (CIDP), Guillain-Barre syndrome (GBS). The methods described herein are particularly preferred for the treatment of multifocal motor neuropathy (MMN).

The methods described herein are for treating a paraproteinemic neuropathy in a subject in need thereof. The subject is preferably a human subject. The subject may be a patient, where a patient is an individual who is under medical care and/or actively seeking medical care for treatment of a paraproteinemic neuropathy. The subject to be treated will typically exhibit one or more symptoms consistent with a paraproteinemic neuropathy including but not limited to: gradual onset of numbness; prickling or tingling in the feet or hands, which can spread upward into the legs and arms; sharp, jabbing, throbbing, freezing or burning pain; extreme sensitivity to touch; lack of coordination and falling; twitching and muscle cramps; thinning (wasting) of muscles; muscle weakness or paralysis. The subject to be treated may have previously been diagnosed as having a paraproteinemic neuropathy by any standard assessment criteria. The subject may be identified or have been previously diagnosed on the basis of an excess of immunoglobulins in the serum. Alternatively or in addition, the subject may possess autoantibodies to one or more neural antigens The subject to be treated may already be receiving treatment for a paraproteinemic neuropathy or may have previously received treatment for a paraproteinemic neuropathy. In some embodiments, the subject has previously received or is receiving IVIg. In other embodiments, the subject has previously received or is receiving rituximab. In some embodiments, the subject has received or is receiving plasma exchange. The subject may have been unresponsive to previous treatment or may have developed resistance to previous treatment such that their symptoms have worsened.

The methods of treatment described herein may lead to a complete or partial reversal of one or more symptoms associated with PPN. Improvements in performance may be measured using any standard assessment criteria suitable for evaluating PPN treatment.

The methods of the present invention may comprise the administration of one or more additional therapeutic agents for the treatment of the paraproteinemic neuropathy. The one or more additional therapeutic agents may be administered concurrently with the complement antagonist as a combination therapy. Alternatively, the one or more additional agents may be administered prior to or after the administration of the complement antagonist i.e. the agents are administered sequentially. Additional therapeutic agents that may be administered in accordance with the methods of the invention include but are not limited to IVIg, rituximab, corticosteroids, azathioprine, chlorambucil, fludarabine, melphalan, cyclophosphamide/prednisone, melphalan, gabapentin, pregabalin, valproate, dextromethorphan, tramadol, duloxetine, amitriptyline, and venlafaxine.

C. Complement Antagonists

The results presented herein indicate that the terminal stages of the complement cascade, particularly MAC-mediated lysis, may not play a significant role in the pathology of PPN. This is because Schwann cells and motor neurons express high levels of the complement regulatory protein CD59, which protects against MAC-mediated lysis. It follows therefore that the complement-related pathology associated with the paraproteinemic neuropathies described herein may be mediated by factors upstream of C5, for example via the C3aR. The present invention therefore provides a method of treating paraproteinemic neuropathies by inhibiting the complement pathway upstream of C5.

The methods comprise administering to a subject an antagonist of the complement system, wherein the antagonist inhibits the complement system upstream of complement factor C5. An antagonist that inhibits the complement system upstream of complement factor C5 does not directly inhibit complement factor C5 itself or any of the factors downstream (C6, C7, C8, C9) that combine to form the membrane attack complex. Instead, an antagonist that inhibits the complement system upstream of complement factor C5 targets a factor or component of the complement cascade preceding complement factor C5. Complement factors upstream of C5 include C1, C2, C4, and C3. Thus, in certain embodiments, the antagonist inhibits the complement system by inhibiting the function of any one of C1, C2, C4 and C3. In certain embodiments, the antagonist inhibits the complement system by inhibiting the function of any one of C1, C1q, C1r, C1s, C2, C2a, C2b, C3, C3a, C3b, C4, C4a or C4b.

In certain embodiments, the antagonist inhibits the complement system upstream of complement factor C3. Complement factors upstream of C3 include C1, C4 and C2. Thus, in certain embodiments, the antagonist inhibits the complement system by inhibiting the function of any one of C1, C2 and C4. In certain embodiments, the antagonist inhibits the complement system by inhibiting the function of any one of C1, C1q, C1 r, C1s, C2, C2a, C2b, C4, C4a or C4b.

The initiating factor of the classical complement pathway is complement factor C1. Therefore, in some embodiments, the antagonist inhibits complement factor C1. In other embodiments, the antagonist inhibits complement factor C1q C1 r, or C1s. By inhibiting the complement cascade at complement factor C1, it is possible to prevent or reduce cleavage of the C1-specific targets, C4 and C2, and to specifically inhibit activation of complement via the classical pathway of the complement system. Inhibition of C1 can reduce deposition of the opsonin C4b, thereby reducing the targeting of cells for phagocytosis and destruction. In addition, inhibition of C1 can prevent or reduce formation of the C3 convertase, C4bC2a. C4 and C2 may also be cleaved by MASP enzymes via the lectin pathway; however, total levels of C3 convertase may still be significantly inhibited by targeting complement factor C1.

In certain embodiments, the antagonist inhibits complement factor C4. In other embodiments, the antagonist inhibits complement factor C4a or C4b. By targeting complement factor C4, it is possible to prevent formation of the C3 convertase, C4bC2a, and to inhibit complement activation via both the classical and lectin pathways of the complement system.

In certain embodiments, the antagonist inhibits complement factor C2. In other embodiments, the antagonist inhibits complement factor C2a or C2b. Inhibition of C2 will also prevent or reduce formation of the C3 convertase, thus reducing deposition of the anaphylatoxin C3a and the opsonin C3b, and other complement activation products downstream of C2. The antagonist of C2 may directly inhibit C2a preventing formation of the C3 convertase. Alternatively, the antagonist may inhibit C2b preventing the initial binding of C2 to surface-bound C4b. An antagonist of C2b may leave the binding of C2a to C4b intact. C2 activity may nevertheless be significantly inhibited by an antagonist of C2b.

In certain embodiments, the antagonist inhibits complement factor C3. In other embodiments, the antagonist inhibits complement factor C3a or C3b. Inhibition of C3 can prevent or reduce formation of the C5 convertase, C3bBbC3b, thus reducing deposition of the anaphylatoxin C5a and MAC generator, C5b.

Depending on the point in the complement cascade at which the antagonist inhibits the complement system, the antagonist may inhibit the classical complement pathway, the lectin complement pathway, the alternative complement pathway or a combination of these pathways. In certain embodiments, the antagonist inhibits the classical complement pathway and the lectin complement pathway but does not affect the alternative complement pathway. Antagonists targeting C2 and C4 are capable of inhibiting the classical and lectin complement pathways whilst leaving the alternative pathway intact. In some instances, it may be beneficial to leave one of the complement pathways intact such that this important arm of the innate immune system is not disabled entirely. Alternatively or in addition, the antagonist may only need to bring about partial inhibition of complement activity in order to achieve a therapeutic effect.

The antagonists for use in the therapeutic methods described herein inhibit factors or components of the complement system upstream of complement factor C5 so as to inhibit or reduce complement activity. As reported herein, it is beneficial to target the complement cascade upstream of C5 so as to inhibit the activity of complement factors that precede formation of the MAC complex. The antagonists for use in accordance with the methods described herein may reduce or inhibit complement activity by inhibiting the generation of the biologically active, complement-derived peptides such as C4a, C4b, C3a, C3b, and C5a. The antagonist may prevent, at least in part, damaging effects of complement-derived peptides on cells and tissues. The antagonist of the complement system may inhibit or reduce complement activity by reducing deposition of anaphylatoxins, by reducing deposition of opsonins, by reducing cytokine and/or chemokine production or secretion, by reducing phagocytosis, by reducing the recruitment of immune cells, and any combination thereof. In certain embodiments, the antagonist of the complement system inhibits the deposition of anaphylatoxins. In certain embodiments, the antagonist inhibits the deposition of C3a or C5a. In certain embodiments, the antagonist inhibits the deposition of opsonins. In certain embodiments, the antagonist inhibits the deposition of C3b or C4b. In certain embodiments, the antagonist inhibits production and/or secretion of inflammatory cytokines and/or chemokines. In some embodiments, the antagonist inhibits the production and/or secretion of MCP-1.

The antagonist for use in the present invention may be any agent capable of inhibiting the function of a complement factor thereby inhibiting or reducing complement activity. As noted elsewhere herein, it is preferred that the antagonists for use in the methods exhibit specificity for their target. This specificity is typically achieved by the antagonist binding directly to its target and inhibiting the function of the target.

In some embodiments, the antagonist is selected from: inhibitory RNA species, for example siRNAs or shRNAs; small molecule inhibitors; biological antagonists including inhibitory peptides, antibody mimetics such as affibodies, affilins, affitins, adnectins, atrimers, evasins, DARPins, anticalins, avimers, fynomers, versabodies and duocalins; antibodies and antigen-binding fragments thereof.

In preferred embodiments, the antagonist is an antibody or antigen-binding fragment thereof. In certain embodiments, the antibody or antigen-binding fragment thereof binds to complement factor C1, C1q, C1s, C1r, C2, C2a, C2b, C3, C3a, C3b, C4, C4a or C4b. In certain embodiments, the antibody or antigen-binding fragment binds to complement factor C1, C1q, C1s, C1r, C2, C2a, C2b, C4, C4a or C4b. In preferred embodiments, the antibody or antigen-binding fragment binds to C2, preferably C2b.

The antibodies and antigen-binding fragment for use in the methods described herein are intended for human therapeutic use and therefore, will typically be of the IgA, IgD, IgE, IgG, IgM type, often of the IgG type, in which case they can belong to any of the four sub-classes IgG1, IgG2a and b, IgG3 or IgG4. In preferred embodiments, the antibodies are IgG antibodies, optionally IgG1 antibodies. The antibodies may be monoclonal, polyclonal, multispecific (e.g. bispecific antibodies) antibodies, provided that they exhibit the appropriate immunological specificity for their target. Monoclonal antibodies are preferred since they are highly specific, being directed against a single antigenic site.

The antigen binding fragments described herein will typically comprise a portion of a full-length antibody, generally the antigen binding or variable domain thereof. Examples of antibody fragments include Fab, Fab', F(ab')2, bi-specific Fab's, and Fv fragments, linear antibodies, single-chain antibody molecules, a single chain variable fragment (scFv) and multispecific antibodies formed from antibody fragments (see Holliger and Hudson (2005) Nature Biotechnol. 23:1126-36, incorporated herein by reference).

The antibodies or antigen-binding fragments for use in accordance with the methods described herein may exhibit high human homology. Such antibody molecules having high human homology may include antibodies comprising VH and VL domains of native non-human antibodies which exhibit sufficiently high % sequence identity to human germline sequences. In certain embodiments, the antibody molecules are humanised or germlined variants of non-human antibodies.

In non-limiting embodiments, the antibodies may comprise CH1 domains and/or CL domains (from the heavy chain and light chain, respectively), the amino acid sequence of which is fully or substantially human. For antibody molecules intended for human therapeutic use, it is typical for the entire constant region of the antibody, or at least a part thereof, to have a fully or substantially human amino acid sequence. Therefore, one or more or any combination of the CH1 domain, hinge region, CH2 domain, CH3 domain and CL domain (and CH4 domain if present) may be fully or substantially human with respect to its amino acid sequence. The CH1 domain, hinge region, CH2 domain, CH3 domain and/or CL domain (and/or CH4 domain if present) may be derived from a human antibody, preferably a human IgG antibody, more preferably a human IgG1 antibody of subtype IgG1, IgG2, IgG3 or IgG4.

Advantageously, the CH1 domain, hinge region, CH2 domain, CH3 domain and CL domain (and CH4 domain if present) may all have fully or substantially human amino acid sequences. In the context of the constant region of a humanised or chimeric antibody, or an antibody fragment, the term "substantially human" refers to an amino acid sequence identity of at least 90%, or at least 92%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes.

In an embodiment the antibody or antibody fragment comprises a human Fc domain, which comprises one or more mutations designed to increase the serum half-life of the antibody or antibody molecule. Such optimization efforts aim to improve antibody circulation in vivo. Examples of half-life affecting mutations in the human IgG Fc domain include His433Lys+Asn434Phe (NHance); Arg435His; Asn434Ala; Met252Tyr+Ser254Thr+Thr256Glu (YTE); Met428Leu+Asn434Ser (LS); Thr252Leu+Thr253Ser+Thr254Phe (LSF); Glu294delta+Thr307Pro+Asn434Tyr (C6A-66); Thr256Asn+Ala378Val+Ser383Asn+Asn434Tyr (C6A-78); and Glu294delta (del). Depending on the serum half-life of the complement inhibitor, it may be administered as a single dose, or it may be administered as multiple doses with an interval of from 1 day to 1 month between subsequent doses.

In another embodiment the Fc domain may comprise one or more mutations designed to impair the effector function of the Fc domain. Such mutations are well known to those skilled in the art. In the case of human IgG1, the antibody may comprise a human Fc domain that has been modified to abrogate or impair its effector function. Such Fc domain mutations generally comprise changing at least 1 amino acid from the heavy chain constant region on position 234, 235, 236, 237, 297, 318, 320 or 322, thereby causing an alteration in effector function while retaining binding to antigen. Examples of effector-impairing mutations in the human IgG Fc domain include Leu234Ala+Leu235Ala (referred to as LALA); Leu234Ala+Leu235Ala+Pro329Gly (referred to as LALA-PG); Ser228Pro+Leu235Glu in IgG4; Pro331Ser+Leu234Glu+Leu235Phe; and Pro331Ser+Leu234Ala+Leu235Ala.

Examples of antagonists suitable for use in the present invention that inhibit complement factor C1 include Cinryze (Shire), sutimlimab—also known as TNT009 and BIV009

(Bioverativ), TNT003 (True North), ANX005 (Annexon) and nafamostat (Torii Pharmaceutical).

Examples of antagonists suitable for use in the present invention that inhibit complement factor C3 include compstatin Cp40 (Amyndas), PEG-Cp40 (Amyndas), AMY-101 (Amyndas), AMY-201 (Amyndas), APL-1 and APL-2 (Apellis), CDX-1135 (Celldex), APTO70 Mirococept (MRC), HC3-1496 (InCode), humanised monoclonal antibody H17 (Elusys Therapeutics) or vacciniá virus complement control protein (VCP).

D. Anti-C2 Antibodies and Antigen-Binding Fragments

Particularly preferred complement antagonists for use in the therapeutic methods described herein are those that inhibit complement factor C2. In preferred embodiments, the complement antagonist for use in treatment is an antibody or antigen-binding fragment thereof that binds to C2. Suitable anti-C2 antibodies and antigen-binding fragments for use in the methods described herein include the antibodies and antigen-binding fragments identified in International patent application no. WO2014/189378, the contents of which are incorporated herein in their entirety.

C2 is a 90-100 kDa glycoprotein which participates in the classical and lectin pathways of complement activation. As described above, C2 can be activated by C1s of the classical pathway or by activated MASP2 of the lectin pathway. C2 binds to surface-bound C4b (in the presence of $Mg^{2+}$) to form a C4bC2 complex, which then is cleaved by activated C1s or MASP2 into two fragments: a larger 70 kDa fragment C2a, which remains attached to C4b to form a C3-convertase C4bC2a, and a smaller 30 kDa N-terminal fragment C2b, which is released into the fluid phase. Once activated and bound to C4b, C2a constitutes the catalytic subunit of the C3 and C5 convertases which are able to cleave C3 and C5, respectively.

The amino acid sequence of human C2 is known (GenBank Accession No. NM_000063) and shown as SEQ ID NO: 1 below.

```
Amino Acid Sequence of human C2
(SEQ ID NO: 1):
MGPLMVLFCLLFLYPGLADSAPSCPQNVNISGGTFTLSHGWAPGSLLTYS

CPQGLYPSPASRLCKSSGQWQTPGATRSLSKAVCKPVRCPAPVSFENGIY

TPRLGSYPVGGNVSFECEDGFILRGSPVRQCRPNGMWDGETAVCDNGAGH

CPNPGISLGAVRTGFRFGHGDKVRYRCSSNLVLTGSSERECQGNGVWSGT

EPICRQPYSYDFPEDVAPALGTSFSHMLGATNPTQKTKESLGRKIQIQRS

GHLNLYLLLDCSQSVSENDFLIFKESASLMVDRIFSFEINVSVAIITFAS

EPKVLMSVLNDNSRDMTEVISSLENANYKDHENGTGTNTYAALNSVYLMM

NNQMRLLGMETMAWQEIRHAIILLTDGKSNMGGSPKTAVDHIREILNINQ

KRNDYLDIYAIGVGKLDVDWRELNELGSKKDGERHAFILQDTKALHQVFE

HMLDVSKLTDTICGVGNMSANASDQERTPWHVTIKPKSQETCRGALISDQ

WVLTAAHCFRDGNDHSLWRVNVGDPKSQWGKEFLIEKAVISPGFDVFAKK

NQGILEFYGDDIALLKLAQKVKMSTHARPICLPCTMEANLALRRPQGSTC
```

-continued

```
RDHENELLNKQSVPAHFVALNGSKLNINLKMGVEWTSCAEVVSQEKTMFP

NLTDVREVVTDQFLCSGTQEDESPCKGESGGAVFLERRFRFFQVGLVSWG

LYNPCLGSADKNSRKRAPRSKVPPPRDFHINLFRMQPWLRQHLGDVLNFL

PL
```

In certain embodiments, the antibody or antigen-binding fragment binds to C2b and comprises a variable heavy chain (VH) domain and a variable light chain (VL) domain, wherein the VH and VL domains comprise the CDR sequences:

```
HCDR3 comprising or consisting of
                              SEQ ID NO: 2
[EDDHDAFAY];

HCDR2 comprising or consisting of
                              SEQ ID NO: 3
[DINPNYESTGYNQKFKG];

HCDR1 comprising or consisting of
                              SEQ ID NO: 4
[DYNMD];

LCDR3 comprising or consisting of
                              SEQ ID NO: 5
[QHSRELPYT];

LCDR2 comprising or consisting of
                              SEQ ID NO: 6
[LASNLKS];
and

LCDR1 comprising or consisting of
                              SEQ ID NO: 7
[RASKSVRTSGYNYMH].
```

In certain embodiments, the antibody or antigen-binding fragment binds to C2b and comprises a variable heavy chain (VH) domain comprising or consisting of a sequence at least 70%, at least 80%, at least 90% or at least 95% identical to SEQ ID NO: 8 and a variable light chain (VL) domain comprising or consisting of a sequence at least 70%, at least 80%, at least 90% or at least 95% identical to SEQ ID NO: 9. In certain embodiments, the antibody or antigen-binding fragment that binds to C2b comprises a variable heavy chain domain (VH domain) comprising or consisting of SEQ ID NO: 8 and a variable light chain domain (VL domain) comprising or consisting of SEQ ID NO: 9.

In certain embodiments, the antibody or antigen-binding fragment binds to C2b and comprises a variable heavy chain (VH) domain and a variable light chain (VL) domain, wherein the VH domain comprises or consists of a sequence at least 70%, at least 80%, at least 90% or at least 95% identical to SEQ ID NO: 8 and the VL domain comprises the CDR sequences:

```
LCDR3 comprising or consisting of
                              SEQ ID NO: 5
[QHSRELPYT];

LCDR2 comprising or consisting of
                              SEQ ID NO: 6
[LASNLKS];
and

LCDR1 comprising or consisting of
                              SEQ ID NO: 7
[RASKSVRTSGYNYMH].
```

In certain embodiments, the antibody or antigen-binding fragment binds to C2b and comprises a variable heavy chain (VH) domain and a variable light chain (VL) domain, wherein the VH domain comprises or consists of the amino acid sequence of SEQ ID NO: 8 and the VL domain comprises the CDR sequences:

LCDR3 comprising or consisting of SEQ ID NO: 5 [QHSRELPYT];

LCDR2 comprising or consisting of SEQ ID NO: 6 [LASNLKS]; and

LCDR1 comprising or consisting of SEQ ID NO: 7 [RASKSVRTSGYNYMH].

In certain embodiments, the antibody or antigen-binding fragment binds to C2b and comprises a variable heavy chain (VH) domain and a variable light chain (VL) domain, wherein the VH domain comprises the CDR sequences:

HCDR3 comprising or consisting of SEQ ID NO: 2 [EDDHDAFAY];

HCDR2 comprising or consisting of SEQ ID NO: 3 [DINPNYESTGYNQKFKG];

HCDR1 comprising or consisting of SEQ ID NO: 4 [DYNMD], and the VL domain comprises or consists of a sequence at least 70%, at least 80%, at least 90% or at least 95% identical to SEQ ID NO: 9.

In certain embodiments, the antibody or antigen-binding fragment binds to C2b and comprises a variable heavy chain (VH) domain and a variable light chain (VL) domain, wherein the VH domain comprises the CDR sequences:

HCDR3 comprising or consisting of SEQ ID NO: 2 [EDDHDAFAY];

HCDR2 comprising or consisting of SEQ ID NO: 3 [DINPNYESTGYNQKFKG];

HCDR1 comprising or consisting of SEQ ID NO: 4 [DYNMD], and the VL domain comprises or consists of the amino acid sequence of SEQ ID NO: 9.

For embodiments wherein the domains of the antibodies or antigen binding fragments are defined by a particular percentage sequence identity to a reference sequence, the VH and/or VL domains may retain identical CDR sequences to those present in the reference sequence such that the variation is present only within the framework regions.

TABLE 4

VH and VL domain sequences

| Variable domain | Sequence | SEQ ID NO: |
|---|---|---|
| VH | EVQLVQSGAEVKKPGASVKVSCKASGYTFTDY NMDWVRQATGQGLEWIGDINPNYESTGYNQKF KGRATMTVDKSISTAYMELSSLRSEDTAVYYC AREDDHDAFAYWGQGTLVTVSS | 8 |
| VL | DNVLTQSPDSLAVSLGERATISCRASKSVRTS GYNYMHWYQQKPGQPPKLLIYLASNLKSGVPD RFSGSGSGTDFTLTISSLQAEDAATYYCQHSR ELPYTFGQGTKLEIK | 9 |

In certain embodiments, the anti-C2b antibodies include the CH1 domain, hinge domain, CH2 domain, and/or CH3 domain of a human antibody, in particular human IgG1, IgG2, IgG3 or IgG4. In certain embodiments, the anti-C2b antibody includes the CH1 domain, hinge domain, CH2 domain, and CH3 domain of a human IgG1 and includes the substitutions L234A and L235A in the CH2 domain, wherein the positions are defined in accordance with EU numbering. Alternatively or in addition, the anti-C2b antibody includes the CH1 domain, hinge domain, CH2 domain, and CH3 domain of a human IgG1 and includes the substitutions H433K and N434F in the CH3 domain, wherein the positions are defined in accordance with EU numbering. EU numbering refers to the convention for the Fc region described in Edelman, G. M. et al., *Proc. Natl. Acad. Sci. USA,* 63: 78-85 (1969); and Kabat et al., in "Sequences of Proteins of Immunological Interest", U.S. Dept. Health and Human Services, 5th edition, 1991.

In certain embodiments, the anti-C2b antibody includes the CH1 domain, hinge domain, CH2 domain, and CH3 domain of a human IgG4. In certain embodiments, the antibody includes the CH1 domain, hinge domain, CH2 domain, and CH3 domain of a human IgG4 and includes the substitution S228P in the hinge domain.

In certain embodiments, the anti-C2b antibody includes the CH1 domain, hinge domain, CH2 domain, and CH3 domain of a human IgG4 and includes the substitution L445P in the CH3 domain.

In certain embodiments, the anti-C2b antibody includes the CH1 domain, hinge domain, CH2 domain, and CH3 domain of a human IgG4 and includes both the substitution S228P in the hinge domain and the substitution L445P in the CH3 domain.

In certain embodiments, the anti-C2b antibody includes the CH1 domain, hinge domain, CH2 domain, and CH3 domain of a human IgG4 and includes the substitutions H433K and N434F in the CH3 domain.

In certain embodiments, the anti-C2b antibody includes the CH1 domain, hinge domain, CH2 domain, and CH3 domain of a human IgG4 and includes the substitution S228P in the hinge domain, and the substitutions H433K and N434F in the CH3 domain.

In certain embodiments, the anti-C2b antibody comprises a human IgG heavy chain constant domain. In certain embodiments, the heavy chain constant domain comprises a human IgG1 heavy chain constant domain. In certain embodiments, the heavy chain constant domain consists of a human IgG1 heavy chain constant domain. In certain embodiments, the heavy chain constant domain comprises a human IgG1 heavy chain constant domain comprising or consisting of the amino acid sequence set forth as SEQ ID NO: 10 or 11.

In certain embodiments, the heavy chain constant domain comprises a human IgG4 heavy chain constant domain. In certain embodiments, the heavy chain constant domain consists of a human IgG4 heavy chain constant domain. In certain embodiments, the heavy chain constant domain comprises a human IgG4 heavy chain constant domain comprising or consisting of the amino acid sequence set forth in any one of SEQ ID NOs: 12, 13 or 14.

The heavy chain constant domains are shown in Table 5 below.

TABLE 5

Heavy Chain Constant Domains

| ID | Sequence | SEQ ID NO: |
|---|---|---|
| Human IgG1 (UniProt) | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKV EPKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLT VDKSRWQQGNVFSCSVMHEALHNHYTQKSLSLSPGK | 10 |
| Human IgG1 LALA NHance (ARGX-117) | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKV EPKSCDKTHTCPPCPAPEAAGGPSVFLFPPKPKDTLMISRTPEVTCVVV DVSHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLT VDKSRWQQGNVFSCSVMHEALKFHYTQKSLSLSPG | 11 |
| Human IgG4 (UniProt) | ASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKRV ESKYGPPCPSCPAPEFLGGPSVFLFPPKPKDTLMISRTPEVTCVVVDVS QEDPEVQFNWYVDGVEVHNAKTKPREEQFNSTYRVVSVLTVLHQDWLNG KEYKCKVSNKGLPSSIEKTISKAKGQPREPQVYTLPPSQEEMTKNQVSL TCLVKGFYPSDIAVEWESNGQPENNYKTTPPVLDSDGSFFLYSRLTVDK SRWQEGNVFSCSVMHEALHNHYTQKSLSLSLGK | 12 |
| Human IgG4 S228P L445P | ASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKRV ESKYGPPCPPCPAPEFLGGPSVFLFPPKPKDTLMISRTPEVTCVVVDVS QEDPEVQFNWYVDGVEVHNAKTKPREEQFNSTYRVVSVLTVLHQDWLNG KEYKCKVSNKGLPSSIEKTISKAKGQPREPQVYTLPPSQEEMTKNQVSL TCLVKGFYPSDIAVEWESNGQPENNYKTTPPVLDSDGSFFLYSRLTVDK SRWQEGNVFSCSVMHEALHNHYTQKSLSLSPGK | 13 |
| Human IgG4 S228P NHance L445P | ASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKRV ESKYGPPCPPCPAPEFLGGPSVFLFPPKPKDTLMISRTPEVTCVVVDVS QEDPEVQFNWYVDGVEVHNAKTKPREEQFNSTYRVVSVLTVLHQDWLNG KEYKCKVSNKGLPSSIEKTISKAKGQPREPQVYTLPPSQEEMTKNQVSL TCLVKGFYPSDIAVEWESNGQPENNYKTTPPVLDSDGSFFLYSRLTVDK SRWQEGNVFSCSVMHEALKFHYTQKSLSLSPGK | 14 |

In certain embodiments, the anti-C2b antibody comprises or consists of a light chain with at least 90%, at least 95%, at least 97%, at least 98%, or at least 99% sequence identity to the amino acid sequence shown as SEQ ID NO: 20, and a heavy chain selected from the following:

(i) a heavy chain with at least 90%, at least 95%, at least 97%, at least 98%, or at least 99% sequence identity to the amino acid sequence shown as SEQ ID NO: 15;

(ii a heavy chain with at least 90%, at least 95%, at least 97%, at least 98%, or at least 99% sequence identity to the amino acid sequence shown as SEQ ID NO: 16;

(iii) a heavy chain with at least 90%, at least 95%, at least 97%, at least 98%, or at least 99% sequence identity to the amino acid sequence shown as SEQ ID NO: 17;

(iv) a heavy chain with at least 90%, at least 95%, at least 97%, at least 98%, or at least 99% sequence identity to the amino acid sequence shown as SEQ ID NO: 18; and (v) a heavy chain with at least 90%, at least 95%, at least 97%, at least 98%, or at least 99% sequence identity to the amino acid sequence shown as SEQ ID NO: 19.

In certain embodiments, the anti-C2b antibody comprises a light chain having the amino acid sequence of SEQ ID NO: 20 and a heavy chain having an amino acid sequence selected from SEQ ID NOs: 15-19.

In a preferred embodiment, the anti-C2b antibody comprises a light chain having the amino acid sequence of SEQ ID NO: 20 and a heavy chain having the amino acid sequence of SEQ ID NO: 16.

The heavy and light chain sequences are shown in Table 6 below.

TABLE 6

Heavy Chains and Light Chains

| ID | Sequence | SEQ ID NO: |
|---|---|---|
| Human IgG1 (UniProt) | EVQLVQSGAEVKKPGASVKVSCKASGYTFTDYNMDWVRQATGQGLEWIGDIN PNYESTGYNQKFKGRATMTVDKSISTAYMELSSLRSEDTAVYYCAREDDHDA FAYWGQGTLVTVSSASTKGPSVFPLAPSSKSTSGGTAALGCLVKDYFPEPVT VSWNSGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISRTPEV TCVVVDVSHEDPEVKFNWYVDGVEVHNAKTKPREEQYNSTYRVVSVLTVLHQ | 15 |

TABLE 6-continued

| Heavy Chains and Light Chains | | |
|---|---|---|
| ID | Sequence | SEQ ID NO: |
| | DWLNGKEYKCKVSNKALPAPIEKTISKAKGQPREPQVYTLPPSRDELTKNQV SLTCLVKGFYPSDIAVEWESNGQPENNYKTTPPVLDSDGSFFLYSKLTVDKS RWQQGNVFSCSVMHEALHNHYTQKSLSLSPGK | |
| Human IgG1 LALA NHance (ARGX-117) | EVQLVQSGAEVKKPGASVKVSCKASGYTFTDYNMDWVRQATGQGLEWIGDIN PNYESTGYNQKFKGRATMTVDKSISTAYMELSSLRSEDTAVYYCAREDDHDA FAYWGQGTLVTVSSASTKGPSVFPLAPSSKSTSGGTAALGCLVKDYFPEPVT VSWNSGALTSGVHTFPAVLQSSGLYSLSSVVTVPSSSLGTQTYICNVNHKPS NTKVDKKVEPKSCDKTHTCPPCPAPEAAGGPSVFLFPPKPKDTLMISRTPEV TCVVVDVSHEDPEVKFNWYVDGVEVHNAKTKPREEQYNSTYRVVSVLTVLHQ DWLNGKEYKCKVSNKALPAPIEKTISKAKGQPREPQVYTLPPSRDELTKNQV SLTCLVKGFYPSDIAVEWESNGQPENNYKTTPPVLDSDGSFFLYSKLTVDKS RWQQGNVFSCSVMHEALKFHYTQKSLSLSPG | 16 |
| Human IgG4 (UniProt) | EVQLVQSGAEVKKPGASVKVSCKASGYTFTDYNMDWVRQATGQGLEWIGDIN PNYESTGYNQKFKGRATMTVDKSISTAYMELSSLRSEDTAVYYCAREDDHDA FAYWGQGTLVTVSSASTKGPSVFPLAPCSRSTSESTAALGCLVKDYFPEPVT VSWNSGALTSGVHTFPAVLQSSGLYSLSSVVTVPSSSLGTKTYTCNVDHKPS NTKVDKRVESKYGPPCPSCPAPEFLGGPSVFLFPPKPKDTLMISRTPEVTCV VVDVSQEDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSRWQ EGNVFSCSVMHEALHNHYTQKSLSLSLGK | 17 |
| Human IgG4 S228P L445P | EVQLVQSGAEVKKPGASVKVSCKASGYTFTDYNMDWVRQATGQGLEWIGDIN PNYESTGYNQKFKGRATMTVDKSISTAYMELSSLRSEDTAVYYCAREDDHDA FAYWGQGTLVTVSSASTKGPSVFPLAPCSRSTSESTAALGCLVKDYFPEPVT VSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCV WDVSQEDPEVQFNWYVDGVEVHNAKTKPREEQFNSTYRVVSVLTVLHQDWLN GKEYKCKVSNKGLPSSIEKTISKAKGQPREPQVYTLPPSQEEMTKNQVSLTC LVKGFYPSDIAVEWESNGQPENNYKTTPPVLDSDGSFFLYSRLTVDKSRWQE GNVFSCSVMHEALHNHYTQKSLSLSPGK | 18 |
| Human IgG4 S228P NHance L445P | EVQLVQSGAEVKKPGASVKVSCKASGYTFTDYNMDWVRQATGQGLEWIGDIN PNYESTGYNQKFKGRATMTVDKSISTAYMELSSLRSEDTAVYYCAREDDHDA FAYWGQGTLVTVSSASTKGPSVFPLAPCSRSTSESTAALGCLVKDYFPEPVT VSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCV WVDVSQEDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSRWQ EGNVFSCSVMHEALKFHYTQKSLSLSPGK | 19 |
| Light Chain (ARGX-117) | DNVLTQSPDSLAVSLGERATISCRASKSVRTSGYNYMHWYQQKPGQPPKLLI YLASNLKSGVPDRFSGSGSGTDFTLTISSLQAEDAATYYCQHSRELPYTFGQ GTKLEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSP VTKSFNRGEC | 20 |

In a preferred embodiment, the anti-C2b antibody is a monoclonal IgG antibody.

For embodiments wherein the heavy and/or light chains of the antibodies are defined by a particular percentage sequence identity to a reference sequence, the heavy chain and/or light chain may retain identical CDR sequences to those present in the reference sequence such that the variation is present only outside the CDR regions.

Unless otherwise stated in the present application, % sequence identity between two amino acid sequences may be determined by comparing these two sequences aligned in an optimum manner and in which the amino acid sequence to be compared can comprise additions or deletions with respect to the reference sequence for an optimum alignment between these two sequences. The percentage of identity is calculated by determining the number of identical positions for which the amino acid residue is identical between the two sequences, by dividing this number of identical positions by the total number of positions in the comparison window and by multiplying the result obtained by 100 in order to obtain the percentage of identity between these two sequences. For example, it is possible to use the BLAST program, "BLAST 2 sequences" (Tatusova et al, "Blast 2 sequences—a new tool for comparing protein and nucleotide sequences", *FEMS Microbiol Lett.* 174:247-250), the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program.

The anti-C2 antibodies may be modified within the Fc region to increase binding affinity for the neonatal receptor FcRn, preferably human FcRn. The increased binding affinity may be measurable at acidic pH (for example from about approximately pH 5.5 to approximately pH 6.0). The increased binding affinity may also be measurable at neutral pH (for example from approximately pH 6.9 to approximately pH 7.4). By "increased binding affinity" is meant increased binding affinity to FcRn relative to binding affinity of unmodified Fc region. Typically the unmodified Fc region will possess the wild-type amino acid sequence of human IgG1, IgG2, IgG3 or IgG4. In such embodiments, the increased binding affinity to FcRn of the antibody molecule having the modified Fc region will be measured relative to the binding affinity of wild-type IgG1, IgG2, IgG3 or IgG4 for FcRn, preferably human FcRn.

E. Pharmaceutical Compositions

The antagonists, particularly the antibodies and antigen-binding fragments, for use in the therapeutic methods described herein may be formulated as pharmaceutical compositions for administration to the subject.

Pharmaceutical compositions may be formulated with pharmaceutically acceptable carriers or diluents as well as any other known adjuvants and excipients in accordance with conventional techniques such as those disclosed in (Remington: The Science and Practice of Pharmacy, 19th Edition, Gennaro, Ed., Mack Publishing Co., Easton, Pa., 1995). The term "pharmaceutically acceptable carrier" relates to carriers or excipients, which are inherently non-toxic. Examples of such excipients are, but are not limited to, saline, Ringer's solution, dextrose solution and Hanks' solution. Non-aqueous excipients such as fixed oils and ethyl oleate may also be used.

Pharmaceutical compositions typically must be sterile and stable under the conditions of manufacture and storage. The composition can be formulated as a solution, micro-emulsion, liposome, or other ordered structure suitable to high drug concentration. Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The pharmaceutical compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol, sorbic acid, and the like. It may also be desirable to include isotonicity agents, such as sugars, polyalcohols such as mannitol, sorbitol, glycerol or sodium chloride in the compositions. Pharmaceutically-acceptable antioxidants may also be included, for example (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions may be administered via any suitable mode of administration. For example, administration may be parenteral, preferably by intravenous (i.v.) or subcutaneous (s.c.) injection or infusion. The phrases "parenteral administration" and "administered parenterally" as used herein mean modes of administration other than enteral and topical administration, usually by injection, and include, without limitation, intravenous, intraperitoneal, subcutaneous, intramuscular, intraarterial, intrathecal, intracapsular, intraorbital, intracardiac, intradermal, transtracheal, subcuticular, intraarticular, subcapsular, subarachnoid, intraspinal, epidural and intrasternal injection and infusion.

INCORPORATION BY REFERENCE

Various publications are cited in the foregoing description and throughout the following examples, each of which is incorporated by reference herein in its entirety.

EXAMPLES

The invention will be further understood with reference to the following non-limiting examples.

Example 1 Complement Inhibition in an In Vitro Model of Multifocal Motor Neuropathy (MMN) Using Living Schwann Cells Schwann cells are myelin secreting glial cells that spirally wrap around an axon of the peripheral nerve system to form the myelin sheath. These cells are attached to axons by the protein GM1. Their most important function is myelination of axons to increase the saltatory conduction of neurons, but they also assist in neuronal survival and signaling. Dysfunction of these cells causes demyelination leading to diminished signal transduction. As such, Schwann cells are associated with several demyelinating disorders like MMN. A human Schwann cell line exists—sNF02.2—and was derived from a lung metastasis, diagnosed as Malignant Peripheral Nerve Sheath Tumor, in a patient. The cells were established from numerous passages of primary tumor material in culture until they formed a homogenous Schwann cell-like population, which displays a clonal morphology positive for Schwann cell markers S100 and p75. This cell line purchased from ATCC® was used in the experiments described herein.

A. Methods 1.1 Protocol for Culturing Schwann Cells sNF02.2 (ATCC® CRL-2885™) or sNF96.2 (ATCC© CRL-2884) Schwann cells were cultured in DMEM medium completed with 100 U/mL penicillin, 100 μg/mL streptomycin and supplemented with 10% FCS at 37° C. at 5% $CO_2$. Twice a week, when confluency had reached >80%, cells were passaged or used in experiments. Medium was discarded and cells were washed with 10 ml PBS. To dissociate cells, 3 mL (T75) or 5 mL (T175) Accutase cell detachment solution (eBioscience™, Thermo Fischer Scientific; Cat. N° 00-455-56) was added, and cells were incubated at 37° C. for 5 min, or until cells fully detached. Then, culture medium (7 mL to T75 and 10 mL to T175) was added and cells were transferred to 15 mL tubes prior to centrifugation (125×g, 10 min). Pellets were re-suspended in 5 ml culture medium and counted using trypan blue to discriminate viable cells from dead cells. Next, cells were adjusted to the desired concentration and seeded into culture flasks (10 mL in T75, 20 mL in T175) or used in FACS experiments.

1.2 Protocol for Staining Schwann Cells

Cells were cultured as described above and after counting, 50,000 cells were transferred to a v-bottom plate. Cells were washed once in FACS buffer (PBS 1% BSA 0.01% natrium azide) and stained with respective antibodies diluted in FACS buffer for 45 min on ice in the dark (see Table 7 for FACs staining antibodies). If needed, cells were washed once by adding 100 μL FACS buffer followed by 5 min centrifugation at 125×g. Next, cells were incubated with a secondary antibody for 45 min on ice in the dark. After incubation, 100 μL FACS buffer was added and cells were centrifuged (5 min at 125×g). Finally, the cell pellet was re-suspended in 100 μL FACS buffer and analyzed using a FACS Canto II and accompanying software.

TABLE 7

FACS staining antibodies

| Antibody | Label/ Fluorochrome | Company | Cat. N° | Clone |
|---|---|---|---|---|
| CD46 | FITC | BD | 555949 | E4.3 |
| Mouse IgG2a | FITC | BioLegend | 400207 | MOPC-173 |
| CD55 | FITC | BioLegend | 311306 | JS11 |
| Mouse IgG1 | FITC | BD | 556028 | |
| CD59 | APC | eBioscience | 17-0596 | OV9A2 |
| Mouse IgG1 | APC | Biolegend | 400119 | MOPC-21 |
| CD64 | AF647 | Sony | 2125060 | 10.1 |
| Mouse IgG1 | AF647 | Biolegend | 400155 | MOPC-21 |
| CD88 (C3aR) | PE | Biolegend | 345804 | hC3aRZ8 |
| Mouse IgG2b | PE | BD | 555058 | 37-35 |
| Mouse IgG2b | PE | BD | 559529 | MCP-11 |
| CholeraToxinB subunit | AF488 | Thermofisher | C34775 | |
| Rabbit anti-MAG | | Thermofisher | PA5-49646 | |
| Goat anti-rabbit | AF488 | Life technologies | A11070 | |
| Rabbit anti-RBC | | LSBio | LS-C347937 | |
| C3 | Biotin | LSBio | LS-C62849 | 6C9 |
| C3 | FITC | LSBio | LS-C62855 | 6C9 |
| Anti-human IgM F(ab)'2 | FITC | Southern-Biotech | 2022-02 | |
| CD46 | APC | Thermofisher | A15711 | MEM-258 |
| CD55 | APC | Biolegend | 311312 | JS11 |
| CD35 | Alexa Fluor ® 647 | BD | 565329 | E11 |
| CD11b | APC | Invitrogen | 17-0118-42 | ICRF44 |
| CD11c | APC | BD | 333144 | |
| C3aR | APC | Biolegend | 345805 | hC3aRZ8 |
| C5aR | FITC | GeneTex | GTX75734 | P12/1 |
| Streptavidin | APC | eBioscience | 17-4317-82 | |

1.3 Complement activation assay on living Schwann cells

When complement activation was assessed, 50,000 cells were transferred to 96-well v-bottom plates prior to opsonization with 20 μL of the respective opsonizing agent diluted in VB++ (1 h, RT). Next, 100 μL VB++ was added and samples were centrifuged (5 min at 125×g). Next, supernatant was discarded and cells were incubated for 1 h, 37° C. with 100 μL complement active serum (pre-incubated with EDTA, MgEDTA or Abs, 15 min RT). Next, cells were centrifuged for 5 min at 125×g and supernatant was discarded. Subsequently, staining for complement activation was performed according to the staining protocol described above.

1.4 Cytokine Secretion Assay sNF02.2 cells were cultured as described above. After Accutase treatment and counting, cells were transferred to a 24-well plate at a density of 10,000 cells/well in 1 mL sNF02.2 culture medium. After 2 days, culture medium was discarded and cells were opsonized with 100 μL heat-inactivated MMN patient serum at a dilution of 1:50 in VB++ for 1 hr at RT. Next, 100 μL 15% complement active serum (pre-incubated with MgEGTA or antibodies for 15 min at RT) was added to the opsonized cells followed by 1 h incubation at 37° C. Subsequently, 300 μL culture medium was added to the cells resulting in 500 μL final volume/well. After 24 h and 48 h, 200 μL supernatant was collected for in-house analysis by the multiplex core facility of the University Medical Centre in Utrecht (MC Utrecht).

B. Results 1.5 Expression of Complement Receptors by Living Schwann Cells

Figure 1:
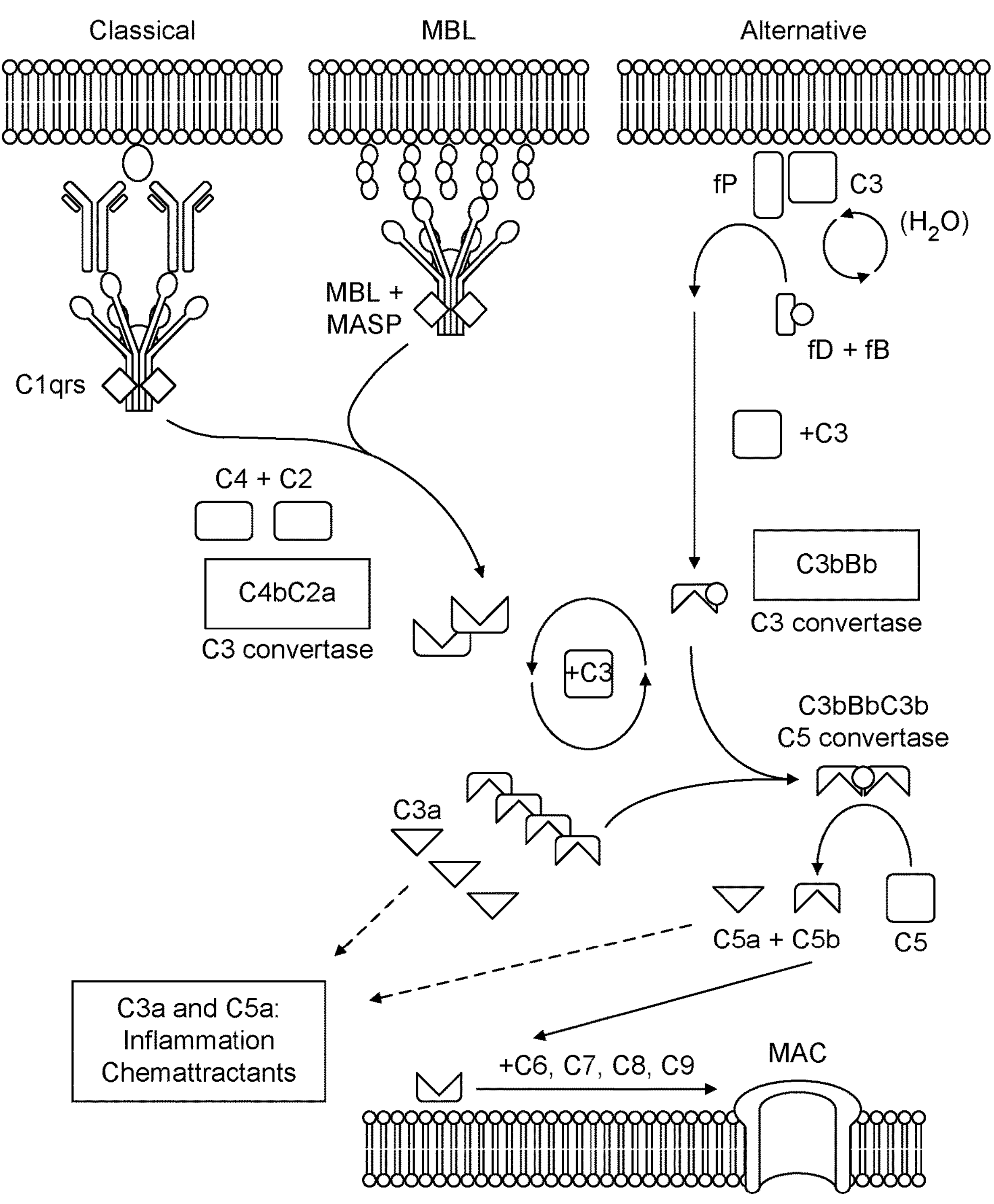
FIG. 1 is a schematic diagram showing the cell signalling cascade involved in the classical, lectin, and alternative pathways of the complement system.
Figure 2:
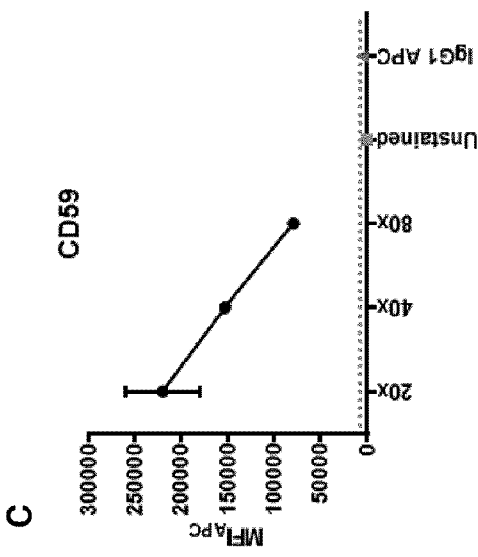
FIG. 2 shows the expression profile of various membrane proteins on living Schwann cells (sNF02.2). Schwann cells were stained for different membrane proteins, particularly proteins associated with the complement cascade, using flow-cytometric analysis. The seven graphs show the following: (A) CD46, (B) CD55, (C) CD59, (D) CD64, (E) CD88, (F) GM1 and (G) MAG.
Figure 2:
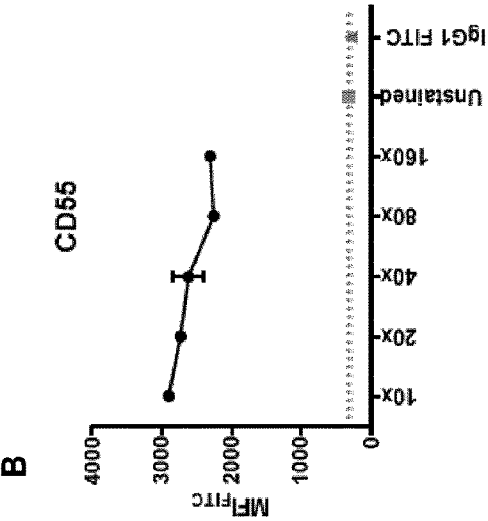
Figure 2:
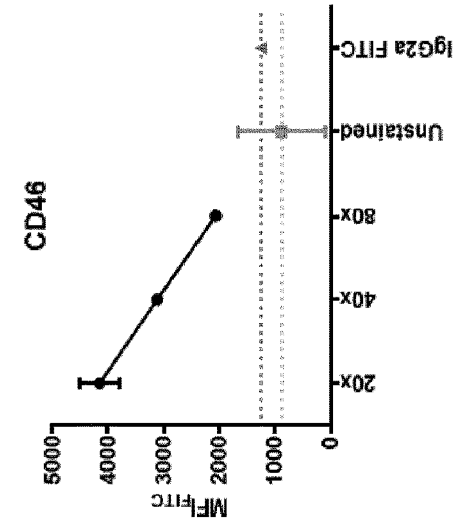
Figure 2:
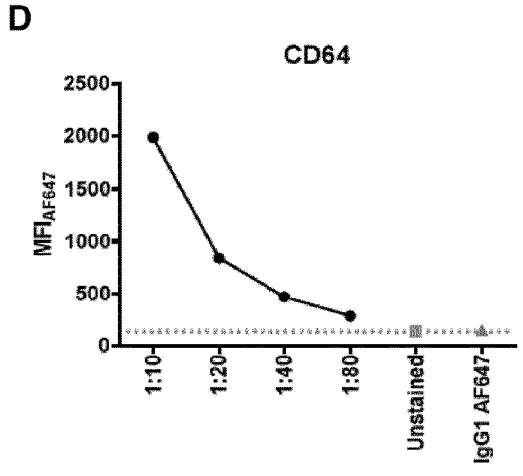
Figure 2:
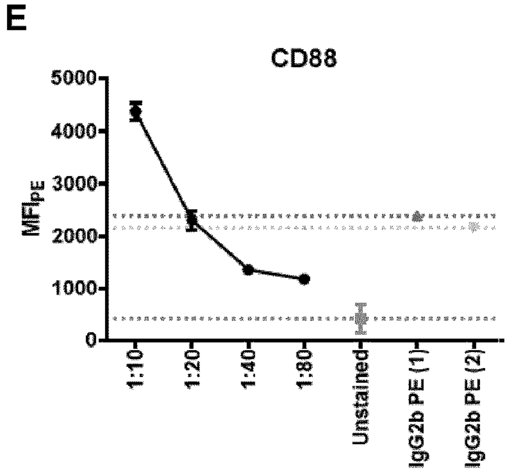
Figure 2:
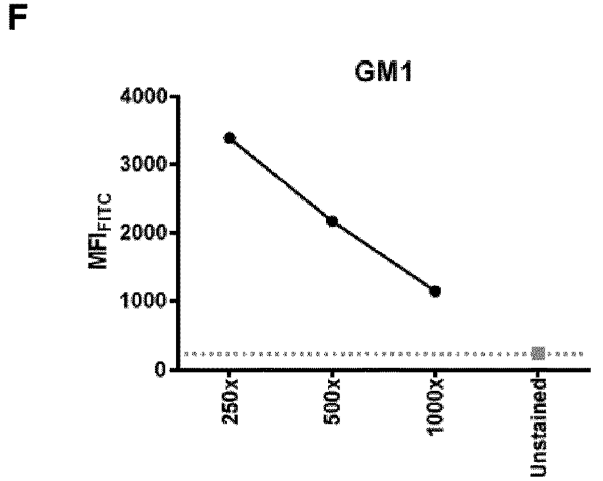
Figure 2:
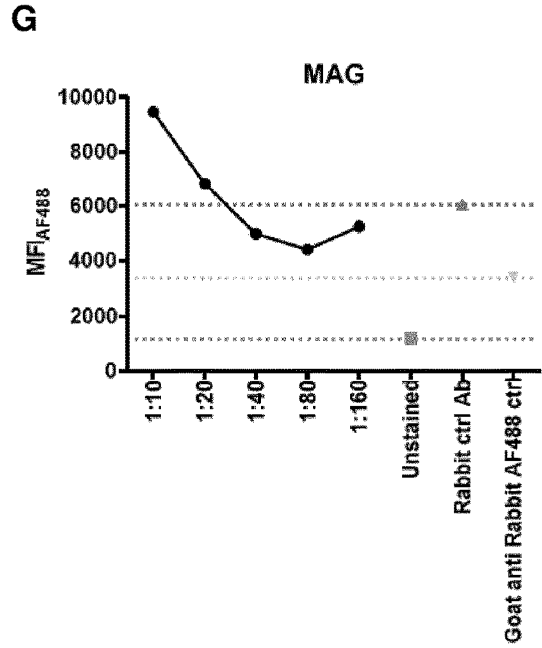

To investigate MMN biology using Schwann cells, expression of complement regulators was assessed. Therefore, sNF02.2 Schwann cells were cultured and FACS staining for expression markers was performed. The results are shown in FIG. 2 and summarized in Table 8 below.

TABLE 8

Expression of complement regulatory proteins on sNF02.2 Schwann cells

| Name | Marker | Schwann cells |
|---|---|---|
| MCP | CD46 | ++ |
| DAF | CD55 | ++ |
| Protectin | CD59 | +++ |
| CR1 | CD35 | − |
| C5aR | CD88 | − |
| C3aR | | + |
| GM1 | | ++ |
| MAG | | + |
| FcγRI | CD64 | ++ |

These results reveal that complement regulatory proteins (CD46, CD55 and CD59) are expressed on Schwann cells, with high expression of the key regulator of the terminal pathway CD59. High CD59 expression on Schwann cells suggests that complement-mediated lysis is limited in these cells because formation of MAC is inhibited. Instead, inflammation is induced in the nerve compartment through cell signaling. Also, Schwann cells showed expression of Fcγ Receptor 1 (CD64) responsible for phagocytotic clearance. No detection of CR1 (CD35) was observed as CR1 expression on Schwann cells occurs with myelination onset and these cultured sNF02.2 Schwann cells lack myelin (Terenghi F et al., *Neurology,* 2004, 62: 666-668). C3aR only showed low expression and C5aR was absent. To conclude, Schwann cell highly express CD59 suggesting sub-lytic formation of MAC triggering inflammation within the nerve compartment.

Figure 3:
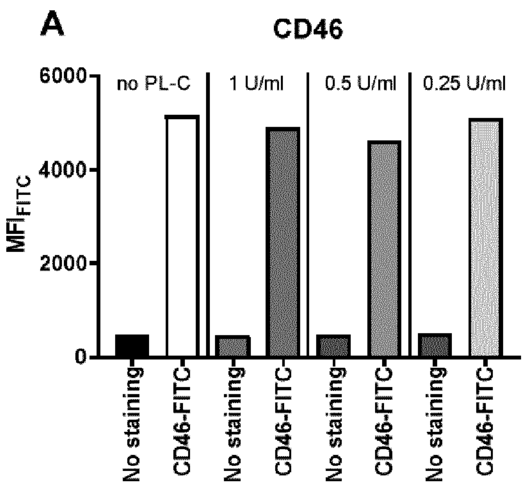
FIG. 3 shows the expression profile of CRPs on sNF02.2 Schwann cells with or without treatment with phospholipase-C (PL-C). sNF02.2 Schwann cells were treated with different concentrations of PL-C (1-0.5-0.25 U/mL) and incubated for 1 h at 37° C. prior to staining with antibodies detecting CD46 (A), CD55 (B) and CD59 (C), respectively.
Figure 3:
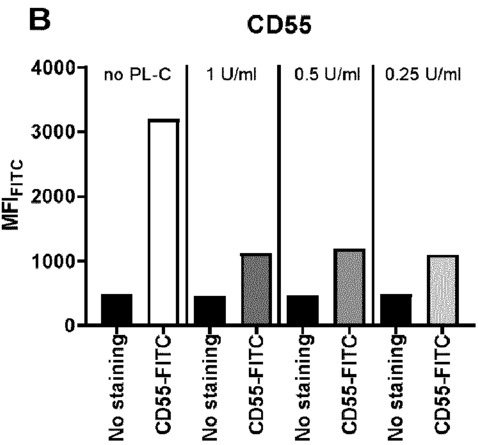
Figure 3:
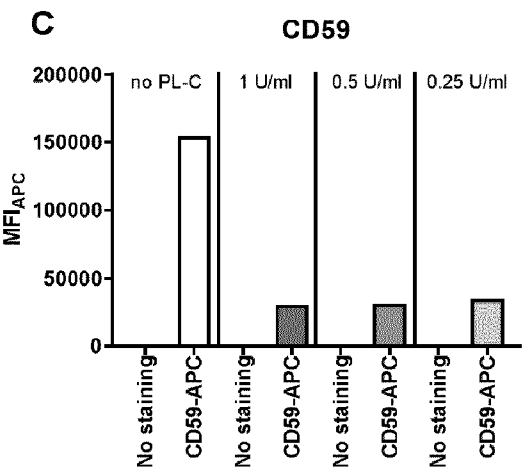

To investigate the sensitivity of complement regulatory proteins (CRP) on Schwann cells to complement mediated lysis, sNF02.2 cells were treated with different concentrations of phospholipase-C (PL-C), which cleaves off glycosylphosphatidylinositol-anchored proteins including CD59 (Fitzpatrick A, Mann C et al., J Peripher Nerv Syst, 2011, 16(2): 84-91). The results are shown in FIG. 3 and demonstrate that both CD55 and CD59 are sensitive to complement mediated lysis as expression levels of both CRPs were decreased upon PL-C treatment.

1.6 Resistance of Schwann Cells to Complement Mediated Cell Lysis

Figure 4:
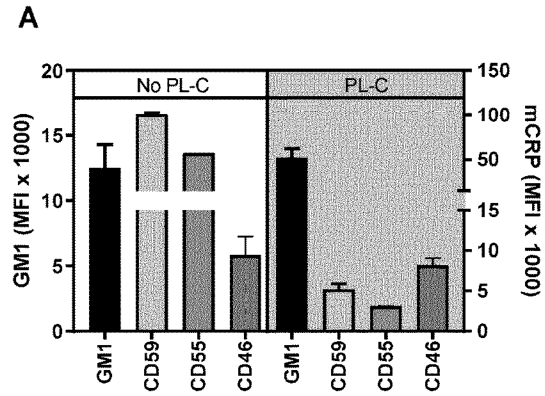
FIG. 4 shows the resistance of Schwann cells (sNF96.2) to complement mediated lysis. Each of the graphs of FIG. 4 shows ‘no PL-C treatment’ on the left half of the graph and ‘PL-C treatment’ on the right half of the graph.
Figure 4:
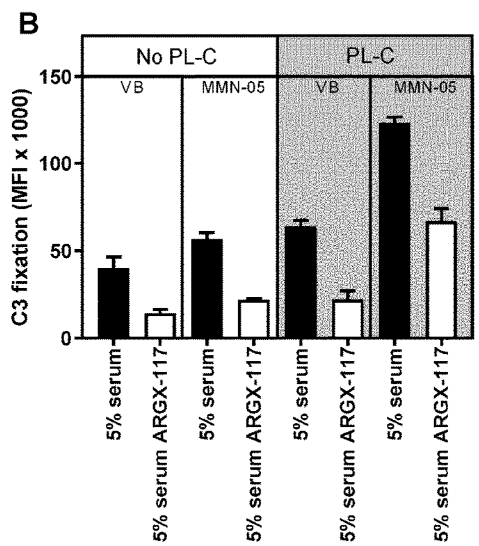
Figure 4:
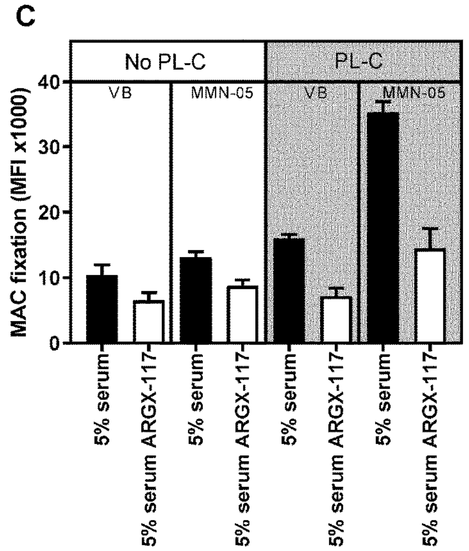
Figure 4:
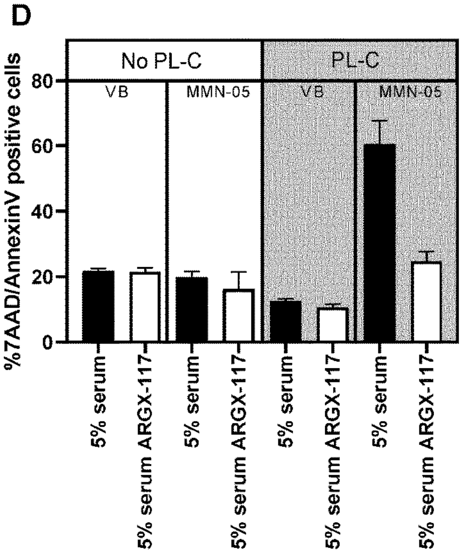

Previous experiments have shown high expression of CD59 and CD55 on Schwann cells (sNF92.2 and sNF02.2). To investigate functional implications of this expression, anti-GM1 mediated C3 and MAC fixation on sNF96.2 Schwann cells with or without CD59 and CD55 was assessed. Also, the effect of complement activation on cell viability was investigated. To this end, Schwann cells were cultured and transferred to a v-bottom plate for further experimental analysis. Treatment with phospholipase C (PL- C) is commonly used to remove GPI-linked proteins, such as CD59 and CD55, from the cell surface. Indeed, PL-C treatment resulted in the removal of CD59 and CD55 while surface expression of CD46 and GM1 remained unaffected (FIG. 4A). To assess effects of PL-C treatment on sensitivity to C3 and MAC fixation, Schwann cells were opsonized with MMN-patient serum (1 hr RT) containing anti-GM1 antibodies, or veronal buffer (VB) as control. Next, cells were incubated with 5% complement active serum or 5% complement active serum pre-incubated with 480 μg/ml ARGX-117 for 1 hour at 37° C. Finally, C3 and MAC fixation were detected using biotin labelled antibodies against C3 and MAC, respectively and stained by APC-conjugated streptavidin. Results are depicted in FIG. 4A and reveal that C3 fixation was slightly increased after opsonization with MMN-05 serum compared to opsonization with VB only in non-PL-C treated Schwann cells. However, ARGX-117 fully inhibited C3 fixation in both conditions. Classical pathway mediated complement activation in VB control is presumably caused by antibodies present in complement active serum (e.g. anti-HLA antibodies). Upon PL-C treatment, increased C3 fixation was observed and ARGX-117 did inhibit C3 fixation induced by MMN-005 serum on PL-C-treated cells, although not completely (FIG. 4B). In this condition high opsonization density is expected and reached by IgM antibodies directed against GM1 and IgM/IgG antibodies against non-GM1 targets regulating in strong complement activation due to the lack of mCRPs. Similar observations were found for MAC fixation where untreated cells displayed low levels of MAC fixation which also slightly increased after opsonization with MMN-005 serum. PL-C treatment led to increased MAC fixation after opsonization with MMN-005 serum, which was inhibited by ARGX-117 (FIG. 4C). Finally, to assess induction of complement-mediated cytotoxicity (CDC), viability was measured by staining with 7AAD combined with annexin-V, and double positive cells were considered late apoptotic/dead. No CDC was detected using cells expressing normal levels of complement regulatory proteins even after opsonization with MMN-005 serum. However, PL-C treatment increased apoptosis in MMN-05 opsonized cells and addition of ARGX-117 resulted in full protection against complement-mediated cell lysis (FIG. 4D). To conclude, Schwann cells are intrinsically protected against complement mediated lysis due to high expression levels of CD59 and CD55. In the absence of mCRPs, CDC was detected which could (partially) be prevented by ARGX-117.

1.7 Detection of Complement Activation Using Schwann Cells

To investigate complement activation on living Schwann cells, cells were transferred to a 96-well v-bottom plate (50,000 cells/well) and opsonized with an anti-HLA antibody (W6/32—BioLegend; Cat No 311402) for 30 min at RT. Next, complement-active serum (pre-incubated with either EDTA, MgEGTA or TNT009, 15 min, RT) was added to the cells at a final concentration of 5% serum. After 1 h incubation (37° C.) cells were transferred into 96-well V-bottom plates and C3 fixation was measured after staining (45 min, ice). The results are shown in FIG. 5.

These results demonstrate C3 fixation after activation of complement with 5% HPS (human pooled serum). Moreover, C3 fixation was complement specific because C3 fixation decreased to basal levels upon addition of EDTA (10 mM) or TNT009 (480 mg/mL). Moreover, C3 was also blocked in presence of MgEDTA, ruling out that it occurred primarily via the alternative complement pathway. Remarkably, C3 fixation was independent of opsonization with W6/32.

1.8 Binding of MMN-Patient Derived Autoantibodies to Cultured Schwann Cells

Before determining the pathogenicity of IgM anti-GM1 antibodies, binding of these antibodies to human Schwann cells in vitro was investigated. To this end, sNF02.2 Schwann cells were cultured and transferred to 96-well round bottom plates (50,000 cells/well) in 50 μL sNF02.2 culture medium. Next, cells were stained with cholera toxin B-AF488 to detect GM1 expression. The results depicted in FIG. 6A show that in vitro cultured human sNF0.2.2 Schwann cells express GM1. Moreover, incubation with MMN patient serum (containing autoantibodies against GM1) resulted in higher anti-GM1 expression and more importantly, IgM binding to Schwann cells was detected after opsonization with MMN-patient serum (FIG. 6B). Different sera of MMN patients were investigated with a wide range of IgM anti-GM1 antibody titers and all demonstrated IgM binding to Schwann cells. Moreover, a titration effect of IgM binding on Schwann cells was detected for all investigated patient sera (FIG. 7).

Next, complement activating potential of patient IgM anti-GM1 antibodies on Schwann cells was evaluated. To this end, human sNF02.2 Schwann cells were transferred to a 96-well v-bottom plate (50,000 cells/well) and opsonized with MMN-patient sera (1 h, RT). Next, complement-active serum was added (1 h, 37° C.) prior to detection of C3 using a FITC-conjugated antibody. At first, only limited C3 fixation was observed due to inadequate C3 detection with the antibody used. Therefore, different approaches were used to increase C3 detection and to lower background complement activation. First, different percentages of complement active sera were tested (10%, 5% and 2.5%) and pre-incubated with 200 μg/mL anti-C5 mAb (1 h, 37° C.) to prevent terminal complement pathway activation and thus to prevent lysis of sNF02.2 Schwann cells. In order to lower complement background, a condition with cleared serum (=complement active serum incubated on Schwann cells for 4×10 min at 4° C. to remove antibodies within the serum) was also tested.

The results depicted in FIGS. 8A and 8B show no difference between complement active serum (back bars) versus cleared serum (grey bars) suggesting that antibodies still present in the serum did not contribute to complement activation and thus C3 fixation. EDTA (white bars) was used as a control. However, the use of 5% complement active serum seemed optimal as the window between no opsonization versus opsonization was greatest. Secondly, different anti-C3 antibodies were tested to increase the window of detection. The results are presented in FIG. 8C and showed an improvement from 10% to 25% window using a biotinylated anti-C3 (LSBio, clone 6C9) to detect C3 fixation on Schwann cells.

Thus, optimal detection of C3 fixation on Schwann cells was observed when complement active serum was used at a final concentration of 5% and with a biotinylated anti-C3 detection antibody from LSBio (clone 6C9). To conclude, C3 fixation is detected on Schwann cells after opsonization with MMN patient serum. This indicated that IgM anti-GM1 antibodies present in MMN patients' sera can activate the classical complement pathway.

1.9 C2-Dependency

C2 dependency was evaluated to verify the importance of complement factor C2 in the pathogenesis of MMN. sNF02.2 Schwann cells were opsonized with MMN patient serum and subjected to C2-depleted serum (Complement Technology; Cat No. A312) reconstituted with increasing concentrations of recombinant human C2, rhC2, (U-protein express; Cat No: C001, 1987) to evaluate C3 fixation. The results are shown in FIG. 9 and revealed that C2-depleted serum alone resulted in relatively high mean fluorescence intensity (MFI) values—MFI signal was higher compared to EDTA control, resulting in a small experimental window. Regardless of that, serum reconstituted with 30 μg/mL rhC2 restored C3 fixation on Schwann cells back to normal levels. Moreover, C3 fixation was restored around 5-10 μg/mL rhC2, which corresponded to 20-40% of physiological C2 levels. These results indicate that low levels of C2 do not lead to C3 fixation or complement activation.

1.10 Efficacy of ARGX-117 in Inhibition of C3 Fixation on sNF02.2 Schwann Cells

Various inhibitory monoclonal antibodies against complement factors have been generated and some of them are approved for clinical applications. For example, TNT009 (BIVV009) is an anti-C1s humanized antibody which specifically blocks the classical complement pathway (Jäger U, D'Sa et al., *Blood,* 2019, 133(9): 893-901), whereas OMS646 targets MASP-2 thereby blocking the lectin pathway. Eculizumab inhibits C5 and thus blocks MAC deposition induced by all three pathways (Brodsky R, Young N et al., *Blood,* 2018, 111: 1840-1847).

ARGX-117 is a monoclonal antibody targeting C2 and is unique because it inhibits the classical and lectin pathway whilst leaving the alternative pathway intact. The results above demonstrate that IgM anti-GM1 auto-antibodies in serum from MMN patients can specifically bind to sNF02.2 Schwann cells. Moreover, the autoantibodies are able to activate the complement cascade resulting in C3 fixation on Schwann cells. The effect of ARGX-117 on C3 fixation mediated by MMN sera was studied to evaluate the therapeutic potential of this antibody. To this end, Schwann cells were cultured and transferred to a v-bottom plate (50,000 cells/well), opsonized with MMN-patient serum (1 h, RT) and subsequently incubated with 5% complement active serum which was pre-incubated with complement blocking antibodies or EDTA (20 min, RT). Detection of C3 fixation was performed by staining Schwann cells with C3-BIO (LSBio, clone 6C9) and streptavidin-APC. The results are shown in FIG. 10.

The results revealed that C3 fixation was inhibited in a dose-dependent way by both ARGX-117 and TNT009. However, inhibition of both antibodies did not reach EDTA control. TNT009 could block C3 fixation up to 53 μg/mL whilst higher concentrations of ARGX-117 were needed to block at the same extent (160 μg/mL). Importantly, anti-C5 was not added to the cells, which was previously done to block the terminal complement pathway in order to be able to detect C3 fixation. Surprisingly cells were not lysed, meaning that they are intrinsically protected against complement mediated lysis, probably due to high expression of CD59 on Schwann cells. To conclude, ARGX-117 is able to block C3 fixation on Schwann cells in a dose dependent manner and these cells are intrinsically protected against complement-mediated lysis.

1.11 Cytokine Secretion Assay

To unravel the pathophysiology on the origin of nerve damage in MMN patients, complement-mediated cytokine production was measured. Schwann cells were seeded into 24-well plates (10,000 cells/well), opsonized with MMN-patient serum (1 h, RT) and complement active serum was added in the presence or absence of complement blocking antibodies. After 48 h, supernatant was collected and cytokine secretion was measured using the Luminex platform. The results are shown in FIG. 11 and demonstrate that stimulation of Schwann cells with IL1-β or TNF-α results in increased secretion of IL-6, IL-8 and MCP-1. In MMN-patient sera no elevation of either IL-6 or IL-8 was observed. Nevertheless, MCP-1 levels in cells incubated with MMN-patient sera were increased 2-fold relative to controls (FIG. 11C). This increase could be blocked upon addition of ARGX-117 or TNT009, whereas eculizumab could only partially block MCP-1 secretion.

MCP-1 plays a role in recruitment of inflammatory immune cells, monocytes, and macrophages to the site of infection and is also involved in the pathogenesis of several diseases including neuro-inflammatory processes which are characterised by neurological degeneration. For example, circulating levels of MCP-1 are increased upon GBS progression (Orlikowski et al, J of neuroimmunol, 2003, 134 (118-27))). To conclude, MCP-1 is produced by sNF02.2 Schwann cells following opsonization with MMN patient sera and subsequent complement activation. ARGX-117 was able to block MCP-1 production.

C. Conclusion

Regulation of the complement system was evaluated using sNF02.2 Schwann cells. The data demonstrate that Schwann cells express high levels of the complement regulatory proteins CD46, CD55 and CD59. Moreover, it was shown that IgM anti-GM1 antibodies from MMN-patients activate the classical complement pathway and that C3 fixation was dependent on the presence of C2 in the MMN model system studied. ARGX-117 efficiently blocked complement activation on sNF02.2 cells sensitized with anti-GM1 antibodies.

These results suggest a new mechanism by which complement events triggered by anti-GM1 autoantibodies contribute to pathology in MMN patients. This is depicted schematically in FIG. 12. IgM anti-GM1 autoantibodies activate the classical complement pathway, but due to high expression of CD59 on Schwann cells, lytic MAC is not formed. Direct complement-dependent cytotoxicity (CDC) is therefore an unlikely mechanism that contributes to neurological damage in this condition. However, sub-lytic MAC complex formation has been described to cause cellular activation which may induce production and secretion of inflammatory mediators. In the present study, complement-dependent production of chemokine MCP-1 by sNF02.2 cells was observed. Eculizumab, anti-C5, was not able to inhibit MCP-1 secretion in one out of two MMN sera tested, which suggests that the MCP-1 secretion by sNF02.2 cells is triggered by mechanisms upstream of sub-lytic MAC formation.

It is likely that complement activation by anti-GM1 antibodies induces release of cytokines and/or chemokines through C3aR, which was found to be expressed on these cells. These chemokines, such as MCP-1, may play a role in attracting inflammatory cells leading to further neuronal dysfunction and damage. Here, complement activation by anti-GM1 antibodies on Schwann cells led to MCP-1 secretion which was inhibited by ARGX-117, suggesting a possible therapeutic mechanism of this antibody. To conclude, the pathophysiology of nerve destruction and demyelination in MMN patients appears to take place upstream of MAC formation, which makes components of the complement cascade upstream of MAC more interesting therapeutic targets for treating this disease. ARGX-117 targets the C2 complement protein and is thus an example of a suitable molecule to treat this indication.

Example 2 Complement Inhibition in an In Vitro Model of Multifocal Motor Neuropathy (MMN) Using Fixed Schwann Cells A. Methods 2.1 Protocol for Culturing and Fixing Schwann Cells on Cover Slips Schwann cells were cultured in DMEM medium completed with 100 U/mL penicillin, 100 μg/mL streptomycin and supplemented with 10% FCS at 37° C. at 5% $CO_2$. Twice a week, when confluency had reached >80%, cells were passaged or used in experiments. Medium was discarded and cells were washed with 10 ml PBS. To dissociate the cells, 3 mL (T75) or 5 mL (T175) Accutase cell detachment solution was added, and cells were incubated at 37° C. for 5 min, or until cells fully detached. Then, culture medium (7 mL to T75 and 10 mL to T175) was added and cells were transferred to 15 mL tubes prior to centrifugation (125×g, 10 min). Pellets were resuspended in 5 ml culture medium and counted using trypan blue to discriminate viable cells from dead cells. Next, cells were adjusted to the desired concentration and seeded into culture flasks (10 mL in T75, 20 mL in T175) or seeded onto coverslips which were placed into 24-well plates.

2.2 Protocol for In Vitro Evaluation of ARGX-117 sNF02.2 Schwann cells were cultured for 3 days on coverslips at 37° C., 5% $CO_2$. Cells were fixed using 4% PFA, (10 min at 4° C.), washed once with 500 μL PBS and the coverslips were removed from 24-well plates. To minimize non-specific staining, cells were quenched using 100 μL $NH_4Cl$ for 5 min at RT, washed once with 100 μL PBS followed by blocking with 100 μL PBS+2% BSA for 2 h at RT. After washing with 100 μL PBS, cells were incubated top-down with heat-inactivated MMN patient sera, diluted 1:50 in PBS+2% BSA, for 60 min. Next, cells were washed once (500 μL PBS+2% BSA), incubated top-up with 15% complement active serum (−/+ pre-incubation with complement blocking antibodies) for 30 min at RT and washed once (100 μL PBS+2% BSA). Subsequently, cells were stained with 100 μL primary antibodies (diluted in PBS+2% BSA) and incubated top-down (1 h, RT, dark) prior to washing with 100 μL PBS+2% BSA. Next, cells were incubated top-down with 100 μL Streptavidin-APC (1:100 diluted in PBS+2% BSA) for 1 h at RT in the dark followed by washing once with 100 μL PBS and once with 100 μL MilliQ water. After drying coverslips on a tissue, 7 μL ProLong™ Diamond Antifade Mountant with DAPI was pipetted on the coverslips, dried overnight at 4° C., before fixing with nail polish. Cells were analyzed using a Zeiss Z1 microscope with Colibri LEDs with the following settings: 40× magnification, 25% LED, 400 ms for Alexa Fluor™ 488 channel, 100 ms for APC channel and 50 ms for DAPI channel. Antibodies used for staining are shown in Table 9 below.

TABLE 9

Staining antibodies

| Antibody | Label/ Fluoro-chrome | Company | Cat. N° | Dilation Factor |
|---|---|---|---|---|
| Polyclonal goat anti-human C4 | Biotin | MyBioSource | MBS560216 | 1:100 |
| Polyclonal sheep anti-human C3 [(1)] | Biotin | MyBioSource | MBS560642 | 1:100 |
| Anti-C5b-9 [(2)] | Biotin | Novus Bio | NBP2-23494 | 1:500 |
| Streptavidin | APC | ThermoFisher eBioscience ™ | 17-4317-82 | 1:100 |
| Cholera Toxin Subunit B | Alexa Fluor ™ 488 | ThermoFisher | C34775 | 1:500 |
| Anti-human C3 clone 9 | Biotin | Sanquin | MW1830 | 1:100 |
| Anti-human C3 clone 28 | Biotin | Sanquin | MW1860 | 1:100 |
| Goat anti-human IgM μ-chain | Biotin | Sigma Aldrich | B1265 | 1:300 |
| CD46 | APC | ThermoFisher | A157711 | 1:50 |
| CD55 | APC | BioLegend | 311312 | 1:25 |
| CD59 | APC | Life technologies | 17-0596-42 | 1:50 |
| Goat anti mouse IgG | AF647 | Invitrogen | A21235 | 1:400 |
| GM1 | AF488 | Invitrogen | C34775 | 1:500 |

(1) Reacts with both human C3a and C3b.

(2) Anti-C5b-9 clone aE11 is directed against a neoepitope exposed on C9 when incorporated into the TCC.

B. Results

For the experiments conducted using fixed Schwann cells, very similar results were observed as reported above in Example 1 using living Schwann cells.

2.3 Expression of Complement Receptors sNF02.2 Schwann cells were cultured and fixed on coverslips prior to staining for expression markers. The results are shown in Table 10 below and reveal that all complement regulatory proteins are expressed on Schwann cells. CD59 is highly expressed, suggesting that motor neurons are protected against MAC-mediated lysis because CD59 is the key regulator of the terminal pathway. CD46, CD55 and C3aR showed moderate expression on Schwann cells, while C5aR was highly expressed on the cell body of Schwann cells. CD35, CD11 b and CD11c were all absent on Schwann cells.

TABLE 10

Expression of complement regulatory proteins on fixed Schwann cells

| Marker | Name | Schwann cells (fixed) |
|---|---|---|
| CD46 | MCP | ++ |
| CD55 | DAF | ++ |
| CD59 | Protectin | +++ |
| CD35 | CR1 | − |
| CD88 | C5aR | ++ |
| C3aR | | + |
| GM1 | | ++ |
| CD11b | CR3 | − |
| CD11c | CR4 | − |

2.4 Binding of MMN Patient-Derived Autoantibodies to Fixed Schwann Cells

The binding of MMN patient-derived autoantibodies to fixed Schwann cells was studied and similar results were seen to those reported in Example 1.8 above.

sNF02.2 Schwann cells were cultured on coverslips (50,000 cells/coverslip) in 1 mL sNF02.2 culture medium for 3 days followed by fixation with 4% PFA. Next, coverslips were washed in PBS and quenched with $NH_4Cl_4$ (5 min., RT) before 2 hours blocking with PBS-2% BSA. Staining with Cholera toxin B—Alexa488 was performed to detect GM1 expression. The results showed that in vitro cultured human sNF0.2.2 Schwann cells express GM1 as well as neuroblastoma derived mouse N2a cells.

Incubation with MMN patient serum resulted in significant anti-GM1 staining co-localized with IgM staining. Different sera of MMN patients were investigated with a wide range of IgM anti-GM1 antibody titers and all demonstrated IgM binding to Schwann cells. Moreover, IgM antibody binding to human Schwann cells was GM-1 specific because incubation with excess amounts of soluble unlabeled cholera toxin interfered with binding of IgM antibodies from MMN sera. Pre-incubation with 100 μg/mL unlabeled cholera toxin efficiently prevented anti-GM1 antibody binding to Schwann cells due to competition of binding between cholera toxin and anti-GM1 antibodies to GM1 gangliosides.

The complement activating potential of patient IgM anti-GM1 antibodies on Schwann cells was evaluated. To this end, human Schwann cells were incubated with heat-inactivated serum from MMN patients (containing autoreactive IgM anti-GM1 antibodies) and HPS (human pooled serum) which functioned as an external complement source. The deposition of complement factors, such as C4 and C3 formation was determined using specific antibodies. The results showed that C4 fixation could be detected on Schwann cells, which was correlated with anti-GM1 titers. However, high IgM anti-GM1 titer was not always associated with high C4 deposition.

Detection of C3 was evaluated and coverslips were stained with different anti-C3 antibodies. Subsequently, Schwann cells opsonized with different MMN patient serum showed C3 fixation on these cells. However, high anti-IgM GM1 titers did not always correlate with high C3 deposition. All EDTA controls were negative.

Table 11 below summarizes different complement factor expression levels of different MMN patient samples.

TABLE 11

C3 and C4 fixation of different MMN-patient samples

| Patient | Anti-IgM GM1 titre* | C3 fixation | C4 fixation |
|---|---|---|---|
| MMN-005 | 1:800 | High | High |
| MMN-014 | 1:0 | Low | Low |
| MMN-017 | 1:800 | Low | Low |
| MMN-024 | 1:6400 | Medium/high | High |
| MMN-035 | 1:100 | Low/medium | Low |
| MMN-042 | 1:1600 | Medium | High |
| MMN-052 | 1:25600 | Low | Low/medium |
| MMN-073 | 1:25600 | Medium/high | high |

*Determined based on GM1 ELISA.

To conclude, C4 and C3 fixation was detected on fixed Schwann cells after opsonization with MMN patient serum. This indicates that IgM anti-GM1 antibodies from MMN patients can activate the classical complement pathway.

2.5 C2 Dependency

C2 dependency was evaluated to verify the importance of complement factor C2 in the pathogenesis of MMN. Therefore, Schwann cells were opsonized with C2-depleted serum and reconstituted with increasing concentrations of purified human C2 (hC2) to evaluate C3 formation. The results revealed no C3 fixation with C2-depleted serum. However, addition of C2 restored C3 fixation in a concentration-dependent manner. Interestingly, no full blockage of C2 was needed to block C3 fixation; 4.58 μg/mL hC2 (about 20% of the physiological levels) hardly showed C3 formation.

To summarize, C3 fixation was dependent on the presence of C2. Complete inhibition of C2 was not needed in order to block the classical complement pathway and thereby prevent C3 formation on Schwann cells.

2.6 Efficacy of ARGX-117 on Fixed Schwann Cells

Schwann cells were cultured for 3 days on cover slips prior to fixation. Subsequently, cells were washed, quenched and blocked followed by patient serum opsonization. Thereafter, cells were incubated with complement-active serum in the presence or absence of different complement blocking antibodies or IVIg for 20 minutes at RT. Finally, cells were stained and imaged using 40× magnification.

C4 fixation on Schwann cells was inhibited by TNT009 (200 μg/mL) as well as with 12.5 mg/mL IVIg treatment.

C3 inhibition was observed with ARGX-117 and TNT009 both used at 200 μg/mL, whereas no effect was seen with eculizumab or OMS646 as anticipated. IVIg at a concentration of 12.5 mg/mL only showed a partial inhibition of C3 fixation on Schwann cells. Thus, high concentrations (200 μg/mL) of complement inhibitory antibodies were able to block C4 and C3 fixation in this in vitro disease model system for MMN.

To determine the differential effects of anti-complement antibodies, a titration was performed and downstream complement events were analyzed. Fixed Schwann cells were opsonized with MMN-patient serum, complement was activated in the presence of increasing concentrations of complement blocking antibodies (TNT009, eculizumab and ARGX-117) starting at 15 μg/mL up to 480 μg/mL. The results showed no inhibitory effect on C3 fixation with eculizumab since it inhibits downstream of C3. ARGX-117 showed full inhibition of C3 fixation until a concentration of approximately 30 μg/mL.

C. Conclusion

The complement inhibitory effect of ARGX-117, targeting human C2b, was evaluated in an in vitro model using fixed Schwann cells, thereby mimicking the pathophysiology of MMN. The data demonstrate that Schwann cells expressed high levels of the complement regulatory proteins CD46, CD55 and CD59. Moreover, it was shown that IgM anti-GM1 antibodies from MMN patients activate the classical complement pathway and that C3 fixation was dependent on the presence of C2 in the MMN model system. ARGX-117 efficiently blocked complement activation and outperformed both eculizumab and TNT009.

Example 3 Complement Inhibition in an In Vitro Model of Multifocal Motor Neuropathy (MMN) Using Induced Pluripotent Stem Cells (iPSCs)

A. Methods 3.1 Protocol for Differentiation of Spinal Motor Neurons from iPSCs

Motor neuron-like cells (MNs) from induced pluripotent stem cells (iPSCs) were prepared as described in the literature (Harschnitz 0 et al. *J Clin Immunol.* 2014, July; 34 Suppl 1:S112-9) and in cooperation with Dr L van der Pol and coworkers, the Department of Neurology, UMCU, The Netherlands. Briefly, human fibroblasts were obtained from skin biopsies from healthy individuals under a protocol approved by the institutional review board. These cells were cultured at 37° C. with 5% $CO_2$ in mouse embryonic fibroblast (MEF) medium containing DMEM GlutaMAX supplemented with 10% fetal bovine serum and 1% penicillin/streptomycin. Cells were reprogrammed within the first 5 passages according to the following protocol. Human fibroblasts were plated at a density of 10,000 cells per well in a 6-well dish and cultured for 24 hours in MEF medium. Subsequently, viral transduction was performed with a mixture containing MEF medium, 4 mg/mL hexadimethrine bromide, and a lentiviral vector expressing Oct4, KIf4, Sox2, and c-Myc. Following a 24-hour incubation, cells were washed 3× with PBS, pH 7.4, and cultured for 5 additional days in MEF medium. Thereafter, cells were incubated with Trypsin-EDTA and transferred to a 10 cm dish, pre-coated with 0.1% gelatin and containing a confluent layer of irradiated MEFs in MEF medium. Culture medium was replaced by human embryonic stem cell (huES) medium containing DMEM-F12, knockout serum replacement, 1% penicillin/streptomycin, L-glutamine, nonessential amino acids, P-mercaptoethanol, and 20 ng/mL recombinant human fibroblast growth factor-basic. Colonies of iPSCs were manually picked after 3 to 6 weeks for further expansion and characterization. iPSCs were maintained in huES medium, cryopreserved after 4 to 6 passages, and stored in liquid nitrogen. iPSCs were cultured on irradiated MEFs in huES medium and passaged manually. Feeder-free culture of iPSCs was performed on Geltrex and maintained in mTeSR1 medium. Feeder-free cultured iPSCs were passaged enzymatically using Accutase.

3.2 Protocol for In Vitro Evaluation of ARGX-117 iPSCs were cultured for 12-14 days on coverslips at 37° C., 5% $CO_2$, towards MNs. Next, iPSC-MNs were fixed using 4% PFA, (10 min at 4° C.), washed 3 times with 500 μL PBS and the coverslips were removed from 24-well plates. To minimize non-specific staining and to neutralize the fixative, cells were quenched using 100 μL 50 mM $NH_4Cl$ for 5 min at RT, washed once in PBS (all washing steps through submerging the coverslip) followed by blocking with 100 μL PBS+2% BSA for 2 h at RT. After washing with PBS, cells were incubated top-down with heat-inactivated MMN-patient sera, diluted 1:50 in PBS+2% BSA, for 60 min. Next, cells were washed once in PBS, incubated top-up with 15% complement active serum (−/+ pre-incubation with complement blocking antibodies) for 30 min at RT and washed once in PBS. Subsequently, cells were stained with 100 μL primary antibodies (diluted in PBS+2% BSA) and incubated top-down (1 h, RT, dark) prior to washing in PBS. Next, cells were incubated top-down with 100 μL Streptavidin-APC (1:100 diluted in PBS+2% BSA) for 1 h at RT in the dark followed by washing once with PBS and once with MilliQ water (also submerging the coverslip). After drying coverslips on a tissue, 7 μL ProLong™ Diamond Antifade Mountant with DAPI was pipetted on the object glass and coverslips were placed top-down on the drop and dried overnight at RT, before fixing with nail polish. Cells were analyzed using a Zeiss Z1 microscope with Colibri LEDs with the following settings: 40× or 20× magnification (depending on the experiments), 25% LED, 400 ms for Alexa Fluor™ 488 channel, 100 ms for APC channel and 50 ms for DAPI channel (unless otherwise indicated). Four pictures were taken per condition throughout the whole coverslip. All pictures were normalized on the positive and negative control and exported in single and merged channel to non-compressed 8-bit TIFF-format using ZEN 2012 software. Mean Gray Value was calculated of each single channel with Image J (Fiji). Ratios were calculated in Microsoft Excel 2010 and visualized using GraphPad Prism 7. Antibodies used for staining are shown in Table 12 below.

TABLE 12

Staining antibodies

| Antibody | Label/ Fluoro-chrome | Company | Cat. N° | Dilation Factor |
|---|---|---|---|---|
| Polyclonal goat anti-human C4 | Biotin | MyBioSource | MBS560216 | 1:100 |
| Polyclonal sheep anti-human C3 (1) | Biotin | MyBioSource | MBS560642 | 1:100 |
| Anti-C5b-9 (2) | Biotin | Novus Bio | NBP2-23494 | 1:500 |
| Streptavidin | APC | ThermoFisher eBioscience ™ | 17-4317-82 | 1:100 |
| Cholera Toxin Subunit B | Alexa Fluor ™ 488 | ThermoFisher | C34775 | 1:500 |
| Anti-human C3 clone 9 | Biotin | Sanquin | MW1830 | 1:100 |
| Anti-human C3 clone 28 | Biotin | Sanquin | MW1860 | 1:100 |
| Goat anti-human IgM μ-chain | Biotin | Sigma Aldrich | B1265 | 1:300 |
| CD46 | APC | ThermoFisher | A15711 | 1:50 |
| CD55 | APC | BioLegend | 311312 | 1:50 |
| CD59 | APC | Life technologies | 17-0596-42 | 1:50 |
| Goat anti mouse IgG | AF647 | Invitrogen | A21235 | 1:400 |
| GM1 | AF488 | Invitrogen | C34775 | 1:500 |
| CD35 | APC | BD | 565329 | 1:50 |
| CD11b | APC | Invitrogen | 17-0118-42 | 1:50 |
| CD11c | APC | BD | 333144 | 1:50 |
| C3aR | APC | Biolegend | 345805 | 1:50 |
| C5aR | FITC | GeneTex | GTX75734 | 1:50 |
| Polyclonal rabbit anti-human IgM | | Dako | A0425 | 1:1000 |
| Poly Swine anti-Rabbit Ig | HRP | Dako | P0217 | 1:10000 |

(1) Reacts with both human C3a and C3b.

(2) Anti-C5b-9 clone aE11 is directed against a neoepitope exposed on C9 when incorporated into the TCC.

3.3 Protocol to Determine GM1 Using ELISA

NUNC maxisorp plates were coated with GM1 (5 μg/mL) in methanol. The methanol was evaporated for +/−2.5 h in a laminar flow cabinet. Subsequently, wells were blocked with 200 μL 1% BSA-PBS for 2 h at RT. MMN patient sera was diluted in 1% BSA-PBS (either preincubated with IVIg) and 100 μL was added to each well followed by O/N incubation at 4° C. Next, plates were washed 6 times with PBS followed by incubation with the primary antibody detecting human IgM in 1% BSA-PBS (1 h at RT). After six washing steps with PBS, wells were incubated with 100 μL HRP-conjugated secondary antibody for 1 h at RT. After six washing steps with PBS, TMB was added and the reaction was stopped using hydrochloric acid. Plates were analyzed at 415 nm using a BioRad ELISA reader.

B. Results

To investigate the pathogenicity of anti-GM1 IgM antibodies of MMN patients, an in vitro model for MMN was developed, as currently no animal model for MMN is available. In brief, human induced pluripotent stem cells were generated from fibroblasts and differentiated into motor neurons as described above. Next, these motor neurons were fixed on coverslips using paraformaldehyde (PFA) and quenched with $NH_4Cl$. Subsequently, cells were opsonized using MMN patient serum, which contains anti- GM1 IgM autoantibodies, for 1 hour allowing binding of these autoantibodies to GM1. After washing, complement was activated using human pooled serum (HPS) in the presence or absence of complement blocking antibodies for 30 minutes. Finally, cells were stained with antibodies against complement factors to evaluate complement activity. The results of these studies are described below.

3.4 Expression of Complement Receptors on iPSC Derived Motor Neurons

To better understand the role of complement in the pathophysiology of MMN, expression of complement regulatory proteins and complement receptors was assessed on iPSC-MNs. Therefore, iPSC-MNs were cultured and fixed using 4% PFA on coverslips prior to staining for expression markers. The results are shown in Table 13 and FIG. 13.

TABLE 13

Expression of complement regulatory proteins on iPSC-MNs

| Marker | Name | iPSC derived motor neurons |
|---|---|---|
| CD46 | MCP | ++ |
| CD55 | DAF | ++ |
| CD59 | Protectin | +++ |
| CD35 | CR1 | + |
| CD88 | C5aR | ++ |
| C3aR | | ++ |
| GM1 | | +++ |
| CD11b | | − |
| CD11c | | − |

These results reveal that all complement regulatory proteins (CD46, CD55 and CD59) are expressed on fixed motor neurons. CD59 is highly expressed suggesting that motor neurons are protected against MAC mediated lysis. CD46 and CD55 showed intermediate expression localized to the cell body. Both C3R and C5R are expressed on motor neurons with C5aR only expressed on the cell body, not on the neurites. CD11 b and CD11c were both absent while CD35 expression was low.

3.5 Binding of MMN Patient-Derived Autoantibodies to iPSC-MNs

Binding of IgM anti-GM1 antibodies to iPSC-MNs was investigated in vitro. To this end, iPSC-MNs were cultured on coverslips (80,000-150,000 cells/13 mm coverslip) in 1200 μL culture hMN medium for 12-14 days followed by fixation with 4% PFA. Next, coverslips were washed in PBS and quenched with $NH_4Cl_4$ (5 min, RT) before 2 hours blocking with PBS-2% BSA. Staining with Cholera toxin B-Alexa 488 was performed to detect GM1 expression. The results showed that motor neurons derived from iPSCs express GM1 and incubation with MMN patient serum resulted in significant anti-GM1 staining co-localized with IgM staining.

The complement activating potential of patient IgM anti-GM1 antibodies on iPSC-derived motor neurons was also evaluated. To this end, human iPSC-derived motor neurons were incubated with heat-inactivated serum from MMN patients (containing autoreactive IgM anti-GM1 antibodies) and HPS which functioned as an external complement source. The deposition of complement factors, such as C4 and C3 was determined using specific antibodies. The results showed that C4 and C3 fixation could be detected on iPSC-MNs. However, high anti-IgM GM1 titers did not always correlate with high C3 deposition. To conclude, C4 and C3 fixation was detected on fixed iPSC-MNs after opsonization with MMN patient serum. This indicates that IgM anti-GM1 antibodies from MMN patients can activate the classical complement pathway.

3.6 C2-Dependency

C2 dependency was evaluated to verify the importance of complement factor C2 in the pathogenesis of MMN. iPSC-derived motor neurons were opsonized with C2-depleted serum and reconstituted with increasing concentrations of purified human C2 (hC2) to evaluate complement activation by measuring C3 fixation. The results are shown in FIG. 14 and revealed no C3 fixation with C2-depleted serum. However, addition of C2 restored C3 fixation in a concentration-dependent manner. Moreover, ARGX-117 fully inhibited C3 fixation in C2-depleted serum reconstituted with physiological amounts of hC2.

To summarize, C3 fixation is dependent on the presence of C2. This is demonstrated by the ability of ARGX-117 to inhibit C3 fixation in the presence of hC2. It appears that complete inhibition of C2 is not needed in order to block the classical complement pathway and prevent C3 formation.

3.7 Efficacy of ARGX-117 to Prevent Complement Fixation on Fixed iPSC-MNs

As described in section 1.9 above, various inhibitory monoclonal antibodies against complement factors have been generated and some of them are approved for clinical applications. The effect of these inhibitory antibodies was studied on fixed iPSC-MNs. To this end, iPSC-MNs were cultured for 12-14 days on cover slips prior to fixation. Subsequently, cells were washed, quenched and blocked followed by patient serum opsonization. Thereafter, cells were incubated with complement active serum in the presence or absence of different complement blocking antibodies for 20 minutes at RT. Finally, cells were stained and imaged using 40× or 20× magnification.

C4 fixation on motor neurons was inhibited by TNT009 (200 μg/mL) and not by other mAbs as expected.

C3 inhibition was observed with ARGX-117 and TNT009 both used at 200 μg/mL, whereas no effect was seen with eculizumab, OMS646 and rituximab used at the same concentration. Thus, high concentrations (200 μg/mL) of ARGX-117, blocking C2, were able to block downstream C3 fixation in this in vitro disease model system for MMN.

To determine the differential effects of anti-complement antibodies, a titration was performed and downstream complement events were analyzed. Fixed iPSC derived motor neurons were opsonized with MMN-patient serum. Complement active serum was pre-incubated with increasing concentrations of complement blocking antibodies (TNT009, OMS646 and ARGX-117) starting at 3 μg/mL up to 200 μg/mL before being added to the iPSC-MNs. The results showed no inhibitory effect on C3 fixation with OMS646 since it inhibits the lectin pathway. ARGX-117 showed full inhibition of C3 fixation until a concentration of approximately 12 μg/mL. The same results were obtained with TNT009 where C3 deposition was also blocked until 12 μg/mL. Thus, ARGX-117 and TNT009 performed equally well in inhibiting C3 fixation on iPSC derived motor neurons opsonized with MMN-patient serum.

3.8 Complement Inhibition by ARGX-117 in Other Immune-Mediated Neuropathies

Autoimmune peripheral neuropathies represent a clinically heterogeneous group of rare and disabling diseases characterised by motor and/or sensory symptoms of disease severity. In MMN these is direct evidence for autoimmune reactivity, mediated by specific IgM antibodies targeting GM1. Other immune-mediated neuropathies have been identified including chronic inflammatory demyelinating polyradiculoneuropathy (CIDP) as the most common and Guillain-Barré Syndrome (GBS) as the most acute disorder. To evaluate therapeutic effects of ARGX-117 on other immune-mediated neuropathies, the above described in vitro model was used. However, instead of opsonizing iPSC-derived motor neurons with MMN-patient serum, sera from GBS and CIDP patients were used, respectively. Results are depicted in FIG. 15 and revealed that autoantibodies present in both patient sera could activate complement, measured as C3 fixation on motor neurons, and this was blocked by addition of 200 μg/mL ARGX-117. Thus, in addition to MMN, ARGX-117 also blocked complement in a disease model for other immune mediated neuropathies.

3.9 Effect of IVIg on Complement Inhibition Using the In Vitro MMN Assay

IVIg are biological agents frequently used for the treatment of various autoimmune diseases. In MMN, IVIg is FDA-approved and first line treatment. Several mechanisms are responsible for immune modulation with IVIg including direct neutralization of pathogenic immunoglobulins, FcR blockade and regulation of several immune cells. IVIg also acts on inhibition of complement activation as IgG, present in IVIg, can bind to C3 thereby depleting C3 from the serum and preventing the terminal complement pathway (Terenghi F et al., *Neurology,* 2004, 62: 666-668; Fitzpatrick A, Mann C et al., *J Peripher Nerv Syst,* 2011, 16(2): 84-91). In MMN it has been shown that IVIg reduces the pathological deposition of anti-GM1-GM1 complexes (Bhatheja K, Field J. *Int J Biochem Cell Biol.* 2006; 38(12):1995). Standard treatment for MMN is IVIg; however, this treatment is not effective when administered over a long period. Therefore, the complement inhibitory effect of IVIg was investigated using the in vitro MMN model using iPSC derived motor neurons. To this end, iPSC-derived motor neurons were cultured on coverslips, fixed and opsonized with MMN-patient serum prior to addition of complement active serum to activate the complement cascade. Two brands of IVIg (GammaQuin and Nanogam) were tested, and different approaches to IVIg treatment were evaluated as well. First, 50 mg/mL IVIg was added during the opsonization step where IVIg was not able to block C3 fixation on motor neurons. Secondly, administration of IVIg during opsonization and complement activation, or during complement activation only was performed, respectively. Both resulted in decreased C3 fixation and GammaQuin showed the strongest effect on complement inhibition compared to Nanogam (see FIG. 16).

To evaluate the anti-idiotypic effect of IVIg, a competition ELISA for GM1 was performed using MMN-patient sera. The results shown in FIG. 17 reveal that there was no competition effect of IVIg for GM1 binding in this assay. To summarize, IVIg treatment blocked C3 fixation when added during the complement activation step confirming that IVIg depleted C3 from serum. However, IVIg had no effect on idiotypic antibodies.

C. Conclusions

The complement inhibitory effect of ARGX-117, targeting human C2b, was evaluated in an in vitro model using iPSC-derived motor neurons, thereby mimicking the possible pathophysiology of MMN. The data demonstrate that the motor neurons in this system expressed complement regulatory proteins with highest expression of CD59. Moreover, it was shown that IgM anti-GM1 antibodies from MMN-patients activated the classical complement pathway and that C3 deposition was dependent on the presence of C2. ARGX-117 efficiently blocked complement activation not only in MMN patients but also blocked complement activation in CIDP and GBS patient samples. In addition, IVIg only blocked complement during the complement activation step and had no effect on anti-idiotypic antibodies.

The invention claimed is:

1. A method of treating a paraproteinemic neuropathy in a subject, the method comprising administering to the subject an anti-C2 antibody or antigen-binding fragment thereof comprising a heavy chain variable domain (VH) and a light chain variable domain (VL), wherein the VH comprises the amino acid sequence of SEQ ID NO: 8, and the VL comprises complementarity determining regions LCDR1, LCDR2, and LCDR3 comprising the amino acid sequences of SEQ ID NOs: 7, 6, and 5, respectively.

2. The method of claim 1, wherein the anti-C2 antibody or antigen-binding fragment thereof inhibits the classical complement pathway and/or the lectin complement pathway.

3. The method of claim 1, wherein the paraproteinemic neuropathy is a demyelinating neuropathy.

4. The method of claim 1, wherein the paraproteinemic neuropathy is characterised by the presence of autoantibodies, optionally wherein the autoantibodies target a neural antigen.

5. The method of claim 4, wherein the neural antigen is a ganglioside or myelin-associated glycoprotein (MAG), optionally wherein the ganglioside is selected from the group consisting of GM1, GM1b, GM2, GM3, GD1a, GD1b, GD2, GD3, GT1a, GT1b, GT3, and GQ1b.

6. The method of claim 1, wherein the paraproteinemic neuropathy is selected from the group consisting of: multifocal motor neuropathy (MMN), chronic inflammatory demyelinating polyneuropathy (CIDP), Guillain-Barre syndrome (GBS), Miller Fisher syndrome, acute motor axonal neuropathy (AMAN), acute motor and sensory axonal neuropathy (AMSAN), chronic ataxic neuropathy-ophthalmoplegia-IgM paraprotein-cold agglutinins-disialosyl antibodies (CANOMAD) syndrome, distal acquired demyelinating symmetric (DADS) neuropathy, monoclonal gammopathy associated peripheral neuropathy, anti-MAG peripheral neuropathy, and POEMS syndrome.

7. The method of claim 1, wherein the VL comprises the amino acid sequence of SEQ ID NO: 9.

8. The method of claim 1, wherein the antibody or antigen-binding fragment comprises a human IgG heavy chain constant domain.

9. The method of claim 1, wherein the antibody or antigen-binding fragment thereof comprises a heavy chain comprising the amino acid sequence of SEQ ID NO: 16 and a light chain comprising the amino acid sequence of SEQ ID NO: 20.

10. The method of claim 1, further comprising administering intravenous immunoglobulin to the subject.

11. The method of claim 1, further comprising administering rituximab to the subject.

* * * * *

SEQUENCE LISTING

```
<160> NUMBER OF SEQ ID NOS: 31

<210> SEQ ID NO 1
<211> LENGTH: 752
<212> TYPE: PRT
<213> ORGANISM: homo sapiens

<400> SEQUENCE: 1

Met Gly Pro Leu Met Val Leu Phe Cys Leu Leu Phe Leu Tyr Pro Gly
1               5                   10                  15

Leu Ala Asp Ser Ala Pro Ser Cys Pro Gln Asn Val Asn Ile Ser Gly
            20                  25                  30

Gly Thr Phe Thr Leu Ser His Gly Trp Ala Pro Gly Ser Leu Leu Thr
        35                  40                  45

Tyr Ser Cys Pro Gln Gly Leu Tyr Pro Ser Pro Ala Ser Arg Leu Cys
    50                  55                  60

Lys Ser Ser Gly Gln Trp Gln Thr Pro Gly Ala Thr Arg Ser Leu Ser
65                  70                  75                  80

Lys Ala Val Cys Lys Pro Val Arg Cys Pro Ala Pro Val Ser Phe Glu
                85                  90                  95

Asn Gly Ile Tyr Thr Pro Arg Leu Gly Ser Tyr Pro Val Gly Gly Asn
            100                 105                 110

Val Ser Phe Glu Cys Glu Asp Gly Phe Ile Leu Arg Gly Ser Pro Val
        115                 120                 125
```

-continued

```
Arg Gln Cys Arg Pro Asn Gly Met Trp Asp Gly Glu Thr Ala Val Cys
    130                 135                 140

Asp Asn Gly Ala Gly His Cys Pro Asn Pro Gly Ile Ser Leu Gly Ala
145                 150                 155                 160

Val Arg Thr Gly Phe Arg Phe Gly His Gly Asp Lys Val Arg Tyr Arg
                165                 170                 175

Cys Ser Ser Asn Leu Val Leu Thr Gly Ser Ser Glu Arg Glu Cys Gln
            180                 185                 190

Gly Asn Gly Val Trp Ser Gly Thr Glu Pro Ile Cys Arg Gln Pro Tyr
        195                 200                 205

Ser Tyr Asp Phe Pro Glu Asp Val Ala Pro Ala Leu Gly Thr Ser Phe
    210                 215                 220

Ser His Met Leu Gly Ala Thr Asn Pro Thr Gln Lys Thr Lys Glu Ser
225                 230                 235                 240

Leu Gly Arg Lys Ile Gln Ile Gln Arg Ser Gly His Leu Asn Leu Tyr
                245                 250                 255

Leu Leu Leu Asp Cys Ser Gln Ser Val Ser Glu Asn Asp Phe Leu Ile
            260                 265                 270

Phe Lys Glu Ser Ala Ser Leu Met Val Asp Arg Ile Phe Ser Phe Glu
        275                 280                 285

Ile Asn Val Ser Val Ala Ile Ile Thr Phe Ala Ser Glu Pro Lys Val
    290                 295                 300

Leu Met Ser Val Leu Asn Asp Asn Ser Arg Asp Met Thr Glu Val Ile
305                 310                 315                 320

Ser Ser Leu Glu Asn Ala Asn Tyr Lys Asp His Glu Asn Gly Thr Gly
                325                 330                 335

Thr Asn Thr Tyr Ala Ala Leu Asn Ser Val Tyr Leu Met Met Asn Asn
            340                 345                 350

Gln Met Arg Leu Leu Gly Met Glu Thr Met Ala Trp Gln Glu Ile Arg
        355                 360                 365

His Ala Ile Ile Leu Leu Thr Asp Gly Lys Ser Asn Met Gly Gly Ser
    370                 375                 380

Pro Lys Thr Ala Val Asp His Ile Arg Glu Ile Leu Asn Ile Asn Gln
385                 390                 395                 400

Lys Arg Asn Asp Tyr Leu Asp Ile Tyr Ala Ile Gly Val Gly Lys Leu
                405                 410                 415

Asp Val Asp Trp Arg Glu Leu Asn Glu Leu Gly Ser Lys Lys Asp Gly
            420                 425                 430

Glu Arg His Ala Phe Ile Leu Gln Asp Thr Lys Ala Leu His Gln Val
        435                 440                 445

Phe Glu His Met Leu Asp Val Ser Lys Leu Thr Asp Thr Ile Cys Gly
    450                 455                 460

Val Gly Asn Met Ser Ala Asn Ala Ser Asp Gln Glu Arg Thr Pro Trp
465                 470                 475                 480

His Val Thr Ile Lys Pro Lys Ser Gln Glu Thr Cys Arg Gly Ala Leu
                485                 490                 495

Ile Ser Asp Gln Trp Val Leu Thr Ala Ala His Cys Phe Arg Asp Gly
            500                 505                 510

Asn Asp His Ser Leu Trp Arg Val Asn Val Gly Asp Pro Lys Ser Gln
        515                 520                 525

Trp Gly Lys Glu Phe Leu Ile Glu Lys Ala Val Ile Ser Pro Gly Phe
    530                 535                 540

Asp Val Phe Ala Lys Lys Asn Gln Gly Ile Leu Glu Phe Tyr Gly Asp
```

```
545                 550                 555                 560

Asp Ile Ala Leu Leu Lys Leu Ala Gln Lys Val Lys Met Ser Thr His
                565                 570                 575

Ala Arg Pro Ile Cys Leu Pro Cys Thr Met Glu Ala Asn Leu Ala Leu
            580                 585                 590

Arg Arg Pro Gln Gly Ser Thr Cys Arg Asp His Glu Asn Glu Leu Leu
        595                 600                 605

Asn Lys Gln Ser Val Pro Ala His Phe Val Ala Leu Asn Gly Ser Lys
    610                 615                 620

Leu Asn Ile Asn Leu Lys Met Gly Val Glu Trp Thr Ser Cys Ala Glu
625                 630                 635                 640

Val Val Ser Gln Glu Lys Thr Met Phe Pro Asn Leu Thr Asp Val Arg
                645                 650                 655

Glu Val Val Thr Asp Gln Phe Leu Cys Ser Gly Thr Gln Glu Asp Glu
            660                 665                 670

Ser Pro Cys Lys Gly Glu Ser Gly Gly Ala Val Phe Leu Glu Arg Arg
        675                 680                 685

Phe Arg Phe Phe Gln Val Gly Leu Val Ser Trp Gly Leu Tyr Asn Pro
    690                 695                 700

Cys Leu Gly Ser Ala Asp Lys Asn Ser Arg Lys Arg Ala Pro Arg Ser
705                 710                 715                 720

Lys Val Pro Pro Pro Arg Asp Phe His Ile Asn Leu Phe Arg Met Gln
                725                 730                 735

Pro Trp Leu Arg Gln His Leu Gly Asp Val Leu Asn Phe Leu Pro Leu
            740                 745                 750


<210> SEQ ID NO 2
<211> LENGTH: 9
<212> TYPE: PRT
<213> ORGANISM: artificial
<220> FEATURE:
<223> OTHER INFORMATION: HCDR3

<400> SEQUENCE: 2

Glu Asp Asp His Asp Ala Phe Ala Tyr
1               5


<210> SEQ ID NO 3
<211> LENGTH: 17
<212> TYPE: PRT
<213> ORGANISM: artificial
<220> FEATURE:
<223> OTHER INFORMATION: HCDR2

<400> SEQUENCE: 3

Asp Ile Asn Pro Asn Tyr Glu Ser Thr Gly Tyr Asn Gln Lys Phe Lys
1               5                   10                  15

Gly


<210> SEQ ID NO 4
<211> LENGTH: 5
<212> TYPE: PRT
<213> ORGANISM: artificial
<220> FEATURE:
<223> OTHER INFORMATION: HCDR1

<400> SEQUENCE: 4

Asp Tyr Asn Met Asp
1               5
```

<210> SEQ ID NO 5
<211> LENGTH: 9
<212> TYPE: PRT
<213> ORGANISM: artificial
<220> FEATURE:
<223> OTHER INFORMATION: LCDR3

<400> SEQUENCE: 5

```
Gln His Ser Arg Glu Leu Pro Tyr Thr
1               5
```

<210> SEQ ID NO 6
<211> LENGTH: 7
<212> TYPE: PRT
<213> ORGANISM: artificial
<220> FEATURE:
<223> OTHER INFORMATION: LCDR2

<400> SEQUENCE: 6

```
Leu Ala Ser Asn Leu Lys Ser
1               5
```

<210> SEQ ID NO 7
<211> LENGTH: 15
<212> TYPE: PRT
<213> ORGANISM: artificial
<220> FEATURE:
<223> OTHER INFORMATION: LCDR1

<400> SEQUENCE: 7

```
Arg Ala Ser Lys Ser Val Arg Thr Ser Gly Tyr Asn Tyr Met His
1               5                   10                  15
```

<210> SEQ ID NO 8
<211> LENGTH: 118
<212> TYPE: PRT
<213> ORGANISM: artificial
<220> FEATURE:
<223> OTHER INFORMATION: VH

<400> SEQUENCE: 8

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Thr Gly Gln Gly Leu Glu Trp Ile
        35                  40                  45

Gly Asp Ile Asn Pro Asn Tyr Glu Ser Thr Gly Tyr Asn Gln Lys Phe
    50                  55                  60

Lys Gly Arg Ala Thr Met Thr Val Asp Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp His Asp Ala Phe Ala Tyr Trp Gly Gln Gly Thr
            100                 105                 110

Leu Val Thr Val Ser Ser
        115
```

<210> SEQ ID NO 9
<211> LENGTH: 111
<212> TYPE: PRT
<213> ORGANISM: artificial
<220> FEATURE:

<223> OTHER INFORMATION: VL

<400> SEQUENCE: 9

```
Asp Asn Val Leu Thr Gln Ser Pro Asp Ser Leu Ala Val Ser Leu Gly
1               5                   10                  15

Glu Arg Ala Thr Ile Ser Cys Arg Ala Ser Lys Ser Val Arg Thr Ser
            20                  25                  30

Gly Tyr Asn Tyr Met His Trp Tyr Gln Gln Lys Pro Gly Gln Pro Pro
        35                  40                  45

Lys Leu Leu Ile Tyr Leu Ala Ser Asn Leu Lys Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Thr Tyr Tyr Cys Gln His Ser Arg
                85                  90                  95

Glu Leu Pro Tyr Thr Phe Gly Gln Gly Thr Lys Leu Glu Ile Lys
            100                 105                 110
```

<210> SEQ ID NO 10
<211> LENGTH: 330
<212> TYPE: PRT
<213> ORGANISM: homo sapiens

<400> SEQUENCE: 10

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
```

```
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 11
<211> LENGTH: 329
<212> TYPE: PRT
<213> ORGANISM: homo sapiens

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300

Val Phe Ser Cys Ser Val Met His Glu Ala Leu Lys Phe His Tyr Thr
305                 310                 315                 320

Gln Lys Ser Leu Ser Leu Ser Pro Gly
                325


<210> SEQ ID NO 12
<211> LENGTH: 327
<212> TYPE: PRT
<213> ORGANISM: homo sapiens

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

```
<210> SEQ ID NO 13
<211> LENGTH: 327
<212> TYPE: PRT
<213> ORGANISM: homo sapiens

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325


<210> SEQ ID NO 14
<211> LENGTH: 327
<212> TYPE: PRT
<213> ORGANISM: homo sapiens

<400> SEQUENCE: 14
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu Lys Phe His Tyr Thr Gln Lys Ser
305                 310                 315                 320

Leu Ser Leu Ser Pro Gly Lys
                325


<210> SEQ ID NO 15
<211> LENGTH: 448
<212> TYPE: PRT
<213> ORGANISM: artificial
<220> FEATURE:
<223> OTHER INFORMATION: IgG1

<400> SEQUENCE: 15

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30
```

```
Asn Met Asp Trp Val Arg Gln Ala Thr Gly Gln Gly Leu Glu Trp Ile
        35                  40                  45

Gly Asp Ile Asn Pro Asn Tyr Glu Ser Thr Gly Tyr Asn Gln Lys Phe
    50                  55                  60

Lys Gly Arg Ala Thr Met Thr Val Asp Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp His Asp Ala Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 16
<211> LENGTH: 447
<212> TYPE: PRT
<213> ORGANISM: artificial
<220> FEATURE:
<223> OTHER INFORMATION: IgG1-LALA-NHance

<400> SEQUENCE: 16

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Thr Gly Gln Gly Leu Glu Trp Ile
        35                  40                  45

Gly Asp Ile Asn Pro Asn Tyr Glu Ser Thr Gly Tyr Asn Gln Lys Phe
    50                  55                  60

Lys Gly Arg Ala Thr Met Thr Val Asp Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp His Asp Ala Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365
```

```
Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu Lys Phe His Tyr Thr Gln Lys Ser Leu Ser Leu Ser Pro Gly
        435                 440                 445


<210> SEQ ID NO 17
<211> LENGTH: 445
<212> TYPE: PRT
<213> ORGANISM: artificial
<220> FEATURE:
<223> OTHER INFORMATION: IgG4

<400> SEQUENCE: 17

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Thr Gly Gln Gly Leu Glu Trp Ile
        35                  40                  45

Gly Asp Ile Asn Pro Asn Tyr Glu Ser Thr Gly Tyr Asn Gln Lys Phe
    50                  55                  60

Lys Gly Arg Ala Thr Met Thr Val Asp Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp His Asp Ala Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285
```

```
Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445
```

<210> SEQ ID NO 18
<211> LENGTH: 445
<212> TYPE: PRT
<213> ORGANISM: artificial
<220> FEATURE:
<223> OTHER INFORMATION: IgG4-S228P-L445P

<400> SEQUENCE: 18

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Thr Gly Gln Gly Leu Glu Trp Ile
        35                  40                  45

Gly Asp Ile Asn Pro Asn Tyr Glu Ser Thr Gly Tyr Asn Gln Lys Phe
    50                  55                  60

Lys Gly Arg Ala Thr Met Thr Val Asp Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp His Asp Ala Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205
```

```
Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 19
<211> LENGTH: 445
<212> TYPE: PRT
<213> ORGANISM: artificial
<220> FEATURE:
<223> OTHER INFORMATION: IgG4-S228P-NHance-L445P

<400> SEQUENCE: 19

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Thr Gly Gln Gly Leu Glu Trp Ile
        35                  40                  45

Gly Asp Ile Asn Pro Asn Tyr Glu Ser Thr Gly Tyr Asn Gln Lys Phe
    50                  55                  60

Lys Gly Arg Ala Thr Met Thr Val Asp Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp His Asp Ala Phe Ala Tyr Trp Gly Gln Gly Thr
            100                 105                 110

Leu Val Thr Val Ser Ser Ala Ser Thr Lys Gly Pro Ser Val Phe Pro
        115                 120                 125
```

```
Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu Lys Phe
            420                 425                 430

His Tyr Thr Gln Lys Ser Leu Ser Leu Ser Pro Gly Lys
        435                 440                 445


<210> SEQ ID NO 20
<211> LENGTH: 218
<212> TYPE: PRT
<213> ORGANISM: artificial
<220> FEATURE:
<223> OTHER INFORMATION: Light Chain

<400> SEQUENCE: 20

Asp Asn Val Leu Thr Gln Ser Pro Asp Ser Leu Ala Val Ser Leu Gly
1               5                   10                  15

Glu Arg Ala Thr Ile Ser Cys Arg Ala Ser Lys Ser Val Arg Thr Ser
            20                  25                  30

Gly Tyr Asn Tyr Met His Trp Tyr Gln Gln Lys Pro Gly Gln Pro Pro
        35                  40                  45
```

```
Lys Leu Leu Ile Tyr Leu Ala Ser Asn Leu Lys Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Thr Tyr Tyr Cys Gln His Ser Arg
                85                  90                  95

Glu Leu Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 21
<211> LENGTH: 10
<212> TYPE: PRT
<213> ORGANISM: homo sapiens

<400> SEQUENCE: 21

Glu Pro Lys Ser Cys Asp Lys Thr His Thr
1               5                   10


<210> SEQ ID NO 22
<211> LENGTH: 5
<212> TYPE: PRT
<213> ORGANISM: homo sapiens

<400> SEQUENCE: 22

Cys Pro Pro Cys Pro
1               5


<210> SEQ ID NO 23
<211> LENGTH: 8
<212> TYPE: PRT
<213> ORGANISM: homo sapiens

<400> SEQUENCE: 23

Ala Pro Glu Leu Leu Gly Gly Pro
1               5


<210> SEQ ID NO 24
<211> LENGTH: 12
<212> TYPE: PRT
<213> ORGANISM: homo sapiens

<400> SEQUENCE: 24

Glu Leu Lys Thr Pro Leu Gly Asp Thr Thr His Thr
1               5                   10


<210> SEQ ID NO 25
```

<211> LENGTH: 50
<212> TYPE: PRT
<213> ORGANISM: homo sapiens

<400> SEQUENCE: 25

```
Cys Pro Arg Cys Pro Glu Pro Lys Ser Cys Asp Thr Pro Pro Pro Cys
1               5                   10                  15

Pro Arg Cys Pro Glu Pro Lys Ser Cys Asp Thr Pro Pro Pro Cys Pro
            20                  25                  30

Arg Cys Pro Glu Pro Lys Ser Cys Asp Thr Pro Pro Pro Cys Pro Arg
        35                  40                  45

Cys Pro
    50
```

<210> SEQ ID NO 26
<211> LENGTH: 7
<212> TYPE: PRT
<213> ORGANISM: homo sapiens

<400> SEQUENCE: 26

```
Glu Ser Lys Tyr Gly Pro Pro
1               5
```

<210> SEQ ID NO 27
<211> LENGTH: 5
<212> TYPE: PRT
<213> ORGANISM: homo sapiens

<400> SEQUENCE: 27

```
Cys Pro Ser Cys Pro
1               5
```

<210> SEQ ID NO 28
<211> LENGTH: 8
<212> TYPE: PRT
<213> ORGANISM: homo sapiens

<400> SEQUENCE: 28

```
Ala Pro Glu Phe Leu Gly Gly Pro
1               5
```

<210> SEQ ID NO 29
<211> LENGTH: 3
<212> TYPE: PRT
<213> ORGANISM: homo sapiens

<400> SEQUENCE: 29

```
Glu Arg Lys
1
```

<210> SEQ ID NO 30
<211> LENGTH: 10
<212> TYPE: PRT
<213> ORGANISM: homo sapiens

<400> SEQUENCE: 30

```
Cys Cys Val Glu Cys Pro Pro Pro Cys Pro
1               5                   10
```

<210> SEQ ID NO 31
<211> LENGTH: 7
<212> TYPE: PRT
<213> ORGANISM: homo sapiens

<400> SEQUENCE: 31

```
Ala Pro Pro Val Ala Gly Pro
1               5
```